United States Patent
Gartner et al.

(10) Patent No.: US 10,920,190 B2
(45) Date of Patent: Feb. 16, 2021

(54) FOLDING BIOLOGICAL TISSUE VIA PROGRAMMED CELLULAR CONTRACTILITY

(71) Applicant: The Regents of the University of California, Oakland, CA (US)

(72) Inventors: Zev Jordan Gartner, Pacifica, CA (US); Alex James Hughes, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 13 days.

(21) Appl. No.: 16/098,704

(22) PCT Filed: May 3, 2017

(86) PCT No.: PCT/US2017/030873
§ 371 (c)(1),
(2) Date: Nov. 2, 2018

(87) PCT Pub. No.: WO2017/192742
PCT Pub. Date: Nov. 9, 2017

(65) Prior Publication Data
US 2019/0136178 A1 May 9, 2019

Related U.S. Application Data

(60) Provisional application No. 62/331,908, filed on May 4, 2016, provisional application No. 62/397,761, filed on Sep. 21, 2016, provisional application No. 62/449,958, filed on Jan. 24, 2017.

(51) Int. Cl.
| | |
|---|---|
| *C12N 5/00* | (2006.01) |
| *A61K 35/37* | (2015.01) |
| *A61L 27/38* | (2006.01) |
| *A61L 27/54* | (2006.01) |
| *A61L 27/58* | (2006.01) |
| *A61K 35/00* | (2006.01) |
| *B33Y 10/00* | (2015.01) |
| *B33Y 70/00* | (2020.01) |
| *B33Y 80/00* | (2015.01) |
| *A61F 2/02* | (2006.01) |
| *C12M 3/00* | (2006.01) |

(52) U.S. Cl.
CPC ............ *C12N 5/0068* (2013.01); *A61F 2/022* (2013.01); *A61K 35/37* (2013.01); *A61L 27/3808* (2013.01); *A61L 27/3813* (2013.01); *A61L 27/3826* (2013.01); *A61L 27/3886* (2013.01); *A61L 27/54* (2013.01); *A61L 27/58* (2013.01); *B33Y 10/00* (2014.12); *B33Y 70/00* (2014.12); *B33Y 80/00* (2014.12); *C12M 21/08* (2013.01); *C12N 5/0062* (2013.01); *A61F 2240/001* (2013.01); *A61K 35/00* (2013.01); *C12N 2513/00* (2013.01); *C12N 2533/12* (2013.01); *C12N 2533/52* (2013.01); *C12N 2533/54* (2013.01); *C12N 2533/90* (2013.01); *C12N 2535/00* (2013.01)

(58) Field of Classification Search
None
See application file for complete search history.

(56) References Cited

U.S. PATENT DOCUMENTS

| | | | |
|---|---|---|---|
| 2014/0170204 A1 | 6/2014 | Desai et al. | |
| 2014/0294782 A1 | 10/2014 | Gartner et al. | |
| 2016/0010054 A1 | 1/2016 | Gartner et al. | |
| 2016/0032239 A1* | 2/2016 | Livermore-Clifford | ..................... A61L 27/18 435/395 |

FOREIGN PATENT DOCUMENTS

WO 2014071388 5/2014

OTHER PUBLICATIONS

Kuribayashi-Shigetomi et al. "Cell origami: self-folding of three-dimensional cell-laden microstructures driven by cell traction force." PloS One 7.12 (2012): e51085. (Year: 2012).*
Vasiev et al. "Self-folding nano-and micropatterned hydrogel tissue engineering scaffolds by single step photolithographic process." Microelectronic Engineering 108 (2013): 76-81. (Year: 2013).*
Todhunter et al. (2015) "Programmed synthesis of three-dimensional tissues" Nature Methods 12(10): 1-9.
Todhunter et al. (2016) Fabrication of 3-D Reconstituted Organoid Arrays by DNA-Programmed Assembly of Cells (DPAC); Current Protocols in Chemical Biology, 147-178.
Tseng et al. (2012) "Spatial organization of the extracellular matrix regulates cell-cell junction positioning" Proc. Natl. Acad. Sci. U.S.A. 109, 1506-1511.
Broaders et al. (2015) "Coupling between apical tension and basal adhesion allow epithelia to collectively sense and respond to substrate topography over long distances" Integr Biol 7(12): 1611-1621.
Chen et al. (2015) "Optical Imaging, Expansion microscopy" Science 347(6221): 543-548.
Debnath et al. (2003) "Morphogenesis and oncogenesis of MCF-10A mammary epithelial acini grown in three-dimensional basement membrane cultures" Methods 30, 256-268.

(Continued)

*Primary Examiner* — Emily A Cordas
(74) *Attorney, Agent, or Firm* — Edward J. Baba; Shweta Chandra; Bozicevic, Field & Francis LLP

(57) ABSTRACT

The present disclosure provides methods and systems for generating biological tissues that are configured for folding into a pre-determined three-dimensional form. The present disclosure utilizes contractile cells for folding a biological tissue into a three-dimensional shape. The methods include disposing a pattern of contractile cells on a surface that includes fibers actuated by the contractile cells and folding of the surface by the action of the contractile cells on the fibers. Tissues generated using the methods and systems of the present disclosure are also provided.

15 Claims, 42 Drawing Sheets

(56) References Cited

OTHER PUBLICATIONS

Ishida et al. (2014) "Epithelial Sheet Folding Induces Lumen Formation by Madin-Darby Canine Kidney Cells in a Collagen Gel" PLOS One 9(8): e99655, pp. 1-11.
Liu et al. (2012) "Programmed Cell-to-Cell Variability in Ras Activity Triggers Emergent Behaviors during Mammary Epithelial Morphogenesis" Cell Reports 2, 1461-1470.
Puspoki et al. (2016) "Chapter 3, Transforms and Operators for Directional Bioimage Analysis: A Survey" Focus on Bio-Image Informatics, Springer International Publishing 219, 69-93.
Schindler et al. (2005) "A synthetic nanofibrillar matrix promotes in vivo-like organization and morphogenesis for cells in culture" Biomaterials 26(28): 5624-5631.
Selden, et al. (2012) "Chemically programmed cell adhesion with membrane-anchored oligonucleotides" NIH Public Access J. Am. Chem. Soc. 134, 1-10.
Stampfer et al. (2013) "An Integrated Human Mammary Epithelial Cell Culture System for Studying Carginogenesis and Aging" Cell and Molecular Biology of Breast Cancer, 323-361 (Humana Press).

* cited by examiner $C_1 = 1/R_1$  
$C_1 = 1/R_1$ } Principal curvatures $H = (C_1 + C_2)/2$ → Mean curvature $H = C_1 \times C_2$ → Gaussian curvature $C_1$ $C_2$ H K Plane 0 0 0 0

Cylinder

+ 0 + 0

Saddle

+ − 0 −

Sphere

+ + + +

C

A

*model* s = 1 s = 0.5

200 μm non-active edge, stiffness $k_1$, rest length = initial length active edge, stiffness $k_2$, rest length = s

B

C

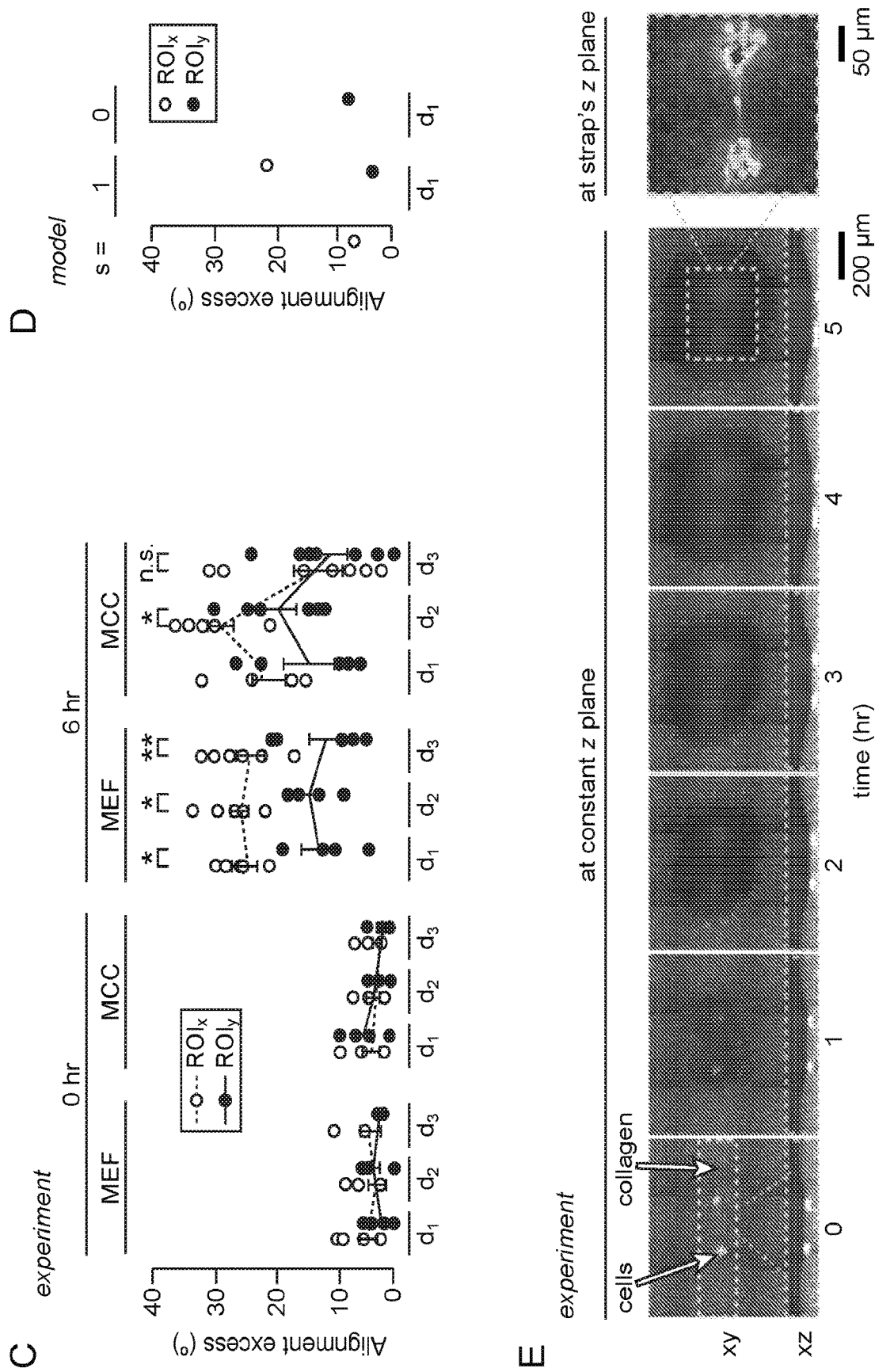

*folding motifs*

(A) isotropic (B) anisotropic (C) curl (D) compound (E) opposing — active edges, spring network

B

C

D

E

F

G

C

FOLDING BIOLOGICAL TISSUE VIA PROGRAMMED CELLULAR CONTRACTILITY

INTRODUCTION

Living tissues are characterized by layers of cells and extracellular matrix (ECM). Interfaces between layers are often folded into more complex topographies such as the acini of the breast, the folds of the cerebral cortex, the dermal epidermal junction, and the crypts and villi of the intestine. There is considerable interest in generating tissues in vitro that can fold into three-dimensional form and can serve as a model for in vitro folding of tissue.

SUMMARY

The present disclosure provides methods and systems for generating tissues that are configured for folding into a three-dimensional form based upon placement of contractile cells in the tissue. The positioning of contractile cells in the tissue determines the three-dimensional shape into which the tissue is folded. As such, tissues generated by the methods, and systems taught herein, in some embodiments, fold into a pre-determined 3D-form, which is dictated by the pattern of contractile cells present in the tissues.

The methods of the present disclosure include disposing a pattern of contractile cells in conjunction with fibers on which the contractile cells act and thereby allowing folding of the resulting tissue into a 3D-form.

In certain aspects, the methods disclosed herein include disposing a pattern of contractile cells on a layer that includes a matrix of fibers (e.g., an extracellular matrix (ECM)) and folding of the layer by the action of the contractile cells on the fibers present in the ECM.

The presently disclosed methods also include generating a three dimensional tissue that includes a pattern of contractile cells disposed within a matrix of fibers. The three dimensional tissue, in some embodiments, folds into various shapes based on the placement of the contractile cells in the matrix of fibers.

Also provided are 3D-tissue generated using the methods and systems disclosed herein.

In certain aspects, a method of making a planar biological tissue configured for folding into a three-dimensional shape involves patterning contractile cells on a surface of a substrate, comprising disposing a pattern of nucleic acids on a surface of a substrate; and contacting the patterned nucleic acids under hybridization conditions with a suspension of the contractile cells, wherein the contractile cells comprise cell surface-attached nucleic acids complementary to the patterned nucleic acids, and wherein the cell surface-attached nucleic acids hybridize to the patterned nucleic acids to generate patterned contractile cells on the surface of the substrate; contacting the patterned contractile cells on the surface of the substrate with a polymer matrix comprising fibers thereby embedding the patterned contractile cells into the polymer matrix; removing the polymer matrix from the surface of the substrate, wherein the patterned contractile cells are retained in the polymer matrix upon removal thereby generating a planar biological tissue configured for folding into a three-dimensional shape; contacting the planar biological tissue with a culture medium; and incubating the planar biological tissue in suspension in the culture medium for a period of time sufficient for action of the contractile cells on the fibers for folding the tissue into a three-dimensional shape.

In certain aspects, the patterning contractile cells on a surface of a substrate, includes disposing a pattern of nucleic acids on a first surface of a first substrate and a first surface of a second substrate, wherein the first surface of the first substrate is spaced apart from the first surface of the second substrate via a gap between the first and second substrates and wherein the surfaces are in a facing configuration to each other; and contacting the patterned nucleic acids under hybridization conditions with a suspension of the contractile cells, wherein the contractile cells comprise cell surface-attached nucleic acids complementary to the patterned nucleic acids, and wherein the cell surface-attached nucleic acids hybridize to the patterned nucleic acids to generate patterned contractile cells on the first surface of the first substrate and the first surface of the second substrate; wherein removing the polymer matrix comprises removing the polymer matrix from between the first and second substrates thereby generating a planar biological tissue comprising the patterned contractile cells on a top surface and a bottom surface of the planar biological tissue.

In certain embodiments, the planar biological may include a region containing polymer matrix and pattern of cells and a region containing polymer matrix that is devoid of cells and wherein incubating the planar biological tissue in suspension for folding the tissue into a three-dimensional shape comprises separating the region containing polymer matrix and pattern of cells from the region containing polymer matrix that is devoid of cells and incubating the region containing polymer matrix and pattern of cells.

In certain embodiments, the pattern of nucleic acids is two-dimensional. In certain embodiments, the method includes solubilizing the polymer matrix in the three-dimensional shape to yield a three-dimensional shape comprising fibers and contractile cells.

In certain embodiments, the pattern of nucleic acids may include a single population of nucleic acids having the same nucleotide sequence. In certain embodiments, the pattern of nucleic acids comprises two or more population of nucleic acids, wherein each population of nucleic acids comprises a unique nucleotide sequence. In certain embodiments, the pattern of nucleic acids comprises two or more population of nucleic acids, wherein each population of nucleic acids comprises a unique nucleotide sequence, wherein the nucleic acids of each population are uniquely addressable on the surface of the substrate. In certain embodiments, the pattern of nucleic acids comprises two or more population of nucleic acids, wherein each population of nucleic acids comprises a unique nucleotide sequence, wherein the nucleic acids of each population are uniquely addressable on the first surface of the first and/or second substrate. In certain embodiments, the suspension of contractile cells comprises two or more unique populations of contractile cells, wherein each population of contractile cells comprises surface-attached nucleic acids complementary to one of the populations of nucleic acids in the pattern.

In certain cases, the disposing comprises printing a liquid comprising the nucleic acids on the substrate. In certain cases, the cell surface-attached nucleic acids comprise a lipid moiety attached to a nucleic acid, which surface-attached nucleic acids are attached to the contractile cells by insertion of the lipid moiety into the plasma membrane of the contractile cells. In certain cases, the cell surface-attached nucleic acids comprise a spacer between the lipid moiety and the nucleic acid. In some cases, removing the polymer matrix from the surface of the substrate comprises exposing the polymer matrix to a nuclease.

In some aspects, the fibers are provided in an extracellular matrix (ECM). In some embodiments, the ECM is synthetic or obtained from a biological source. In some aspects, the ECM is secreted by a cell line. In some aspects, the fibers comprise collagen. In some cases, the collagen is synthetic.

In some embodiments, a method of making a planar biological tissue configured for folding into a three-dimensional shape includes disposing, on a substrate, a polymer layer comprising fibers; patterning contractile cells on the polymer layer such that the contractile cells are disposed in a spaced-apart manner from each other on the polymer layer; and incubating contractile cells on the polymer layer under conditions sufficient to permit adherence of the contractile cells to the polymer layer thereby generating a biological tissue configured for folding into a three-dimensional shape by action of the contractile cells on the fibers in the polymer layer.

In some embodiments, the contractile cells are patterned on a first surface of the polymer layer and the method further comprises patterning contractile cells on a second surface of the polymer layer, where the second surface is opposite the first surface, wherein the contractile cells are disposed in a spaced-apart manner from each other on the polymer layer. In certain embodiments, the pattern of contractile cells on the first surface is offset with reference to the pattern of contractile cells on the second surface. In certain embodiments, the contractile cells on the first surface are patterned in a circular shape and the contractile cells on the second surface are patterned into a ring that is larger in diameter than the circular shape.

In certain embodiments, the number of contractile cells patterned on the first surface and the number of contractile cells patterned on the second surface, opposite to the first surface, may be similar, such as, the number of cells may have a ratio of 0.75:1 to 1:0.75. For example, the number of contractile cells patterned on the first surface and the number of contractile cells patterned on the second surface may have a ratio of 0.75:1, 0.80:1, 0.9:1; 1:1; 1:0.9; 1:0.8; or 1:0.75.

In some cases, the patterning comprises printing the contractile cells in a spaced apart manner on the polymer layer. In some cases, the patterning comprises micro-pipetting the contractile cells in a spaced apart manner on the polymer layer.

In some cases, the method comprises incubating the biological tissue in a culture medium in suspension and folding the planar biological tissue into a three-dimensional shape.

In certain embodiments, the patterning comprises disposing a population of contractile cells comprising a single type of contractile cells. In some cases, the patterning comprises disposing a population of contractile cells comprising a two or more types of contractile cells. In other cases, the patterning comprises disposing a population of a first type of contractile cells in a first pattern and a population of a second type of contractile cells in a second pattern.

In another aspect, a method for generating a three-dimensional (3D) tissue configured for folding into a predetermined shape is disclosed. In certain cases, the method includes disposing a mixture of contractile cells and fibers on a substrate to form a 3D structure comprising the contractile cells and fibers; and incubating the structure in a culture medium under cell culture conditions for folding the structure into a predetermined shape.

In some cases, the method includes disposing a solution of fiber on the structure prior to the incubating. In some aspects, the method comprises repeating the disposing the mixture of contractile cells and fibers and/or solution of fibers on the structure prior to the incubating. In some aspects, the method comprises removing the structure from the substrate prior to the incubating. In certain cases, the disposing comprises printing, e.g., 3D-printing. In certain cases, the disposing comprises extrusion.

Also provided herein is a system for generating a planar biological tissue configured for folding into a three-dimensional shape In some cases, the system includes a population of nucleic acids disposed in a pattern on a surface of the substrate; a population of contractile cells comprising cell surface-attached nucleic acids complementary to the population of nucleic acids, wherein the population of cells is attached to the population of nucleic acids by hybridization of the surface-attached nucleic acids to the population of nucleic acids; and a polymer matrix comprising fibers.

In some cases, the first substrate is spaced apart from a second substrate, wherein a first surface of the first substrate is in a facing configuration to a first surface of the second substrate, wherein a population of nucleic acids is disposed in a pattern on the first surfaces of the first and second substrates.

In another aspect, a system for generating a planar biological tissue configured for folding into a three-dimensional shape, the system comprising a polymer layer comprising a layer comprising fibers disposed on a surface of the polymer layer; and a population of contractile cells.

In another aspect, a system for generating a planar biological tissue configured for folding into a three-dimensional shape includes a polymer layer comprising a layer comprising fibers disposed on a top surface and a bottom surface of the polymer layer; and a population of contractile cells. In certain embodiments, the fibers are provided in an extracellular matrix.

An engineered three-dimensional (3D) biological tissue comprising a pre-determined pattern of contractile cells, wherein the pre-determined pattern of contractile cells determines the shape of the 3D biological tissue is also disclosed. In certain cases, the biological tissue comprises only one type of contractile cells. In certain cases, the biological tissue comprises only two types of contractile cells. In certain embodiments, the one type of contractile cells comprise fibroblasts. In certain embodiments, the two types of contractile cells comprise fibroblasts and epithelial cells. In certain cases, the pattern of biological tissue comprises spaced-apart clusters of contractile cells. In some embodiments, each cluster comprises 5-100 contractile cells. In some examples, each cluster comprises 5-50 contractile cells. In yet other aspects, each cluster comprises 5-10 contractile cells. In some cases, the biological tissue includes a pre-determined concentration of fibers. In some embodiments, the biological tissue is devoid of one or more of blood cells, adipocytes, and nerve cells. In certain embodiments, the biological tissue is devoid of one or more of red blood cells and immune cells.

In some aspects, the contractile cells are selected from the group consisting of: fibroblasts, epithelial cells, endothelial cells, skeletal muscle cells, smooth cells, cardiac cells, progenitors thereof, and combinations thereof.

In some aspects, the polymer matrix may be hydrogels, alginate, poly-caprolactone (PCL), gelatin, agarose, or cellulose polymer. In some cases, the fibers comprise collagen or fibronectin. Collagen may be synthetic or obtained from a biological source.

In certain cases, the biological tissue generated using the methods disclosed herein may be induced to fold into a predetermined shape by constraining a portion of the biological tissue such that the portion does not undergo folding.

DETAILED DESCRIPTION

Figure 1:
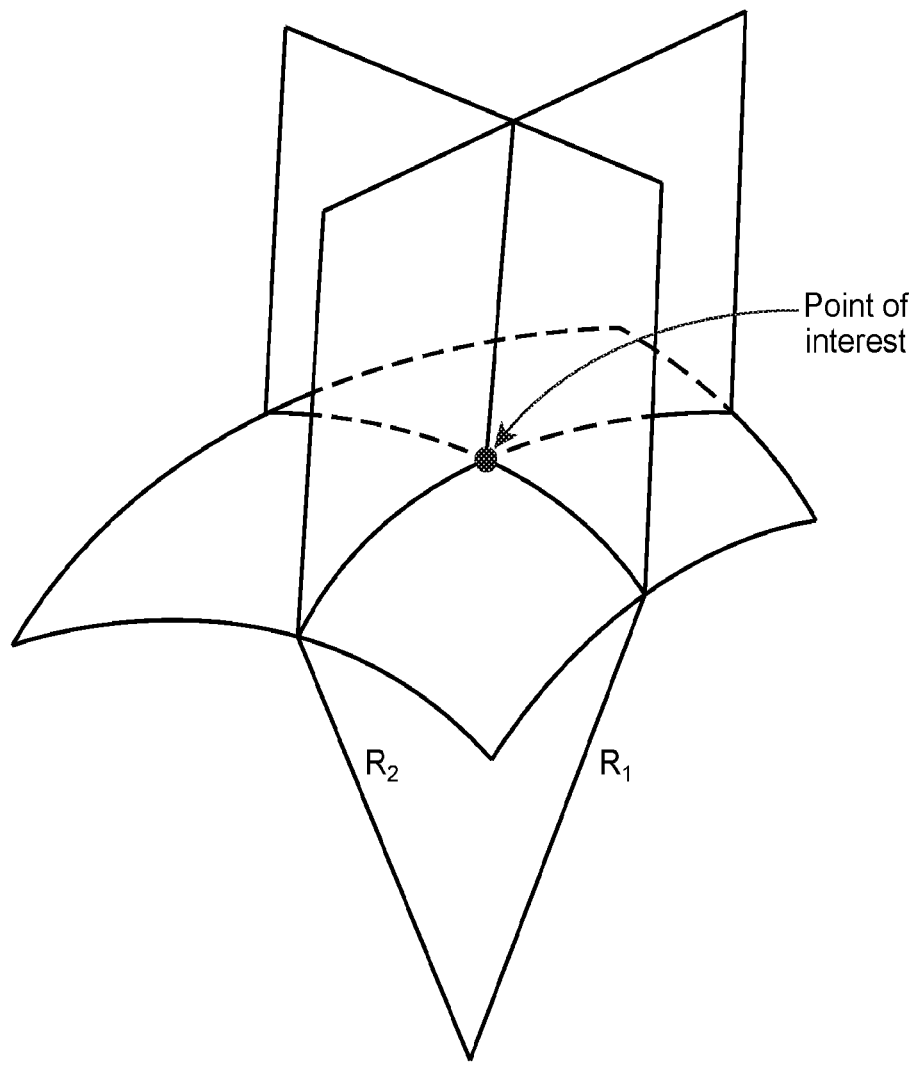
FIG. 1 is a schematic depicting out of plane curvatures and measurements of the same.
Figure 2:
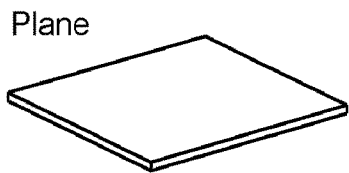
FIG. 2 is a schematic depicting the curvatures in three dimensional shapes contrasted with a planar shape.
Figure 2:
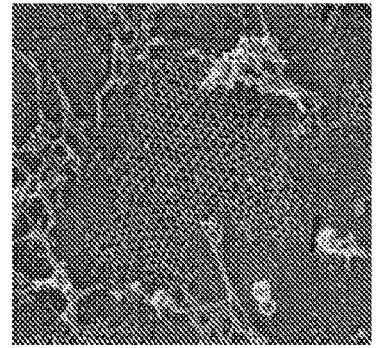
Figure 2:
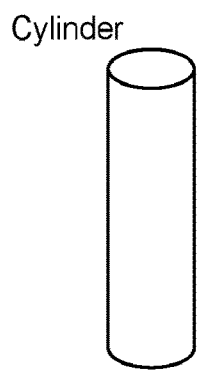
Figure 2:
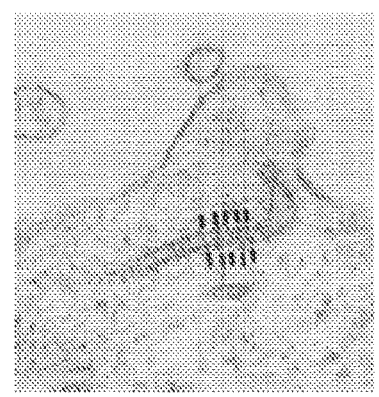
Figure 2:
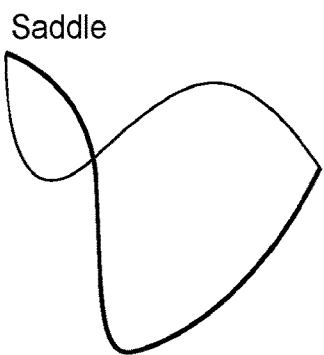
Figure 2:
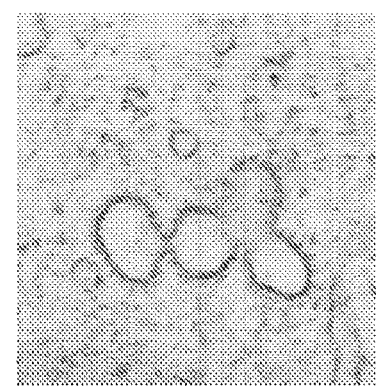
Figure 2:
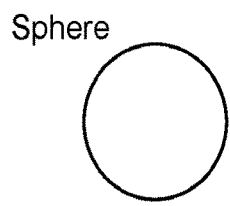
Figure 2:
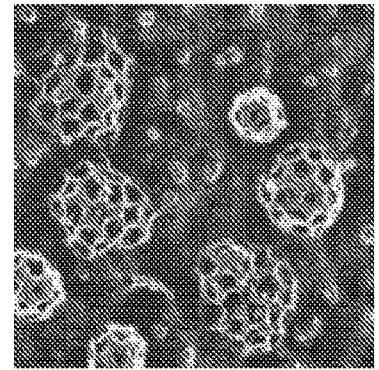
Figure 3:
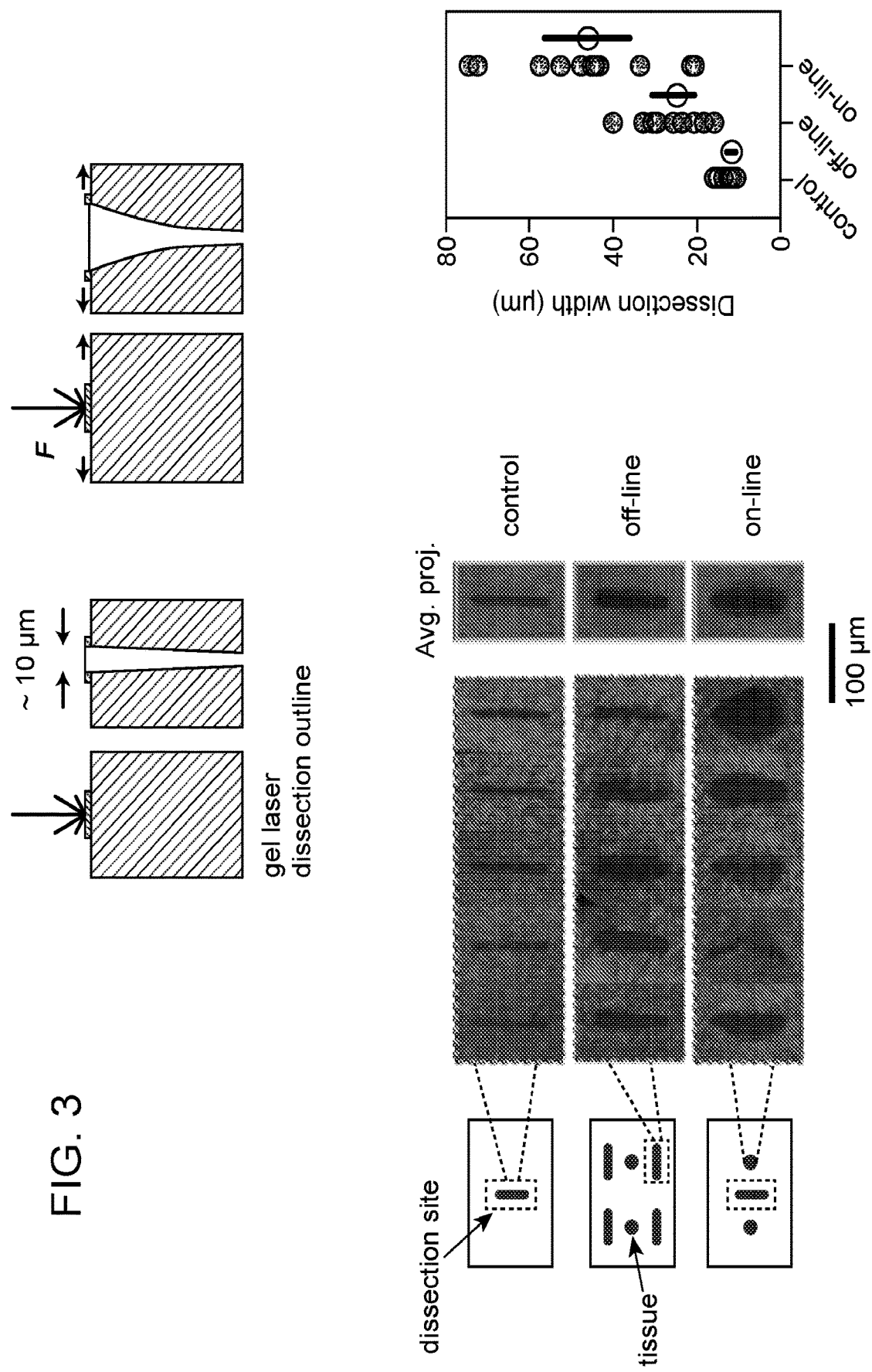
FIG. 3 illustrates that areas of aligned collagen are under tension. Laser microdissection of the gel between tissue pairs after straps had formed yielded significantly higher retraction distances of the surface of the gel in comparison to retraction of regions orthogonal to the strap and to control regions distant from tissues.

The present disclosure provides methods and systems for generating tissues that are configured for folding into a three-dimensional form. The present disclosure utilizes contractile cells for folding a tissue into a three-dimensional shape. The methods include disposing a pattern of contractile cells in conjunction with a matrix of fibers, upon which the contractile cells act, to generate a tissue and folding of the tissue by the action of the contractile cells on the fibers. Also provided are 3D-tissue generated using the methods and systems disclosed herein.

Before exemplary embodiments of the present invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a," "an," and "the" include plural referents unless the context clearly dictates otherwise. Thus, for example, reference to "a membrane anchored polynucleotide" includes a plurality of such membrane-anchored polynucleotides and reference to "the polynucleotide" includes reference to one or more polynucleotides, and so forth.

It is further noted that the claims may be drafted to exclude any element which may be optional. As such, this statement is intended to serve as antecedent basis for use of such exclusive terminology as "solely," "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. To the extent such publications may set out definitions of a term that conflicts with the explicit or implicit definition of the present disclosure, the definition of the present disclosure controls.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Definitions

The terms "membrane surface-attached nucleic acid," "membrane-anchored polynucleotide," "lipid-DNA" and similar terms encompass an oligonucleotide or polynucleotide that is attached by any means to a hydrophobic, lipophilic, or amphiphilic moiety that can be inserted into a membrane, regardless of whether the "membrane-anchored polynucleotide" or portion thereof is actually inserted into a membrane. An oligonucleotide or polynucleotide may also be attached to a membrane of a cell by NHS-ester reaction with amines and bi-orthogonal chemical reactions with glycocalyx present in a membrane and thus may not include a hydrophobic, lipophilic, or amphiphilic region for insertion into a membrane. A polynucleotide may be attached to surface of a glass substrate via any reliable method. A polynucleotide attached to surface of a glass substrate may optionally include a hydrophobic, lipophilic, or amphiphilic region.

The term "membrane" or any similar term is used broadly and generically herein to refer to any lipid-containing membrane, cellular membrane, monolayer, bilayer, vesicle, liposome, lipid bilayer, etc., and the present invention is not meant to be limited to any particular membranes.

The particular use of terms "nucleic acid," "oligonucleotide," and "polynucleotide" should in no way be considered limiting and may be used interchangeably herein. "Oligonucleotide" is used when the relevant nucleic acid molecules typically comprise less than about 100 bases. "Polynucleotide" is used when the relevant nucleic acid molecules typically comprise more than about 100 bases. Both terms are used to denote DNA, RNA, modified or synthetic DNA or RNA (including but not limited to nucleic acids comprising synthetic and naturally-occurring base analogs, dideoxy or other sugars, thiols or other non-natural or natural polymer backbones), or other nucleobase containing polymers. Accordingly, the terms should not be construed to define or limit the length of the nucleic acids referred to and used herein.

Polynucleotides of the present disclosure may be single-stranded, double-stranded, triple-stranded, or include a combination of these conformations. Generally polynucleotides contain phosphodiester bonds, although in some cases, as outlined below, nucleic acid analogs are included that may have alternate backbones, comprising, for example, phosphoramide, phosphorothioate, phosphorodithioate, O-methylphophoroamidite linkages, and peptide nucleic acid backbones and linkages. Other analog nucleic acids include morpholinos, as well as those with positive backbones, non-ionic backbones, and non-ribose backbones. Nucleic acids containing one or more carbocyclic sugars are also included within the definition of nucleic acids. These modifications of the ribose-phosphate backbone may be done to facilitate the addition of additional moieties such as labels, or to increase the stability and half-life of such molecules in physiological environments.

The term "nucleic acid sequence" or "polynucleotide sequence" refers to a contiguous string of nucleotide bases and in particular contexts also refers to the particular placement of nucleotide bases in relation to each other as they appear in a polynucleotide.

The terms "complementary" or "complementarity" refer to polynucleotides (i.e., a sequence of nucleotides) related by base-pairing rules. For example, the sequence "5'-AGT-3'," is complementary to the sequence "5'-ACT-3". Complementarity may be "partial," in which only some of the nucleic acids' bases are matched according to the base pairing rules, or there may be "complete" or "total" complementarity between the nucleic acids. The degree of complementarity between nucleic acid strands affects the efficiency and strength of hybridization between nucleic acid strands under defined conditions.

As used herein, the terms "hybridize" and "hybridization" are used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the Tm of the formed hybrid. "Hybridization" methods involve the annealing of one nucleic acid to another, complementary nucleic acid, i.e., a nucleic acid having a complementary nucleotide sequence.

By "under hybridization conditions" is meant conditions permitting specific hybridization. The length of the complementary sequences, the secondary structure, and GC content affects the thermal melting point Tm of the hybridization conditions necessary for obtaining specific hybridization of the target site to the target nucleic acid.

The terms "thermal melting point," "melting temperature" or "Tm" refer herein to the temperature (under defined ionic strength, pH, and nucleic acid concentration) at which 50% of probes complementary to a target hybridize to the target sequence at equilibrium (as the target sequences are present in excess, at Tm, 50% of the probes are occupied at equilibrium). In some cases, the term "Td" is used to define the temperature at which at least half of a probe dissociates from a perfectly matched target nucleic acid.

The formation of a duplex molecule with all perfectly formed hydrogen-bonds between corresponding nucleotides is referred as "matched" or "perfectly matched," and duplexes with single or several pairs of nucleotides that do not correspond are referred to as "mismatched." Any combination of single-stranded RNA or DNA molecules can form duplex molecules (DNA:DNA, DNA:RNA, RNA:DNA, or RNA:RNA) under appropriate experimental conditions.

The phrase "selectively hybridizes" or "specifically hybridizes" refers to the binding, duplexing, or hybridizing of a molecule only to a particular nucleotide sequence under stringent hybridization conditions when that sequence is present in a complex mixture (e.g. total cellular or library DNA or RNA).

Those of ordinary skill in the art will readily recognize that alternative hybridization and wash conditions can be utilized to provide conditions of similar stringency and will recognize that the combination of parameters is much more important than the measure of any single parameter.

The term "fluorophore" refers to any molecular entity that is capable of absorbing energy of a first wavelength and re-emit energy at a different second wavelength. Exemplary fluorophores include, but are not limited to CAL FLUOR® Red 610 (FR610; Biosearch Technologies, Novato, Calif.), fluorescein isothiocyanate, fluorescein, rhodamine and rhodamine derivatives, coumarin and coumarin derivatives, cyanine and cyanine derivatives, ALEXA FLUORS® (Molecular Probes, Eugene, Oreg.), DYLIGHT FLUOR® (Thermo Fisher Scientific, Waltham, Mass.), and the like.

The term "bilayer" refers to a "sandwich-like" structure composed of amphiphilic lipid molecules (often phospholipids) that are arranged as two molecular layers with the hydrophobic tails on the inside and the polar head groups on the outside surfaces.

The term "monolayer" refers to a structure defined by a molecular layer of amphipathic molecules with the head groups enriched and substantially aligned on one side and hydrophobic groups enriched and substantially on the opposite side.

The term "physiological conditions" is meant to encompass those conditions compatible with living cells, e.g., predominantly aqueous conditions of a temperature, pH, salinity, etc. that are compatible with living cells.

As used herein, the terms "determining," "measuring," and "assessing," and "assaying" are used interchangeably and include both quantitative and qualitative determinations.

The term "substantially similar" as used in the context of nucleic acid or amino acid sequence identity refers to two or more sequences which have at least about 50%, at least about 60%, at least about 70%, at least about 75%, at least about 80%, at least about 85%, at least about 90%, at least about 95%, at least about 98%, at least about 99%, or 100% sequence identity.

As used herein "% sequence identity" is determined using the EMBOSS Pairwise Alignment Algorithms tool available from The European Bioinformatics Institute (EMBL-EBI), which is part of the European Molecular Biology Laboratory (EMBL). This tool is accessible at the website located by placing "www." in front of "ebi.ac.uk/Tools/emboss/align/". This tool utilizes the Needleman-Wunsch global alignment algorithm (Needleman, S. B. and Wunsch, C. D. (1970) J. Mol. Biol. 48, 443-453; Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley. Default settings are utilized which include Gap Open: 10.0 and Gap Extend 0.5. The default matrix "Blosum62" is utilized for amino acid sequences and the default matrix "DNAfull" is utilized for nucleic acid sequences.

Throughout the present disclosure, the nomenclature used to describe the "surface-attached nucleic acids" or "membrane-anchored polynucleotides" is as follows. First, conventional names are used for certain membrane-anchored portions of the compounds, such as dialkylphosphoglycieride, and monoalkylamide. Second, for the convenience of description, the following acronyms may be utilized: FACS, Fluorescence Activated Cell Sorting; DNA, Deoxyribonucleic Acids; DIFO, Difluorocyclooctyne; NHS, N-hydroxysuccinimide; PEG, polyethylene glycol; MFI; median fold fluorescence increase; dT, deoxythymidine; MEF, mouse embryonic fibroblast; PBS, phosphate buffered saline; TEAA, triethylammonium acetate; HPLC, high pressure liquid chromatography; P/I, phorbol-12-myristate-13-acetate (PMA) and ionomycin; FITC, fluoroscein isothiocyanate.

As used herein, the term "fibers" refers to a synthetic or naturally occurring polymer (e.g., protein or glycoprotein) that is fibrillar and is mechanically actuated by action of contractile cells. The fibers may vary in length depending upon the amount of time a solution containing fibers have been allowed to anneal to yield longer fibers. Exemplary fibers include collagen and fibronectin. A matrix of fibers refers to a scaffolding of fibers that provide structural support to any cells that may be present in the matrix.

As used herein, the term "extracellular matrix" or ECM refers to a mixture of water and fibers (e.g., a polypeptide that is mechanically actuated by action of contractile cells). Fibers are organized in ECM to provide a scaffold that structurally supports any cells that may be present in the ECM.

Methods

The present disclosure provides methods for generating tissues that are programmed for folding into a three-dimensional form, where the shape of the three-dimensional form is based upon pattern of contractile cells in the tissues. The directed folding of the tissue is controlled by the position of contractile cells in the tissues. The methods include disposing a pattern of contractile cells on a surface that includes fibers that are mechanically actuated upon action of contractile cells and folding of the surface by the action of the contractile cells on the fibers. The methods also include generating a three dimensional tissue that includes a pattern of contractile cells disposed within (and optionally on the surface of) a matrix of fibers. The three dimensional tissue may be folded into various shapes based on the placement of the contractile cells within (and if present, on the surface) of the three dimensional tissue.

In certain embodiments, the present disclosure provides methods for making a planar biological tissue programmed for folding into a three-dimensional shape. The method may include patterning contractile cells on a surface of a substrate by disposing a pattern of nucleic acids on a surface of a substrate; contacting the patterned nucleic acids under hybridization conditions with a suspension of the contractile cells, where the contractile cells include cell surface-attached nucleic acids complementary to the patterned nucleic acids, and wherein the cell surface-attached nucleic acids hybridize to the patterned nucleic acids to generate patterned contractile cells on the surface of the substrate; contacting the patterned contractile cells on the surface of the substrate with a polymer matrix comprising fibers thereby embedding the patterned contractile cells into the polymer matrix; removing the polymer matrix from the surface of the substrate, where the patterned contractile cells are retained in the polymer matrix upon removal thereby generating a planar biological tissue programmed for folding into a three-dimensional shape. The method may further include culturing the planar biological tissue in a suspension culture thereby inducing folding of the planar biological tissue into the three-dimensional shape.

In certain embodiments, patterning contractile cells on a surface of a substrate may include disposing a pattern of nucleic acids on a first surface of a first substrate and a first surface of a second substrate, where the first surface of the first substrate is spaced apart from the first surface of the second substrate via a gap between the first and second substrates and where the surfaces are in a facing configuration to each other; contacting the patterned nucleic acids under hybridization conditions with a suspension of the contractile cells, where the contractile cells include cell surface-attached nucleic acids complementary to the patterned nucleic acids, and where the cell surface-attached nucleic acids hybridize to the patterned nucleic acids to generate patterned contractile cells on the first surface of the first substrate and the first surface of the second substrate; where removing the polymer matrix includes removing the polymer matrix from between the first and second substrates thereby generating a planar biological tissue with the patterned contractile cells on a top surface and a bottom surface of the planar biological tissue.

In certain embodiments, the method further includes contacting the planar biological tissue with a culture medium and incubating under cell culture conditions and folding the planar biological tissue into a three-dimensional shape. In certain embodiments, the planar biological tissue is cultured under non-adherent conditions, e.g., using a container that does not have an adherent surface, such that the planar biological tissue is free from attachment to the surface of the container. In certain embodiments, the planar biological tissue is free floating in the container holding the planar biological tissue in a culture medium.

In certain embodiments, after the planar biological tissue containing the contractile cells has been generated, regions of the polymer matrix containing the patterned contractile cells may be removed from the planar biological tissue. For example, the present methods may be used to generate a plurality of individual patterns of contractile cells on a continuous planar layer of polymer matrix. The plurality of individual patterns of contractile cells may subsequently be removed, e.g., dissected out to yield separate pieces of planar biological tissues. Dissection may be performed using any suitable method, such as, surgical tools (biopsy punch, blade, etc.) or via laser microdissection.

An exemplary system for generating a planar biological tissue configured for folding into a 3D form is depicted in FIG. 4A. The system depicted in FIG. 4A can be used to generate a planar polymer layer containing cells on a single side (one surface) of the planar polymer layer. FIG. 4B depicts removal of individual pieces of polymer layer containing patterned contractile cells from the planar biological tissue.

Another exemplary system for generating a synthetic planar biological tissue configured for folding into a 3D form is depicted in FIG. 5A. The system depicted in FIG. 5A can be used to generate a polymer layer containing cells on a first surface and a second surface opposite the first surface (e.g. a top surface and a bottom surface) of the planar polymer layer. FIG. 5B illustrates generation a plurality of individual patterns of contractile cells on a continuous planar layer of a polymer containing fibers using a method depicted in FIG. 5A. The planar polymer containing fibers and cells is removed from the flow cell shown in FIG. 5A, floated in culture medium, and regions of polymer layer containing the individual patterns of contractile cells are removed from the planar polymer layer.

In certain cases, the pattern of nucleic acid may be two-dimensional. In certain cases, the pattern of nucleic acids comprises a single population of nucleic acids having the same nucleotide sequence. In certain cases, the pattern of nucleic acids comprises two or more population of nucleic acids, wherein each population of nucleic acids comprises a unique nucleotide sequence. In certain cases, the pattern of nucleic acids comprises two or more population of nucleic acids, wherein each population of nucleic acids comprises a unique nucleotide sequence, wherein the nucleic acids of each population are uniquely addressable on the surface of the substrate. In certain cases, the pattern of nucleic acids comprises two or more population of nucleic acids, wherein each population of nucleic acids comprises a unique nucleotide sequence, wherein the nucleic acids of each population are uniquely addressable on the first surface of the first and/or second substrate. In certain cases, the disposing comprises printing a liquid comprising the nucleic acids on the substrate. Nucleic acid (oligonucleotides or polynucleotides) may be patterned on surface of a substrate prior to or after assembling the substrates to form a flow cell for generating the planar tissues programmed for folding. As such, certain embodiments of the disclosed methods include, placing a first substrate in a spaced apart manner from a second substrate, where a surface of the first substrate and/or a surface of the second substrate includes a pattern of nucleic acids disposed thereupon. The first and second substrates may be spaced apart using an elastic member that additionally facilitates sealing of a space between the substrates and the elastic member (e.g., a gasket). In certain embodiments, the method may include patterning nucleic acid on a first surface of a first substrate and a first surface of a second substrate and placing the first substrate and the second substrate in a spaced-apart manner such that the first surfaces of the substrates are in a facing orientation. The method may further include forming a seal between a periphery of the first and second substrates. One of the substrates may include one or a plurality of openings (e.g., ports) for introducing materials (e.g. cells, medium, polymer matrix, etc.) into the space between the two substrates. The method may further include incubating the patterned nucleic acids under hybridization conditions with the suspension of the contractile cells for a period of time sufficient for binding of the cells to the patterned nucleic acids. The method may optionally include a washing step to remove unbound cells. In other embodiments, a washing step may not be utilized and removal of medium containing the cells may facilitate removal of any unbound cells. In certain embodiments, the step of contacting the patterned nucleic acids under hybridization conditions with a suspension of the contractile cells may be carried out multiple times, where either the same first population of cells is introduced a plurality of times or different populations of cells (e.g., first population, a second population, a third population of cells) is contacted to the patterned nucleic acids in different contacting steps.

In certain embodiments, contacting the patterned contractile cells on the surface of the substrate with a polymer matrix containing fibers thereby embedding the patterned contractile cells into the polymer matrix may be carried out for a period of time sufficient for polymerization of the polymer matrix into a planar layer.

In certain cases, the cell surface-attached nucleic acids comprise a lipid moiety attached to a nucleic acid, which surface-attached nucleic acids are attached to the cells by insertion of the lipid moiety into the plasma membrane of the cells. In certain cases, the cell surface-attached nucleic acids comprise a spacer between the lipid moiety and the nucleic acid. The lipid moiety, in some embodiments, includes a long alkyl chain of 12-24 carbon atoms, e.g., 12-22, 12-20, 12-18, 14-22, 14-20, 14-18, 16-22, 16-20, or 16-18 carbon atoms. The spacer may include 10-80 nucleotides long, e.g., 10-60, 10-40, 20-80, 20-60, 20-40, 40-60, 40-80, 50-80, 50-80, or 60-80 nucleotides long.

Any appropriate method for patterning the nucleic acids and attaching cells to the patterned nucleic acid may be used. Exemplary methods include methods disclosed in U.S. Patent Application Publication Nos. US20140294782 and US20160010054.

In certain cases, the suspension of contractile cells comprises two or more unique populations of contractile cells, wherein each population of contractile cells comprises surface-attached nucleic acids complementary to one of the populations of nucleic acids in the pattern. Methods for patterning different types of cell populations are also disclosed in Application Publication Nos. US20140294782 and US20160010054.

Any type of contractile cells that are capable of exerting contractile force on fibers included in the polymer layer can be used. In certain cases, the contractile cells are selected from the group consisting of: fibroblasts, epithelial cells, endothelial cells, skeletal muscle cells, smooth cells, cardiac cells, progenitors thereof, and combinations thereof. In certain cases, the contractile cells are fibroblasts. In certain cases, the contractile cells are epithelial cells. In certain embodiments, the contractile cells may be isolated from a host into which the 3D biological tissue generated by the methods disclosed herein is to be transplanted. In certain embodiments, the contractile cells may be genetically engineered to increase their ability to actuate fibers, for example, increase contraction of the fibers and/or increase alignment of fibers. For example, the contractile cells express increased levels of Ras or may express constitutively active H-Ras$^{V12}$.

In certain embodiments, the method further comprises removing the polymer matrix from the three-dimensional shape to yield a tissue containing fibers and cells but substantially free of polymeric material. The polymer matrix may be removed by dissolving the polymer, e.g., by reversing the cross-linkers for polymerizing the polymer. In certain cases, the polymer may be a biodegradable polymer that may be removed by degradation in vivo after a defined period of time. Any known method for making a layer of biodegradable polymer as well as controlling degradation rates may be used. Exemplary biodegradable polymers with predetermined degradation rates are disclosed in U.S. Patent Application Publication No. US20140170204. In certain embodiments, the polymer matrix comprises methacrylate polymers, polyethylene-imine and dextran sulfate, poly(vinylsiloxane) ecopolymerepolyethyleneimine, phosphorylcholine, poly(ethyl methacrylate), polyurethane, poly(ethylene glycol), poly(lactic-glycolic acid), hydroxyapetite, poly(lactic acid), polyhydroxyvalerte and copolymers, polyhydroxybutyrate and copolymers, polycaprolactone, polydiaxanone, polyanhydrides, polycyanocrylates, poly(amino acids), poly(orthoesters), polyesters, collagen, gelatin, cellulose polymers, chitosans, and alginates or combinations thereof, hydrogels, agarose, or cellulose polymer. In certain cases, a polymer matrix that is in pre-polymer state may be introduced into a flow cell of the present disclosure (e.g., a first substrate spaced apart from a second substrate and including a port(s) for introducing materials into the flow cell) and allowed to polymerize in the flow cell. The polymer matrix may be pre-mixed with fibers or the fibers may be introduced in a separate step.

In certain cases, the polymer matrix comprises a nuclease. In certain embodiments, separating the polymer layer containing fibers and contractile cells from the substrate(s) may involve exposing the polymer layer to a nuclease to digest the oligonucleotides attaching the cells to the substrate(s). In other embodiments, separating the polymer layer containing fibers and contractile cells from the substrate(s) may not involve the use of a nuclease; rather, the hybridization of the oligonucleotides may be reversed by the cell culture conditions.

The fibers used in the present disclosure may be any fiber that is mechanically actuated upon action of contractile cells. Such fibers may include fibrilar collagen, such as type I, type II, type III, type V, or type XI collagen, or fibronectin. The fibers may be synthetic, isolated from a mammal, e.g., a rodent, a bovine, or human, or from a cell genetically engineered to express the fibers. In certain cases, the fibers may be included in an ECM. ECM used in the present disclosure may include a synthetic ECM, ECM isolated from an animal, ECM secreted from a cell line, or a mixture thereof. In certain embodiments, the polymer matrix may include polymers grafted with collagen or RGD peptide fragments.

Also disclosed herein are additional methods of generating a planar biological tissue configured for folding into a three-dimensional shape. In certain embodiments, these methods do not include a step of patterning nucleic acids on surface of a substrate and do not utilize contractile cells that include cell surface-attached nucleic acids complementary to the patterned nucleic acids. Such methods may include disposing on a substrate, a polymer layer comprising fibers; patterning contractile cells on the polymer layer such that the contractile cells are disposed in a spaced-apart manner from each other on the polymer layer; incubating the contractile cells on the polymer layer under conditions sufficient to permit adherence of the contractile cells to the polymer layer thereby generating a biological tissue configured for folding into a three-dimensional shape by action of the contractile cells on the fibers in the polymer layer.

In certain cases, the method includes generating a polymer layer and disposing fibers (e.g., ECM) on the polymer layer and disposing a pattern of contractile cells on the polymer layer.

In certain cases, the disposing comprises disposing a first layer of fibers (e.g., ECM) on a top surface of a polymer layer and disposing a second layer of fibers on a bottom surface of the polymer layer and the patterning the contractile cells comprises: patterning the contractile cells on the first layer of the fibers; incubating contractile cells on the first layer of the fibers under conditions sufficient to permit adherence of the contractile cells to the fibers; patterning the contractile cells on the second layer of the fibers; incubating contractile cells on the second layer of the fibers under conditions sufficient to permit adherence of the contractile cells to the fibers.

In certain cases, the patterning comprises printing the contractile cells in a spaced apart manner on the layer of fibers. Printing of the cells may be carried out by any suitable method, such as, 3-D printing, extrusion, extrusion 3-D printing, and the like. Any type of microfluidic nozzle or other dispensing system e.g. SCIENION™ cell printers, modified inkjet printers, droplet microfluidic devices may be used for printing cells or a solution of contractile cells and fibers (or ECM). In certain cases, the patterning comprises micro-pipetting the contractile cells in a spaced apart manner on the layer of fibers.

In certain aspects of the disclosed methods, the contractile cells may be printed in conjunction with printing of a fiber. For example, in various embodiments, contractile cells and fibers are extruded as a mixture; contractile cells and fibers are printed in layers (e.g., alternating layers of contractile cells and collagen); contractile cells and fibers are printed in separate steps to create a pattern of contractile cells adjacent a pattern of fibers, etc.

In certain embodiments, a method for generating a three-dimensional (3D) tissue configured for folding into a predetermined shape includes disposing a mixture of contractile cells and fibers on a substrate to form a 3D structure that includes the contractile cells and fibers; and incubating the structure in a culture medium under cell culture conditions for folding the structure into a predetermined shape.

In certain embodiments, the method further includes disposing a solution of fiber on the structure prior to the incubating. In certain embodiments, the method may further include repeating the disposing the mixture of contractile cells and fibers and/or solution of fibers on the structure prior to the incubating.

The structure is optionally removed from the substrate prior to the incubating or is optionally incubated with the substrate. In certain embodiments, the substrate is a flexible substrate that may also fold with the folding of the 3D structure. For example, the substrate may be a planar polymer layer or a polymer layer having a scaffold structure.

In certain embodiments, the contractile cells and the fibers are disposed using printing techniques, such as, extrusion 3-D printing. For example, in some embodiments, a solution of collagen is printed as a layer on a polymer substrate in any desired pattern to create a plurality of aligned fibers of collagen. Contractile cells are optionally included in any concentration and pattern in such a collagen layer based on the desired 3D form into which the polymer substrate is to be folded.

In certain embodiments, the method includes extruding a mixture of contractile cells and fibers within a larger 3D slab of polymer material such that the fibers form the struts within the 3D slab and the contractile cells form nodes that connect two or more struts of fibers by contracting these struts of fibers.

A solution containing fibers is either freshly prepared or may have been incubated for a period of time to form fibers of certain length. A longer incubation period is optionally used to generate longer fibers and vice versa. The concentration of fibers is determined based on the desired properties of the biological tissue.

The optimal concentration of fiber is, in some cases, determined empirically. Concentration of fibers such as, collagen, fibronectin, etc., range, in various embodiments, from 0.1 mg/ml-10 mg/ml. Higher concentration of fibers are, in some cases, used depending upon the positioning and/or number of contractile cells.

In certain embodiments, the contractile cells included in the biological tissue comprise fibroblasts. In other embodiments, the contractile cells included in the biological tissue comprise epithelial cells. In certain embodiments, the contractile cells included in the biological tissue comprise fibroblasts and epithelial cells.

In certain cases, the method further comprises incubating the biological tissue containing fibers and contractile cells in a culture medium under cell culture conditions and folding the biological tissue into a three-dimensional shape. Depending upon the method used to generate the biological tissue, the biological tissue is, in some cases, planar which is folded into a 3-D form or the biological tissue is, in some cases, in a 3-D form that is modified by introduction of folds by the action of the contractile cells on the fibers.

Exemplary embodiments of the present methods include incubating biological tissue containing fibers and a predetermined pattern of contractile cells in a culture medium while constraining a portion of the biological tissue to prevent the constrained portion from folding upon the action of the contractile cells on the fibers. The portion of the biological tissue that is under a constraint may be an edge of the tissue, a surface of the tissue, an interior region of the tissue or the like. In certain cases, more than one portion of the biological tissue may be constrained, for example, an edge and a surface may both be held under constraint.

In one example, the biological tissue may have a substantially planar surface, which planar surface may be adhered to a support to prevent the planar surface from folding upon the action of the contractile cells on the fibers. In certain embodiments, the biological tissue may be substantially planar and comprising a first planar surface opposite a second planar surface. A portion of the first planar surface or substantially the entire first planar surface may be adhered to a support to prevent the first planar surface from folding upon the action of the contractile cells on the fibers while the second planar surface undergoes folding. Such a method may be used for creating folds in a tissue in an asymmetrical manner, e. g., creating indentations on the second planar surface while the first planar surface remains substantially planar.

In another example, an edge of a biological tissue may be adhered to a support to prevent the edge from folding upon action of the contractile cells.

In certain embodiments, an interior region, an edge, or a surface of the biological tissue may include an agent that causes at least a portion of the interior region, an edge, or a surface to shrink which counteracts the contractile force and prevents the contractile cells from folding that portion. In certain embodiments, the ionic strength may be changed in a target region (e.g., an interior region, an edge, or a surface of the biological tissue) of the biological tissue causing the polymer matrix in the target region to become highly crosslinked and hence resistant to contractile forces generated by the contractile cells. In certain embodiments, ribose or lysyl oxidase may be added to a target region (e.g., an interior region, an edge, or a surface of the biological tissue) of the biological tissue which causes the target region to shrink counteracting the contractile force and preventing the contractile cells from folding the target region.

In certain cases, a portion of the biological tissue may include a swelling agent for expanding that portion thereby separating the contractile cells and/or diluting the amount of fibers such that the expanded portion does not fold. In certain examples, the swelling agent may be an agent that reverses the cross-linking of the polymer matrix. Chemical swelling of a region of the biological tissue may be performed as described in the literature, for example, Chen et al., Science, Vol. 347, Issue 6221, pp. 543-548, 2015.

In certain cases, the patterning comprises disposing a population of contractile cells comprising a single type of contractile cells. In certain cases, the patterning comprises disposing a population of contractile cells comprising a two or more types of contractile cells. In certain cases, the patterning comprises disposing a population of a first type of contractile cells in a first pattern and a population of a second type of contractile cells in a second pattern. In certain cases, the contractile cells are selected from the group consisting of: fibroblasts, epithelial cells, endothelial cells, skeletal muscle cells, smooth cells, cardiac cells, progenitors thereof, and combinations thereof. In certain cases, the polymer layer comprises hydrogels, alginate, poly-caprolactone (PCL), gelatin, agarose, cellulose polymer, or combinations thereof.

In certain cases, the ECM comprises ECM secreted from a cell line or a synthetic ECM. In certain cases, the ECM comprises fibers, such as, collagen or fibronectin.

According to certain embodiments, the nucleic acids are patterned on the surface (e.g., by molecular writing) such that after the contacting step, the cells are attached to the surface at single cell resolution. By "single cell resolution" it is meant that the cells specifically patterned on the surface (e.g., by specific binding to their orthogonal patterned nucleic acids) are physically separate from each other. That is, single cells are patterned on the surface at non-overlapping locations on the surface, where a blank space on the surface exists between the single cells. Single cell resolution is achieved, e.g., by high resolution disposal of the nucleic acids on the surface at suitable density on the surface, by selection of a suitable concentration of cells in the first suspension of cells, or the like. In other embodiments, a few cells are disposed in multiple locations in a spaced apart, for example, each location may have less than 1000 cells, less than 100 cells, less than 30 cells, or less than 10 cells, such as 2-10 cells.

In some embodiments, the spacing between cells disposed in a pattern is varied based on the desired curvature and/or contractile force exerted by the cells in the ECM. For example, to induce a greater folding the cells are optionally disposed relatively closely than to induce lesser folding. The spacing of the cells is, in some cases, determined empirically.

The cell surface-attached nucleic acids are attached to the surface of the cells by any convenient means. According to certain embodiments, the cell surface-attached nucleic acids are covalently linked to cell surface glycans via metabolic engineering and copper free click chemistry, where proteins may be modified by amine acylation. In certain aspects, the cell surface-attached nucleic acids include a lipid moiety attached (directly or indirectly) to a nucleic acid, which surface-attached nucleic acids are attached to the cells by insertion of the lipid moiety into the plasma membrane of the cells. When the cell surface-attached nucleic acids include a lipid moiety attached to a nucleic acid, in some cases, a spacer is present between the lipid moiety and the nucleic acid.

According to certain embodiments, the cell surface-attached nucleic acids are membrane-anchored polynucleotides. Examples of membrane-anchored polynucleotides are described in, e.g., Selden N S, et al. (2012) J. Am. Chem. Soc. 134, 765-768; and U.S. Patent Application Publication No. US 2014-0294782 and U.S. Patent Application No. 61/554,912, the disclosures of each of which are incorporated herein by reference. The membrane-anchored polynucleotides generally include a membrane anchored region, and a polynucleotide. The polynucleotide has a membrane proximal end, and a membrane distal end. The polynucleotide may include a linker region and a membrane distal adhesion region. A linker region of a polynucleotide may include a contiguous stretch of at least about 20 nucleotides. A membrane distal adhesion region may include at least 10 nucleotides and be positioned distal to the linker region, wherein the linker region is not hybridizable to the membrane distal adhesion region.

In some embodiments, the polynucleotide portion of a membrane-anchored polynucleotide includes DNA, e.g., single stranded DNA. In some embodiments, the polynucleotide includes RNA, PNA, LNA, or the like. In some embodiments, the polynucleotide may be single-stranded.

In some embodiments, the polynucleotide includes a linker region, where the linker region includes a contiguous stretch of about 20 to about 3000 nucleotides. In certain embodiments, the linker region is separated from the membrane distal end of the polynucleotide by about 10 nucleotides or more. For example, the linker region is optionally separated from the membrane distal end of the polynucleotide by about 10 to about 2000 nucleotides or more. In certain aspects, the polynucleotide includes a contiguous stretch of about 10 to about 2000 nucleotides including only three types of bases. In some embodiments, the three bases are selected from A, C, T, and G. In certain embodiments, the three bases are A, C, and T.

Membrane anchored polynucleotides optionally contain a membrane anchoring region, which may include an alkyl chain comprising 12-22 carbons. In certain aspects, the membrane anchoring region is attached to a polynucleotide. According to certain embodiments, the membrane anchoring region is hydrophobic. In certain aspects, the membrane anchoring region is lipophilic. In certain aspects, the entire membrane anchoring region is hydrophobic. According to certain embodiments, the entire membrane anchoring region is lipophilic. In some embodiments, only a portion is lipophilic or hydrophobic. In certain aspects, the membrane anchoring region is amphiphilic. According to certain embodiments, the membrane anchoring region is such that it is energetically more favorable for the chain to be inserted into a membrane than be contained in solution (e.g. water). In such embodiments, the membrane anchoring region spontaneously inserts into a lipid membrane.

As disclosed herein, in some embodiments, the membrane anchoring region inserts into the membrane of a cell. In some embodiments, the polynucleotide attached to the membrane anchoring region is on the extracellular side of the cell membrane. In other embodiments, the polynucleotide is on the intracellular side of the cell membrane. In some embodiments, the membrane anchoring region includes a single alkyl chain. In other embodiments, the membrane anchoring region includes two alkyl chains. In certain aspects, the membrane anchoring region comprises more than two alkyl chains. Three or more alkyl chains are optionally included.

According to certain embodiments, the membrane anchoring region comprises an alkyl chain and an alkenyl, alkyl, aryl, or aralkyl chain. This alkenyl, alkyl, aryl, or aralkyl chain may comprise 12-22 carbon atoms. In some embodiments, the alkyl chain comprises about 12-22 carbon atoms, and the alkenyl, alkyl, aryl, or aralkyl chain comprises about 12-22 carbon atoms. In some embodiments, the chains share the same number of carbon atoms. In other embodiments, one chain has between about 1 and 10 fewer carbon atoms than the other chain. In various embodiments, one chain has about 1 fewer carbon atom than the other chain, about 2 fewer carbon atoms, about 3 fewer carbon atoms, about 4 fewer carbon atoms, about 5 fewer carbon atoms, about 6 fewer carbon atoms, about 7 fewer carbon atoms, about 8 fewer carbon atoms, about 9 fewer carbon atoms, or about 10 fewer carbon atoms. In some embodiments, the membrane anchoring region comprises more than one alkenyl, aryl, or aralkyl chain, with each chain comprising 12-22 carbon atoms.

In some embodiments, the membrane anchoring region contains one or more unsaturated carbon bonds. In some embodiments, the unsaturated bonds are all contained within the same chain. In other embodiments, the unsaturated bonds may be contained in more than one chain.

In certain embodiments, the membrane anchoring region comprises a dialkylphosphoglycieride, and the polynucleotide is conjugated to the dialkylphosphoglycieride. In some embodiments, each chain of the dialkylphosphoglycieride has the same number of carbon atoms with the other chain. In other embodiments, the number of carbon atoms is different between the two alkyl chains of the dialkylphosphoglycieride. In some embodiments, each chain has between 12 to 22 carbons. In some embodiments, each chain has about 12 carbon atoms, or about 14 carbon atoms, about 16 carbon atoms, about 18 carbon atoms, about 20 carbon atoms, or about 22 carbon atoms. In some embodiments, at least one chain has about 12 carbon atoms, about 14 carbon atoms, about 16 carbon atoms, about 18 carbon atoms, about 20 carbon atoms, or about 22 carbon atoms. In particular embodiments, the membrane anchoring region comprises C16 dialkylphosphoglycieride.

In some embodiments, the membrane anchoring region comprises a monoalkylamide, and the polynucleotide is conjugated to the monoalkylamide. In some embodiments, the monoalkylamide chain has between 12 to 22 carbon atoms. In various embodiments, the monoalkylamide chain has about 12 carbon atoms, or about 14 carbon atoms, about 16 carbon atoms, about 18 carbon atoms, about 20 carbon atoms, or about 22 carbon atoms. In certain embodiments, the monoalkylamide comprises about 16 or 18 carbon atoms.

In certain aspects, the methods of the present disclosure include contacting the pattern of cells on the surface under hybridization conditions with a second suspension of cells, where cells of the second suspension include cell surface-attached nucleic acids complementary to the cell surface-attached nucleic acids of the patterned cells, and where the cell surface-attached nucleic acids of cells of the second suspension hybridize to cell surface-attached nucleic acids of the cells patterned on the surface to form a three-dimensional pattern of cells. According to certain embodiments, the cells of the second suspension are selected from epithelial cells, endothelial cells, fibroblasts, lymphocytes, stem cells, or any combination thereof.

The subject methods optionally include removing the patterned cells from the surface. In certain aspects, the patterned cells are removed by embedding the cells in a matrix, and removing the matrix from the surface, where the patterning of the cells is retained in the matrix upon removal. Matrices of interest include, but are not limited to, extracellular matrices (ECM) such as MATRIGEL®, collagen, fibrin, agarose, PEG-acrylate, and the like. The embedding, in a particular embodiment, includes filling a PDMS flow cell with liquid ECM containing high activity DNase, under conditions that maintain the gel in a liquid state (e.g. 4° C. for MATRIGEL®). The flow cell is then shifted to physiological temperatures to simultaneously trigger the gel matrix to set, and to initiate enzymatic cleavage of the DNA strands between the cells and the glass substrate. The removal optionally includes peeling the matrix containing the patterned cells off of the surface of the substrate.

In certain aspects, the methods include culturing the patterned cells. The patterned cells may be cultured under conditions such that the matrix containing the patterned cells is in a free floating form and is able to fold upon application of contractile force by the contractile cells on the ECM.

In certain embodiments, a finite element model (FEM) is optionally used to predict folds in the biological tissues disclosed herein. 1-BM is, in some cases, used to determine alignment of fibers, distance between cells, concentration of cells, and the like based on the desired 3D shape. In certain cases, the biological tissue generated using the methods disclosed herein are layered upon or sandwiched between a layer(s) of ECM that may or may not contain contractile cells. The layers of ECM, in some cases, include a different concentration of fibers and/or a type of fiber different from that present in the biological tissue.

In certain embodiments, the methods include generating multiple synthetic planar tissues and combining the planar tissues or the 3D shapes produced therefrom to form higher order structures. For example, the methods disclosed herein are, in some cases, used to generate synthetic tissues in 3D shapes such as a tube, four-fold junction with a pop-through or dimples, box, sphere, bear claw, and the like. Two or more of these synthetic 3D tissues are optionally combined to generate higher order structures. In some cases, a biological tissue produced by the methods disclosed herein is dissected to generate a desired shape and one or more dissected pieces used to generate a specifically shaped tissue.

In some embodiments, the number of cells in a cluster of cell in a pattern of contractile cells is determined based on the degree of contraction required in a particular tissue. In various embodiments, the number of cells ranges from 1-1000 cells/cluster, e.g., 3-1000, 3-300, 3-100, 5-1000, 5-300, 5-100, 8-1000, 10-100, 10-300, or 10-1000 cells/cluster. The distance between the clusters of cells is, in some cases, determined based on the of desired folding in a particular tissue and can range from 10-1000 µm, e.g., 10-300, 100-300, 100-500, 100-1000, 100-500, 200-500, 300-500, or 400-600, etc. The pattern of clustering of contractile cells is, in various embodiments, an isotropic pattern, an anisotropic pattern, or a graded pattern with respect to distance between adjacent clusters along the X- and Y-axis for a planar tissue (and X-, Y-, and Z-axis when the tissue is in a 3-D form).

The size of the tissue programmed for folding in a predetermined manner as generated using the presently disclosed methods ranges, in various embodiments, from about 1 mm-about 1 cm across the widest dimension of the tissue. In certain cases, the tissue may be larger initially and may be dissected to yield smaller pieces of tissue which may range from about 1 mm-about 5 mm across the widest dimension of the tissue.

In some embodiments, the patterning of the contractile cells is determined by the desired curvature in the folded tissue. For example, to generate a curvature of higher magnitude, contractile cells are optionally separated by a shorter distance and to generate a curvature of lower magnitude, contractile cells may be separated by a longer distance. Alternatively, or in addition, to generate a curvature of higher magnitude, higher numbers of contractile cells are optionally patterned and to generate a curvature of lower magnitude, lower numbers of contractile cells may be patterned. Similarly, in order to generate sharper folds (higher curvature), a contractile cell (e.g., a fibroblast) that actuates increased contraction of fibers and/or increased alignment of fibers are optionally used. In order to generate smoother folds (lower curvature), a contractile cell (e.g., a epithelial cells) that actuates contraction of fibers and/or alignment of fibers at a lower level are optionally used.

In embodiments where it is desired to introduce opposite folds in a tissue, the contractile cells are optionally patterned to introduce such folds. For example, in some embodiments, the contractile cells are patterned on a first surface and on a second surface of a planar substrate (e.g., a polymer layer containing fibers), where the first and second surfaces are opposite to one another. The pattern of contractile cells on the first surface are optionally offset from the pattern of contractile cells on the second surface. In some cases, the distance of the offset is determined by the desired distance between the folds. In some cases, the number of cells disposed on the first and second surfaces is determined by the desired curvature of the folds. In certain embodiments, the number of cells on the first and second surfaces is approximately the same. In certain embodiments, the number of cells on the first and second surfaces may not differ by more than 25%.

In certain embodiments, the method includes introducing folds that alternate in polarity across an x-axis of the tissue (e.g., a corrugated structure). In such embodiments, the number of cells that produce each fold may not differ by more than 25%.

In certain embodiments, the method includes producing a planar tissue configured for folding into a tube shape. For example, in some embodiments, the method includes patterning contractile cells on a polymer layer with fibers, where the contractile cells are patterned along the x axis of the polymer layer using log-distributed cell spacings in the x direction from 30 to 1000 microns (e.g., 30 to 300 microns, 100 to 300 microns, 100 to 250 microns, 30 to 250 microns, 50 to 250 microns, 100 to 250 microns, 50 to 150 microns, or 80 to 250 microns). The tissue spacing along y is optionally kept relatively large (e.g., at about 3000-300 microns, such as, 2500-300 microns, 1000-300 microns, 500-300 microns, or 400-300 microns) in order to minimize curvature along the length of the tube. In certain cases, the spacing of cells in the x direction is in the range of 100 to 300 microns or 80 to 250 microns and along the y axis may be 500-300 microns or 400-300 microns.

Systems

The present disclosure also provides systems which find use, e.g., in practicing the subject methods. In certain cases, a system for generating a synthetic planar biological tissue configured for folding into a three-dimensional shape is provided. For example, in some embodiments, the system includes a population of nucleic acids disposed in a pattern on a surface of the substrate; a population of contractile cells comprising cell surface-attached nucleic acids complementary to the population of nucleic acids, wherein the population of cells is attached to the population of nucleic acids by hybridization of the surface-attached nucleic acids to the population of nucleic acids; and a polymer matrix comprising extracellular matrix.

In certain cases, the system comprises a first substrate spaced apart from a second substrate, wherein a first surface of the first substrate is in a facing configuration to a first surface of the second substrate, wherein a population of nucleic acids is disposed in a pattern on the first surfaces of the first and second substrates.

In certain cases, another system for generating a synthetic planar biological tissue configured for folding into a three-dimensional shape is disclosed. The system comprising: a polymer layer comprising a layer of fibers (e.g., extracellular matrix) disposed on a surface of the polymer layer; and a population of contractile cells.

In certain cases, another system for generating a synthetic planar biological tissue configured for folding into a three-dimensional shape is disclosed. The system comprising: a polymer layer comprising a layer of fibers (e.g., extracellular matrix) disposed on a top surface and a bottom surface of the polymer layer; and a population of contractile cells.

In certain cases, the population of contractile cells comprises a cell type selected from the group consisting of: fibroblasts, epithelial cells, endothelial cells, skeletal muscle cells, smooth cells, cardiac cells, progenitors thereof, and combinations thereof.

In certain cases, the polymer comprises hydrogels, alginate, poly-caprolactone (PCL), gelatin, agarose, or cellulose polymer. In certain cases, the ECM may include fibers actuable by contractile cells. In certain cases, the fibers comprise collagen and/or fibronectin.

In certain cases, the system includes programming that includes instructions that when executed by the processor of a computer causes the computer to perform the method of generating a tissue configured for folding in a pre-determined manner.

The programming is optionally embodied in a computer readable medium and/or stored in a cloud. In some embodiments, the programming is provided independently of other components for generating a tissue configured for folding in a pre-determined manner. In certain cases, the programming is bundled together with the other components for generating a tissue configured for folding in a pre-determined manner.

In certain cases, the programming includes an algorithm for calculating the pattern of the contractile cells, the number of contractile cells, the concentration of fibers, and the like needed to generate a tissue that will fold in a desired structure. For example, the programming may provide instructions to a robot or a user to dispose the cells at particular numbers and in particular pattern to generate a tissue that will fold into a tube, a corrugated sheet, and the like. In embodiments utilizing automated or semi-automated instruments for generating a tissue configured for folding in a pre-determined manner, the programming provides instructions to the instruments to carry out one, more, or all steps of the methods disclosed herein.

In Vitro Generated Biological Tissue

An engineered three-dimensional (3D) biological tissue comprising a pre-determined pattern of contractile cells, where the pre-determined pattern of contractile cells determines the shape of the 3D biological tissue is also disclosed. In certain cases, the biological tissue is generated from the methods and systems described herein. The term engineered 3D biological tissue refers to an artificial, non-naturally occurring tissue that includes a pre-determined pattern of contractile cells, which contractile cells have been positioned according to supplied instructions for obtaining a tissue of a certain shape. The methodology disclosed herein provides precise placement of contractile cells in relation to each other in order to generate a tissue with a pre-determined shape. In certain cases, the clusters of contractile cells may be spaced apart by the same distance. In other cases, the clusters of contractile cells may be spaced apart by a distance that increases by a set increment along one or more axis. In some cases, the clusters of contractile cells may be spaced apart by a distance that increases exponentially along one or more axis. In certain cases, the cells may be programmed to self-organize, for example, using their physical properties or synthetic biology techniques.

The tissue generated by the disclosed methods can be substantially identical in terms of size, shape, and pattern of cells present in the tissue. The generation of substantially identical tissue is advantageous in methods that require uniformity across different conditions. For example, multiple different engineered 3D biological tissues generated by the present methods may be identical and hence can be used in screen for agents that affect these tissues. In certain cases, multiple identical engineered 3D biological tissues may be used to screen for agents that modulate cell signaling, morphogenesis, organ formation, living system organization and the like. These tissue do not suffer from the variations in cell numbers and organization that are inherent in isolated biological tissue or even those generated in vitro using a cell culture system.

In certain cases, the biological tissue comprises only one type of contractile cells. In certain cases, the biological tissue comprises only two types of contractile cells. In certain embodiments, the one type of contractile cells comprise fibroblasts. In certain embodiments, the two types of contractile cells comprise fibroblasts and epithelial cells.

In certain cases, the pattern of biological tissue comprises spaced-apart clusters of contractile cells. In some embodiments, each cluster comprises 5-100 contractile cells. In some examples, each cluster comprises 5-50 contractile cells. In yet other aspects, each cluster comprises 5-10 contractile cells. In some cases, the biological tissue includes a pre-determined concentration of fibers. In some embodiments, the biological tissue is devoid of one or more of blood cells, adipocytes, and nerve cells. In certain embodiments, the biological tissue is devoid of one or more of red blood cells and immune cells. In certain embodiments, the biological tissue is devoid of one or more of immune cells, such as, lymphocytes, basophils, neutrophils, eosinophils, monocytes and macrophages.

The engineered 3D biological tissue generated by the methods of the present disclosure is distinct from a biological tissue isolated from an animal, e.g., a human, in many aspects. As noted herein, the engineered 3D biological tissue is devoid of immune cells that are normally present in vivo in tissues. In addition, the engineered 3D biological tissue disclosed herein is devoid of a vascular network of channels/tubes and the like that are present in a naturally formed tissue-such as blood vascular network, lymphatic vascular network, and the like. In certain embodiments, the engineered 3D biological tissue generated by the methods of the present disclosure may be further modified by addition of immune cells and/or vascular network of channels/tubes in order to serve as a model for a biological tissue isolated from an animal.

In some aspects, the contractile cells are selected from the group consisting of: fibroblasts, epithelial cells, endothelial cells, skeletal muscle cells, smooth cells, cardiac cells, progenitors thereof, and combinations thereof.

In some aspects, the engineered 3D biological tissue can include a matrix of hydrogel, gelatin, alginate, poly-caprolactone (PCL), agarose, cellulose, or another polymer to support the fibers which may be collagen or fibronectin. Collagen may be synthetic or obtained from a biological source.

In certain cases, the biological tissue may be a hybrid tissue comprising separate units of in vitro generated biological tissue. The separate units of in vitro generated biological tissue may be assembled to provide a hybrid tissue, for example, the separate units of in vitro generated biological tissue may be layered one on top of another. The separate units of in vitro generated biological tissue may have different types of cells, e.g., a first unit may have epithelial cells and a second unit may have fibroblasts.

In certain cases, the hybrid tissue may include in vitro generated biological tissue and biological tissue isolated from a mammal. For example, the hybrid tissue may include a first unit of an in vitro generated tissue (e.g., a layer of epithelial cells and/or fibroblasts) and a layer of biological tissue isolated from a mammal. Biological tissue isolated from a mammal that can be used to generate hybrid tissues include blood vessels, adipose tissue, nerve tissue and the like.

Utility

The methods, substrates, polymer layers, and systems of the present disclosure find use in a variety of different applications, including research, pre-clinical, and clinical applications. For example, the 3D cellular structures generated using the methods of the present disclosure are useful as models of, e.g., skin, gut, prostate, liver, and breast. Such tissue/organ models are useful for molecule efficacy and toxicity testing, e.g., drug or cosmetics testing.

The methods, substrates, polymer layers, and systems of the present disclosure find use in production of synthetic organoids for implantation into animals and humans e g to replace pancreatic function in diabetes, or in the context of implantable bioreactors such as to replace kidney function. Other uses include production of synthetic biological materials by leveraging tissue self-assembly, ECM secretion e.g. synthetic leathers, natural chemical products, food products.

The folded tissues disclosed here are also useful for model systems for testing cell signaling, deciphering mechanisms involved in morphogenesis, organ formation, living system organization and the like.

Moreover, the methods, substrates, and systems find use in clinical applications. For example, the methods of the present disclosure are useful in regenerative medicine applications where it is desirable to generate 3D tissues or substructures thereof for purposes of providing such tissues or substructures thereof to a subject (e.g., a human patient) in need thereof, e.g., due to the subject lacking a functional corresponding tissue or tissue substructure.

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, dimensions, etc.) but some experimental errors and deviations should be accounted for.

Materials and Methods

Cell Culture.

Mouse embryonic fibroblast (MEFs, gift of Jay Debnath, UCSF), MCF10AT (Liu, J. S., et al., *Cell Reports* 2, 1461-1470 (2012)) (RAS cells, bulk population and clones) expressing H2B-GFP and constitutively active H-Ras$^{v12}$, human umbilical vein endothelial cells (HUVECs, Lonza) expressing mCherry after transduction with lentivirus made with pSicoR-Efla-mCh-Puro (Addgene 31845), human mammary fibroblasts (gift of Jim Garbe, UCSF) expressing maxGFP via pSicoR-Efla-maxGFP-Puro (gift of Justin Farlow, UCSF), Madin-Darby canine kidney epithelial cells (MDCK, UCSF cell culture facility), Jurkat immortalized T-cells (American Type Culture Collection), primary human mammary epithelial cells (HMECs, gift of Jim Garbe, UCSF), and Caco2 human epithelial colorectal adenocarcinoma cells (UCSF cell culture facility) were cultured on treated polystyrene plates and flasks (Corning). RAS cells were cultured as previously described for MCF10A cells (Debnath, J., et al., *Methods* 30, 256-268 (2003)). HUVECs were maintained in EGM-2 medium (Lonza). Jurkat cells were maintained in Roswell Park Memorial Institute (RPMI) medium with 10% fetal bovine serum (FBS). MDCKs and Caco2 cells were maintained in Dulbecco's modified Eagle's medium (DMEM) with 10% FBS and 1× non-essential amino acids. HMECs were maintained in M87A medium and sorted at passage 4 into myoepithelial (MEP) and luminal (LEP) epithelial populations as previously described (Stampfer, M. R., et al., *Cell and Molecular Biology of Breast Cancer* (ed. Schatten, H.) 323-361 (Humana Press, 2013). doi:10.1007/978-1-62703-634-4_15).

Blebbistatin (Abcam ab120491) and staurosporine (Sigma-Aldrich S5921) were added to cell media at the indicated concentrations by serial dilution from 10 mM DMSO stocks.

Reconstituted Tissue Fabrication.

Flow cells were constructed by sandwiching aldehyde-silanized glass slides (Schott 1064874) against a PDMS membrane gasket (0.01" thick, SSP M823) cut with a craft cutter (Silhouette). Through-holes in the top slide were made using 10-20 passes of an etching laser at 15% power (VLS3.5, Universal Laser Systems). Fiducial marks were etched into both glass slides to aid alignment by light microscopy before cell patterning. Etched slides were used as substrates for DNA-programmed assembly of cells (DPAC), as detailed previously (Todhunter, M. E. et al. *Nat Meth* 12, 975-981 (2015)). After etching, amine-modified oligonucleotides were printed onto the slides and covalently attached by reductive amination. Printing locations were specified in bitmap files. Slides were treated with hydrophobic silane and blocked by protein adsorption before being assembled against the PDMS gasket Immediately prior to sandwiching, PBS was added to gaps in the gasket to prime flow cells and reduce the tendency to trap bubbles between the slides. Slight pressure was applied to the sandwich using a microarray hybridization cassette (AHC1X16, ArrayIt). The positions of through-holes in the top glass slide and voids in the PDMS gasket were matched to the dimensions of the cassette such that 16 flow cells could be independently addressed through pairs of through-holes).

Cells to be assembled on the top and bottom flow cell walls were lifted from plates using PBS followed by 0.05% trypsin and labelled with lipid-modified oligonucleotides as previously described (Todhunter, M. E. et al. *Nat Meth* 12, 975-981 (2015)) (with the exception of Caco2 in one instance, see below). With the flow cell cassette on ice, cells in suspensions of ~10×10$^6$ cells/ml were introduced to flow cells by gentle pipetting on top of one of the pair of through-holes and adhered to DNA spots on the glass. A further round of cellular assembly was used to generate clusters of 5-8 cells at each DNA spot. After cell patterning, a liquid ECM-mimetic gel precursor was introduced in two aliquots of 20 µl per flow cell and the cassette placed at 37° C. for 20 min to set the precursor. Reconstituted tissue gels consists of a composite of fluorescently-labeled collagen 1 fibers in MATRIGEL®. Firstly, 200 µl of ~8.5 mg/ml rat tail collagen 1 in 0.02M acetic acid (Corning 354249) was labeled using 5 µl 1 mg/ml Alexa Fluor 555 or 647-NHS ester in DMSO (ThermoFisher Scientific; depending on imaging requirements) added immediately prior to neutralization with 10 µl 20×PBS and 4 µl 3M NaOH on ice. After 10 min on ice, 70 µl of this collagen stock was added to a second stock consisting of 415 µl of ~9 mg/ml MATRIGEL® (Corning 354234) and 15 µl of Turbo DNase (ThermoFisher Scientific AM2238). This 500 µl precursor solution was sufficient to fill 8-10 flow cells.

The flow cell cassette was then disassembled gently, and the slide sandwich submerged in the appropriate cell media at room temperature. A razor blade was used to gently pry apart the glass slides. Reconstituted tissue consisting of cell clusters carried along with the ECM gel typically floated spontaneously into the media or could be gently detached from one of the glass slides with a micro-spatula (Fine Science Tools 110089-11). Floating tissues were then manually cut out either using a biopsy punch or razor blade, or by laser microdissection (Zeiss PALM MicroBeam). Finished tissues were transferred to glass coverslip-bottomed 24-well plates (Greiner) using a P1000 pipet trimmed to a ~7 mm diameter. If reconstituted tissues were intended to undergo folding, the glass in each well was coated with 1% agarose in PBS prior to adding reconstituted tissues to prevent them from adhering. For imaging studies of collagen strain/alignment and non-folding controls, or prior to microdissection, reconstituted tissues were encouraged to adhere to the bottom of coverslip wells by 10 min 37° C. incubation in a semi-dry state (with media temporarily withdrawn).

Rather than being assembled by DPAC, a semi-confluent layer of Caco2 cells was built at the lower tissue surface by pre-mixing them at 4×10$^6$ cells/ml in gel precursor such that they settled onto the bottom of the flow cell prior to setting at 37° C.

Reconstituted tissues that contained HUVECs were cultured in EGM-2 with 200 ng/ml each of IL-3, stromal-cell derived factor 1a (SDF-1a) and stem-cell factor (SCF) to encourage lumenization. Tissues with a single passenger cell type were cultured for 12 hours in the appropriate fibroblast medium, and transferred to the passenger cell type's medium thereafter. 3-cell type reconstituted tissues (containing MEFs, HUVECs, and Caco2 cells) were similarly transferred to 50:50 HUVEC:Caco2 media after 12 hours.

Cell printing. Rather than using DPAC, gels produced in flow cells could be patterned with cell clusters using non-contact printing. A 10×106 cells/ml MEF suspension in PBS was distributed using the sciFlexArrayer S3 (Scienion Technologies), a piezoelectric small-volume dispenser. Expelled drops of cell suspension were approximately 300 pL in volume and 100 µm in diameter, and contained an average of 3 cells/drop. Reconstituted tissues were adhered to a plain glass slide in the semi-dry state during printing. Afterwards, tissues were incubated at 37° C. for 30 min to encourage cell adhesion, and then gently lifted off the slide using a micro-spatula after adding excess cell culture media.

Droplet Contraction.

Rapid screening for cell contractility was done by setting 1 µl droplets of ECM gel containing 10$^6$ cells/ml on coverslip-bottomed microwells at 37° C. for 20 min. Media was then added and droplets detached by gentle pipetting prior to time lapse imaging.

Reconstituted Tissues Gel Characterization.

Reconstituted tissues gel strain in the vicinity of single cells was determined by particle image velocimetry (PIV ImageJ plugin (Tseng, Q. et al. *Proc. Natl. Acad. Sci. U.S.A.* 109, 1506-1511 (2012)). 30 µl aliquots of reconstituted tissues gel precursor with 1 micron red fluorescent polystyrene beads at 8×10$^6$ per ml (ThermoFisher Scientific F13083) and unlabeled collagen fibers were set in wells of a 96-well plate at 37° C. for 20 min. 3,000 cells per well were settled on the reconstituted tissue gel underlay and imaged every 60 min by confocal microscopy for bead displacement.

Collagen fiber orientation and FEM edge orientation were measured using OrientationJ in ImageJ (Püspöki, Z., et al., in *Focus on Bio-Image Informatics* 219, 69-93 (Springer International Publishing, 2016). Orientation images were smoothed using Gaussian blur on a length-scale of ~0.1 times the cell cluster spacing to enable interpretation.

Collagen strap orientation was determined in ImageJ by manual annotation. Straps that had collagen fluorescence at a signal-to-noise ratio of at least 3 were included in orientation plots.

Gel rebound was measured 30 min after ablation of ~100 µm×10 µm tracks by laser microdissection (Zeiss PALM MicroBeam). Laser power was adjusted in control regions distant from cell clusters to ensure cutting through the entire gel thickness.

Imaging.

3D time lapses of reconstituted tissue folding were recorded at 37° C. and 5% $CO_2$ with a 10× objective via tiled confocal microscopy through Zeiss Zen 2012 software with 30 micron z slice spacing using a Zeiss Observer.Z1 with a Yokogawa CSUX1 spinning disk and Photometrics Evolve 512 EMCCD camera.

Spatial Reconstruction of Reconstituted Tissues from Confocal Data.

Confocal images were segmented in ImageJ either manually or by semi-automated thresholding. Binary image stacks were then read into MATLAB (MathWorks) and converted to isosurface meshes via marching cubes. Meshes were smoothed and face colors assigned to local curvatures using custom scripts.

Curvatures reported for cap reconstituted tissues were generated by radially reslicing and thresholding in ImageJ after manually picking the center of reconstituted tissues to serve as origin points. Radial slices were read into MATLAB and least-squares fitted to circles. Anisotropic curvatures were similarly generated for the indicated cutting planes and folds.

Immunofluorescence.

Reconstituted tissues were transferred to a fresh 24-well plate and fixed in 2% paraformaldehyde for 45 min at room temperature. All liquid handling was done while observing reconstituted tissues by light microscopy to avoid mechanical disruption with the pipet tip. Reconstituted tissues were washed three times with 100 mM glycine in PBS for 20 min per wash and permeabilized in 0.5% Triton X-100 in PBS for 15 min, all at room temperature; and blocked overnight at 4° C. in 0.1% bovine serum albumin, 0.2% Triton X-100, 0.04% Tween-20, 10% goat serum (ThermoFisher Scientific 16210064) including a 1:50 dilution of goat anti-mouse IgG fab fragment (Jackson ImmunoResearch 115-007-003) in PBS. Reconstituted tissues were probed with primary antibodies in blocking buffer overnight at 4° C. and washed three times for 1 hour per wash in blocking buffer. This process was repeated for secondary antibodies. Reconstituted tissues were then imaged in FocusClear (CedarLane FC-101). Primary antibodies were rabbit anti-human cytokeratin 14 (1:50, ThermoFisher Scientific RB-9020-P) and mouse anti-human cytokeratin 19 (1:50, Biolegend 628502). Secondary antibodies were AlexaFluor 647-labeled goat anti-mouse IgG and AlexaFluor 405-labeled goat anti-rabbit IgG (1:200, ThermoFisher Scientific A21235 and A31556 respectively).

Chick Gut Imaging.

Fertilized white Leghorn chicken eggs were incubated, windowed, and otherwise handled as previously described (Schneider, 1999). Embryos were dissected at the indicated embryonic day to remove the gut tube. Tubes were cut into rough 2 mm segments and then longitudinally to expose the luminal surface. Tissues were fixed in 4% paraformaldehyde, washed 3 times in PBS for 5 min per wash, stained in 2 µg/ml ethidium bromide in PBS for 15 min, and washed similarly, all at room temperature (Eames and Schneider, 2005). The luminal surface was imaged using a macro confocal microscope (Nikon AZ-C2Si) at 2× magnification.

Finite Element Modeling.

Reconstituted tissues were modeled using Kangaroo2, a position-based dynamics solver within the Rhino Grasshopper algorithmic modeling environment. We took a relatively abstract form-finding FEM approach to enable interactive, rapid reconstituted tissue prototyping. Cuboidal unit cells were constructed from quad mesh faces with two diagonals per quad. Unit cells were assembled to model reconstituted tissues at a scale of 0.1 mm per unit edge length, balancing spatial resolution and simulation time. All edges were modeled as linear elastic elements with stiffness $k_1$ and rest lengths equal to their initial lengths. Since tissue positions were specified at 10× higher resolution than mesh vertices in the model, actuator nodes to be specified on the upper or lower model faces were generated by rescaling and rounding DPAC tissue coordinates (no attempt was made to correct spatial aliasing artifacts). The edges in the xy plane coincident with these nodes were specified as active edges with a >3×-higher spring constant $k_2$ relative to other edges in the spring network, and with rest length s manipulated by the user.

Models constructed in this way thus had two parameters—the stiffness of non-active edges $k_1$, and the active edge rest length s. $k_1$ was fitted by manually iterating it for s=0 to approximate the curvature data of d=100 micron caps at t ~21 hours. This value of $k_1$ was then used for all subsequent simulations. Reconstituted tissues were typically simulated for 10 values of s in the range of 0-1 to produce a family of objects at intermediate folding states for each reconstituted tissue design. Model reconstituted tissues were baked and exported from Rhino, remeshed in Zbrush (Plxologic) to remove mesh face orientation defects, read into MATLAB, voxelized, converted to isosurface meshes, smoothed and face colors mapped to local curvatures using custom scripts.

Since s is not directly analogous to reconstituted tissue folding time in vitro, model reconstituted tissues were chosen based on qualitative similarity in curvature distributions to experiment reconstituted tissues from the corresponding imaging time points.

Statistical Analysis.

Data were analyzed for statistically significant differences between sample means via ordinary one-way ANOVA with Holm-Sidak's multiple comparisons test in Prism 7 (GraphPad).

Inferring Tension from Local Retraction after Ablation in Reconstituted Tissues.

Since real-time imaging of retraction at the gel surface was limited by a mismatch in the appropriate length-scales of cutting and confocal microscopy, we made dissections and imaged resulting incisions after approximately 30 min. After 30 min, we expected that strain due to elastic tissue rebound would be fully realized (Bonnet et al., 2012), while continued strain due to active pulling at cell clusters would be limited to less than ~10 µm along collagen straps (FIG. 11C). We consider ablation of tissues to be analogous to severing an elastic spring under tension, discarding time dependent dynamics from the Kelvin-Voigt model typically used to study viscoelastic retraction in live biological contexts (Bonnet et al., 2012; Kumar et al., 2006; Tanner et al., 2010). Therefore, the pre-tension force orthogonal to an ablated incision $F \propto (L-L_o)$, where L is the relaxed incision width at the gel surface after ablation, and $L_o$ is the width of gel immediately destroyed by laser irradiation (in practice, the laser beam width or the incision width in control gels lacking cell clusters).

Scaling Analysis of Isotropic Reconstituted Tissue Curvature.

We approximate reconstituted tissues as synclastic elastic plates, such that for small curvatures (deflections smaller than plate thickness), the strain in the yz plane at an arbitrary vertical distance z from the midplane of the plate is given by:

$$\varepsilon_{yz} = zC_{yz} \quad [1]$$

where $C_{yz}$ is the curvature of the midplane parallel to the yz plane (Timoshenko and Woinowsky-Krieger, 1959). We assume that arrays of isotropic actuators on reconstituted tissues generate spatially homogeneous strains tangential to gel surfaces at a given timepoint t in proportion to their total number $N_c$ such that:

$$\varepsilon_{yz} \sim N_c \dot{\varepsilon}_{yz} t \qquad [2]$$

where $\dot{\varepsilon}_{yz}$ is the collagen matrix strain rate of a cell cluster. Experimentally measured values of $\dot{\varepsilon}_{yz}$ appear to be approximately constant over time for large ranges in local and global collagen gel deformation (Meshel et al., 2005). Thus, combining [1] and [2] suggests a first-order model of the form $C_{yz} \propto N_c$ to fit calibration data describing folding of isotropic reconstituted tissues at intermediate time-points.

Fidelity of Anisotropic Folds.

We hypothesized that cell-type specific differences in migration rate would predict the fidelity with which initial cluster positions encode anisotropic curvatures. We found that mesenchymal-like carcinoma cells (MCCs) migrated to a characteristic distance of half the cluster pair spacing d/2 of 80 μm in a characteristic time Td/2 of 7.5 hr, while mouse embryonic fibroblasts (MEFs) reached this threshold in 11 hr (FIG. 14C). Because the folding times for isotropic reconstituted tissues with grids of similar spacing were approximately 10 hr and 5 hr for MCC and MEF cell types, respectively, these data suggest that MCC clusters disperse from their initial positions before significant folding occurs, whereas MEFs do not. This dispersal of cells away from their intended positions during folding would tend to produce spatially uncontrolled strains, and thus uncontrolled curvatures. To further investigate this hypothesis, we measured the angle at which tensile collagen straps formed between clusters (relative to the horizontal axis) in isotropic or highly anisotropic grids (FIG. 14D). At 9 hours in culture, straps between clusters were primarily oriented towards nearest neighbors along 0 and 90 degree angles in isotropic grids, regardless of cell type. At 15 hours, however, strap orientation had become randomly distributed due to the disorganizing effect of cell migration away from initial cluster positions.

For anisotropic grids, straps between clusters were also primarily oriented towards nearest neighbors at 9 hr, focused at $0_o$ along the horizontal axis. At 15 hours, however, straps were more frequently oriented away from this axis (i.e. were more disorganized) in anisotropic MCC grids when compared to MEF grids, consistent with extensive MCC migration away from initial cluster positions. These data suggest that a threshold in the ratio of cell strain rate to migration rate determines the extent to which a given cell type actuates reconstituted tissues with sufficient fidelity.

Robustness of Adjacent Opposing Folds to Pop-Through.

Figure 18:
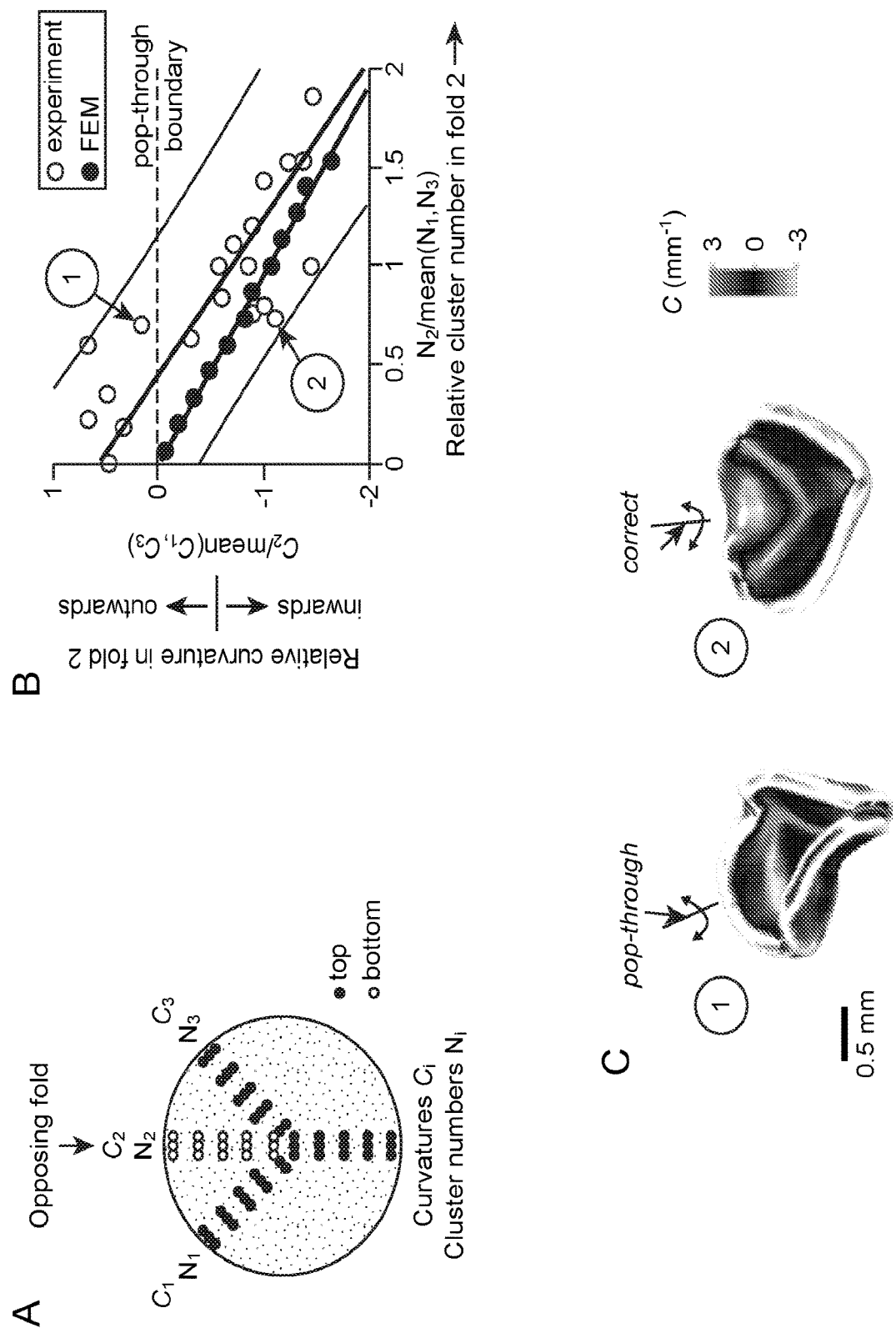
FIG. 18 illustrates that opposing folds in reconstituted tissues are robust to pop-through defects.

Of central concern for the design of adjacent folds of alternating negative and positive curvature (i.e. opposing folds) is their robustness to "pop-through" defects, in which out of plane deformations can emerge in the unintended orientation. Opposing folds can be built by placing cell clusters on opposite sides of the ECM sheet at spatially distinct regions in the xy plane. To study the robustness of our reconstituted tissues to such defects, we built four-fold vertex tissues that have three folds of the same orientation and one in the opposite orientation that converge at a single point. We hypothesized that for opposing folds to form successfully, they would need to be actuated by similar numbers of cell clusters so that the orientation of a particular fold would not be determined by a more radically curved neighboring fold. Indeed, a critical threshold at which the opposing fold formed in the incorrect orientation emerged when the number of clusters in the opposing fold was less than around half the average number in the two adjacent folds (FIG. 18). However, for values of this ratio above ~0.75, the opposing fold always popped into the correct orientation, demonstrating that adjacent opposing folds form robustly if spatial strain profiles are properly managed.

Modulation of Passenger Cell Behavior.

HUVEC cells patterned as a patch at the intersection of 3 folds in fourfold vertex reconstituted tissues migrated preferentially along nascent folds in comparison to non-folding control tissues (FIG. 20), perhaps responding to local collagen concentration and/or alignment orchestrated by fibroblasts at folds. These data suggest that reconstituted tissues can incorporate cells that generate the matrix strains and alignments necessary for folding, as well as other cell types that respond dynamically to these microenvironmental cues as folding progresses.

Example 1: Directed Folding of Tissues Via Programmed Cellular Contractility

Efforts to engineer curvature into thin polymer layers often depend on developing in-plane stresses due to differential contraction or swelling in the material, which can be relieved by curvature and buckling deformations that are at least partially predictable. These out-of-plane deformations can be further controlled by elaborating sheets with hinges or by using anisotropic material properties to bias curvature along prescribed directions.

Although significant engineering control has been achieved in abiotic systems, progress towards building folded biological tissues has been limited firstly by incomplete knowledge of how cells generate and respond to mechanical forces in their microenvironment. Secondly, the emergence of curvature and folding in response to such forces has suffered from a lack of tissue-mimetic model systems that afford engineering control over parameters such as cell type and distribution, and ECM stiffness and composition. To address these challenges, we study force generation between contractile tissues embedded at the surface of uniform ECM gels, and use patterned contractile networks to study the subsequent out-of-plane curvatures.

Figure 8:
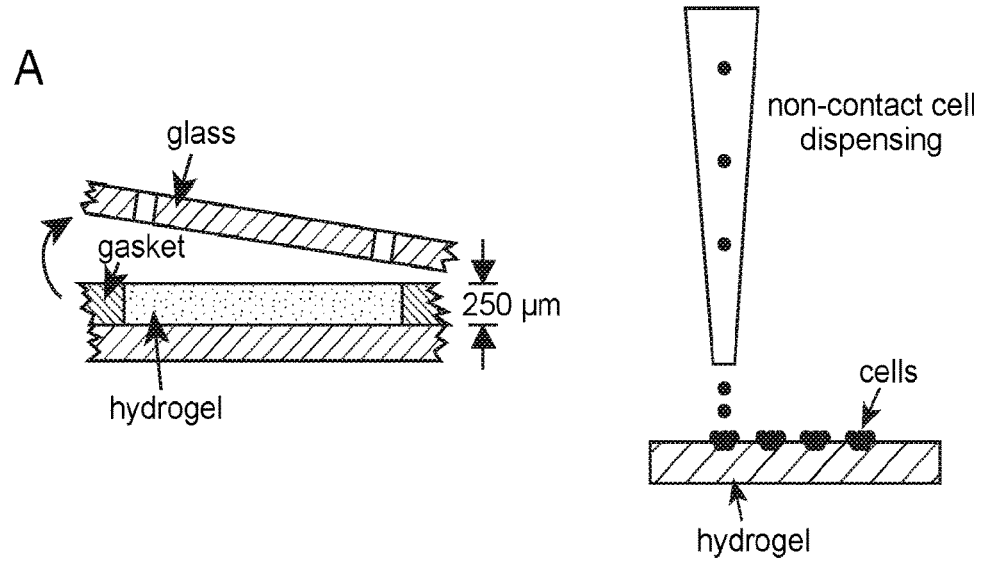
FIG. 8 illustrates reconstituted tissue fabrication by non-contact cell printing.
Figure 8:
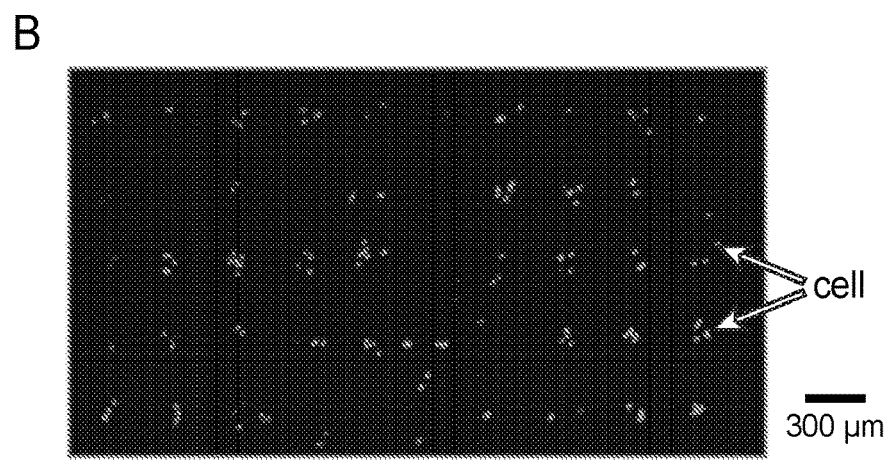
Figure 8:
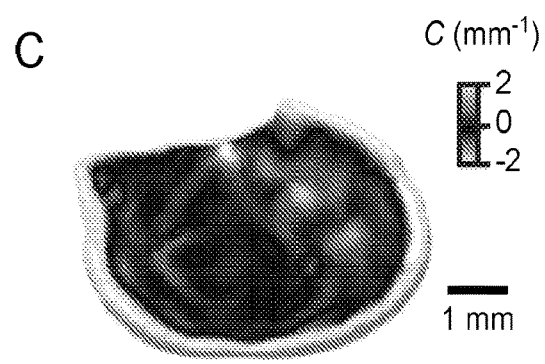
Figure 9:
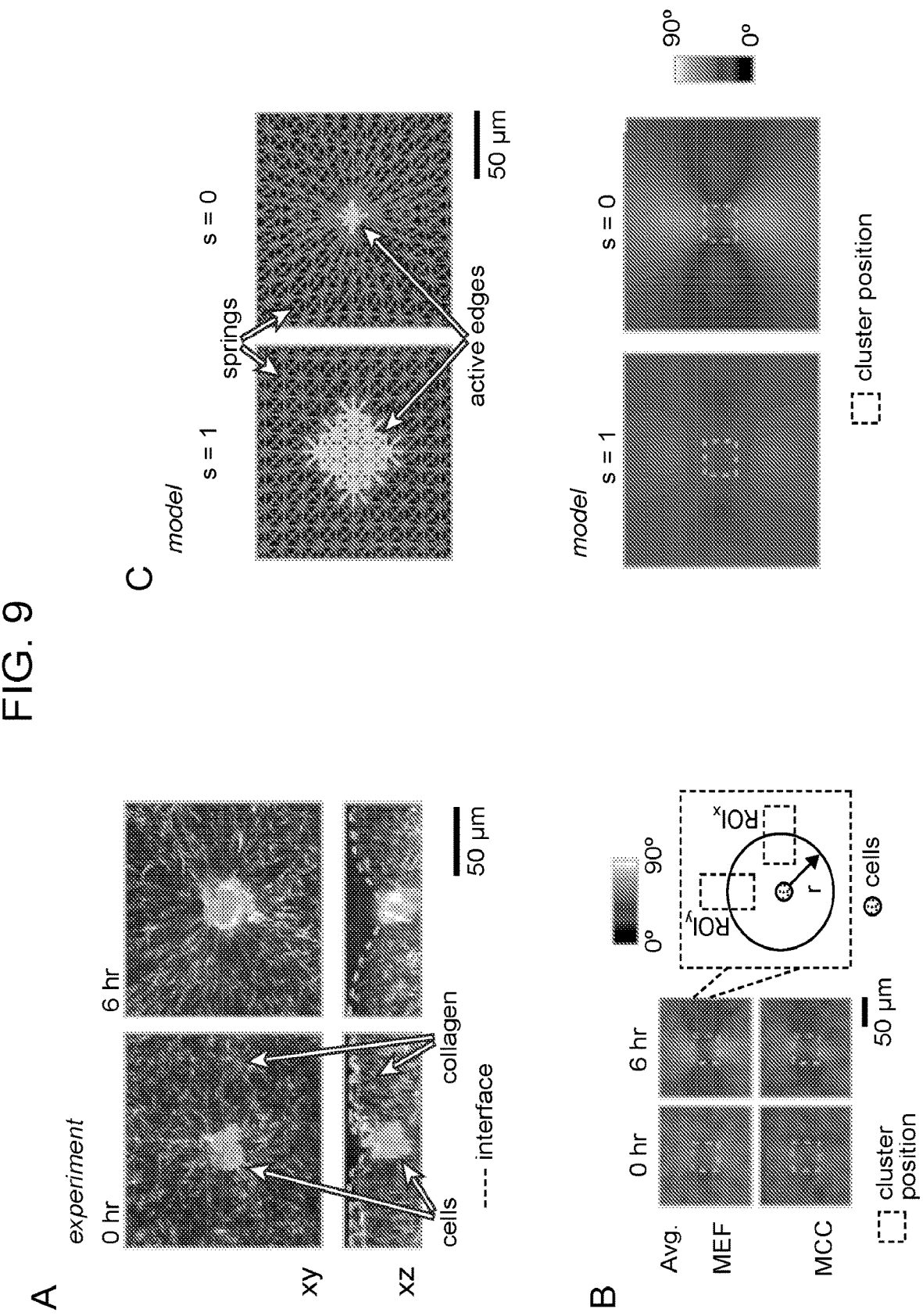
FIG. 9 illustrates that cell clusters are isotropic attractors that radially align collagen at rates dependent on cell type.
Figure 9:
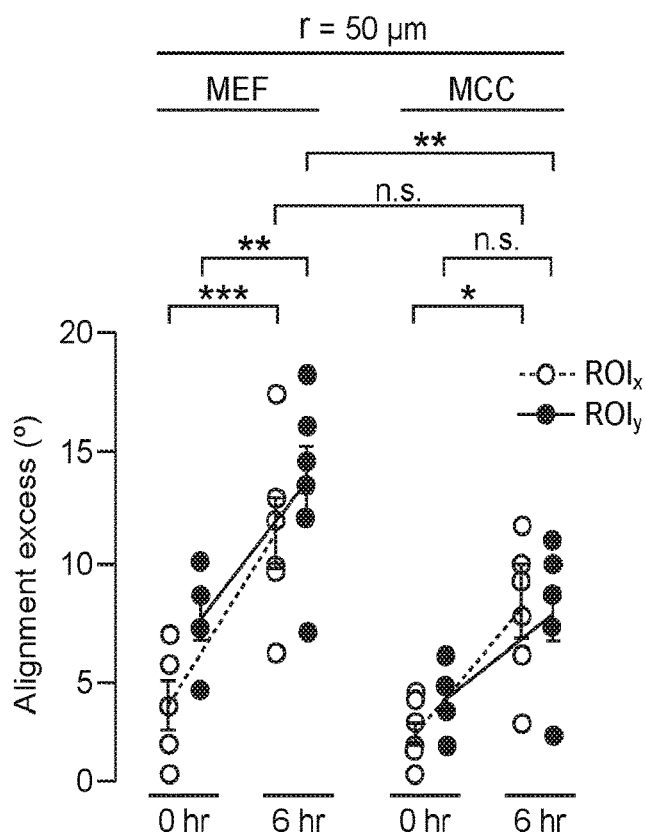
Figure 9:
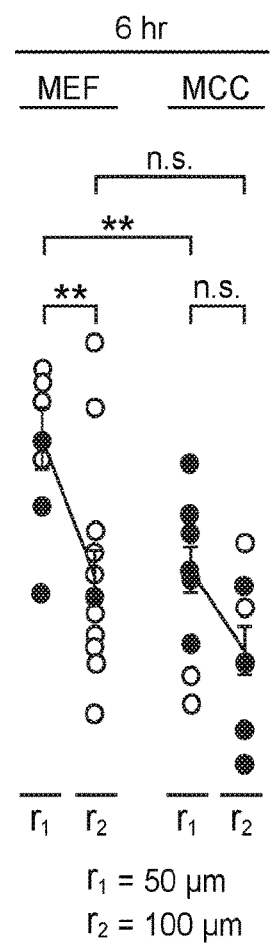
Figure 9:
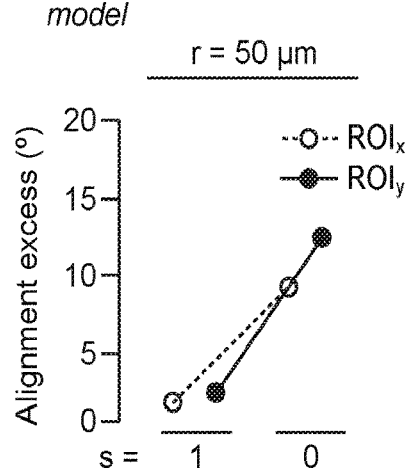
Figure 9:

To establish the sufficiency of condensation mechanics to drive tissue folding, we developed an in vitro model allowing the detailed analysis of cell compaction, ECM rearrangements, mechanical forces, and the relationship of these properties to the folding of nearby tissue interfaces. We began by reconstituting a microenvironment similar to the embryonic mesenchyme that incorporated components of an overlying laminin-rich basement membrane in a 250 μm thick slab of loose and collagen-rich fibrous ECM (Adams and Watt, 1993; Gersdorff et al., 2005; Stuart and Moscona, 1967). We embedded mouse embryonic fibroblasts (MEFs) near the surface of the gel slab (FIG. 4C-E, 5A). To control initial cell positions in the gel, we used patterning techniques such as DNA-programmed assembly of cells (DPAC) (Todhunter et al. 2015); and to model gel fiber rearrangements, we used finite-element modeling (FEM, FIG. 5B, FIG. 6-8). Cells generate traction forces that have previously been shown to strain and align matrix fibers in initially isotropic gels (Baker et al., 2015; Harris et al., 1981; Sawhney and Howard, 2002; Vader et al., 2009). Consistent with these reports, we found that grids of MEFs condense towards a focus, and that the radial strain associated with condensation is primarily accounted for by compaction of surrounding ECM (FIG. 5A). Even a minimal contractile system comprising a single cluster of 5-8 MEFs at reconstituted tissue interfaces produced pronounced local concentration and radial alignment of collagen fibers (FIG. 9). Moreover, for isolated pairs of clusters separated by up to 400 µm, we found amplified collagen fiber compaction and reorganization along their axis of interaction, forming "straps" (FIG. 5B, FIG. 10) (Sawhney and Howard, 2002).

Figure 10:
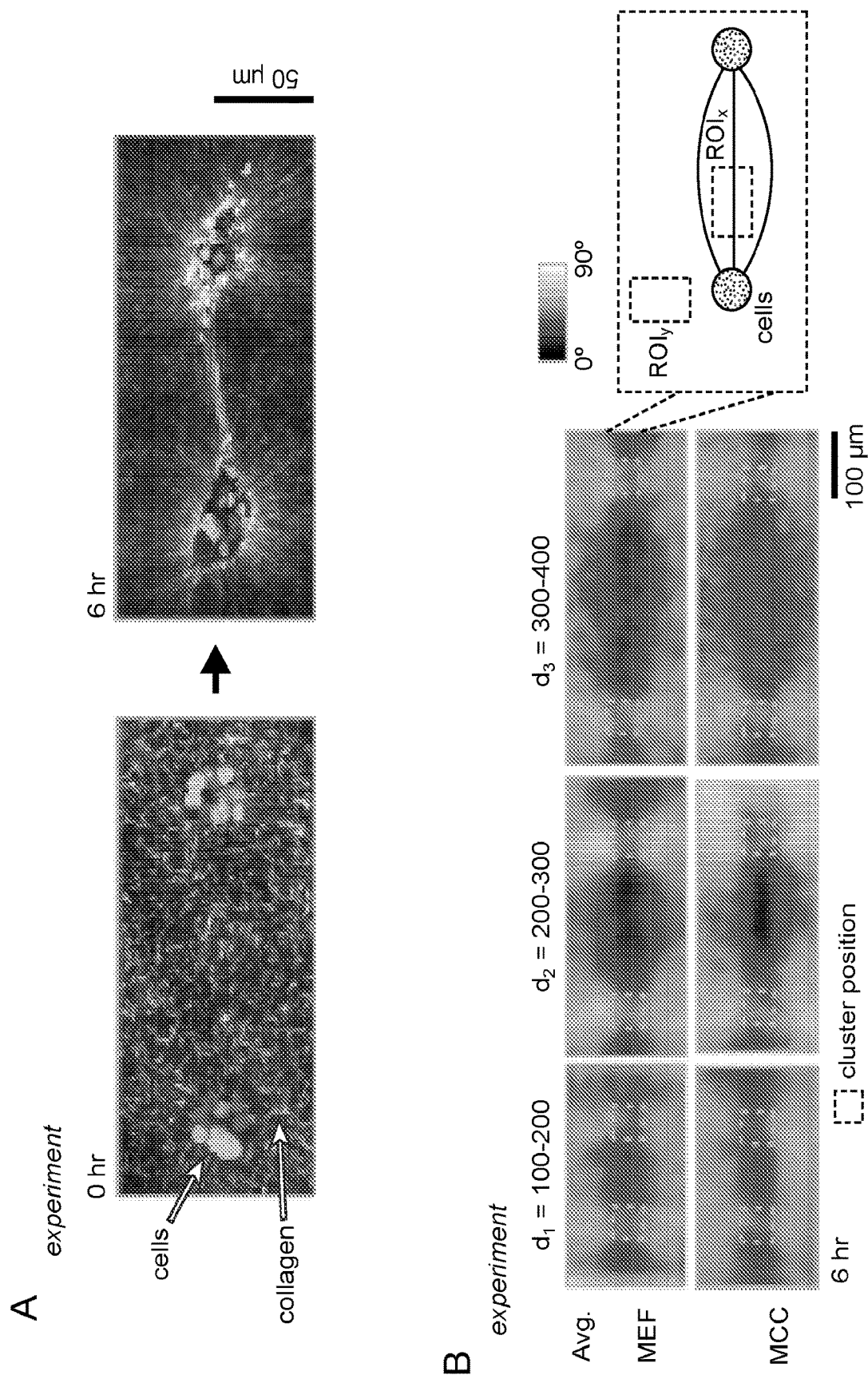
FIG. 10 illustrates that cell cluster pairs amplify collagen fiber alignment between them over distances of hundreds of microns.

FIG. 10 (E) illustrates formation of a localized curvature in a first surface of a collagen-rich gel by utilizing a combination of spaced apart clusters of fibroblasts and adherence of the opposite surface of the gel to a substrate to prevent the opposite surface from folding upon introduction of the localized curvature in the first surface. FIG. 10 (E) illustrates that by constraining a surface of a polymer matrix that includes fibers (e.g., collagen), folding can be limited to only one side of the gel (i.e., one surface) such that the fold is an indentation or a curvature on only one side of the matrix and in a localized region of that side—i.e., only a predefined region on one surface experiences compression leading to formation of a localized cleft. Such a methodology may be utilized to model initial stages of hair follicle formation at dermal papillae.

In a variation of the constraining and localized folding may involve, adhering the peripheral edges of the tissue—e.g., attaching the periphery of a planar tissue to a substrate while allowing the top and bottom surface of a planar tissue to be free from attachment to a substrate. Placement of spaced apart fibroblasts clusters would cause the polymer matrix present in location between the clusters to fold while also causing the gel present in the area between the fibroblasts clusters to stretch and thin out due to the constraints placed at the periphery of the gel.

In other variations of the disclosed methods, one or more regions in the interior of the tissue may be constrained by applying a compression force to a local region while a predetermined pattern of contractile cells cause other regions in the tissue to fold.

A two-parameter FEM consisting of isotropic contractile nodes within a grid of unit cells constructed from elastic springs qualitatively captured the same amplified mesh alignment between nodes and suggested that these regions coincided with higher tensile stresses relative to less strongly-aligned regions. Biophysical studies suggest that regions of gel under elevated tensile stresses should undergo elastic recoil upon cutting in proportion to the local tension orthogonal to the incision (Bonnet et al., 2012; Kumar et al., 2006; Legoff et al., 2013). Indeed, in both experiments and FEM, significantly greater recoil of the gel surface occurred upon ablation with a focused UV laser at straps in comparison to regions orthogonal to straps, or to control regions distant from cells (FIG. 5C).

Cell condensation, ECM compaction, and fiber alignment are signature changes of mesenchymal condensations observed in several in vivo systems. By additionally demonstrating the accumulation of tensile stresses in aligned fibers, our observations show that the process of mesenchymal condensation can generate forces that strain fibrous ECM gels. For small strains along a single tissue interface, we would expect a proportional change in its curvature. Indeed, we observed the progressive emergence of curvature at tissue interfaces proximal to single condensing clusters, as well as along collagen straps between pairs of clusters (FIGS. 9, 10). We hypothesized that the same phenomena that drive changes in curvature around individual cell clusters could set the curvature of tissue interfaces across considerably larger distances through the cumulative action of networks of mechanically coupled cells. In this way, the positions and density of condensing mesenchymal cells should determine interfacial strains, thereby having a direct, predictable, and reproducible relationship to the final architecture of the tissue—a key requirement of any robust developmental program.

Figure 11:
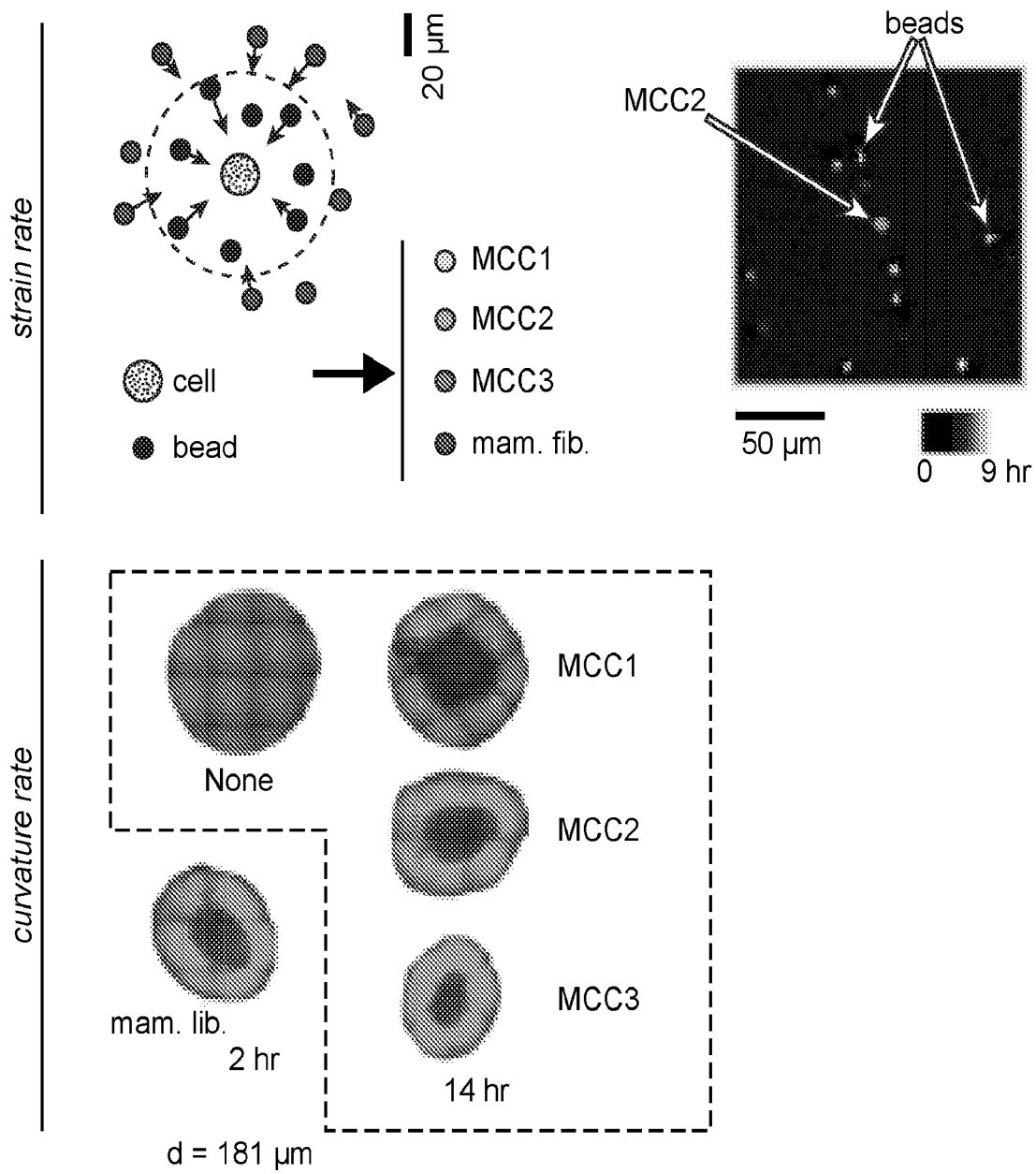
FIG. 11 illustrate that rates of reconstituted tissue curvature are determined by the rate at which actuating cells strain the gel.
Figure 11:
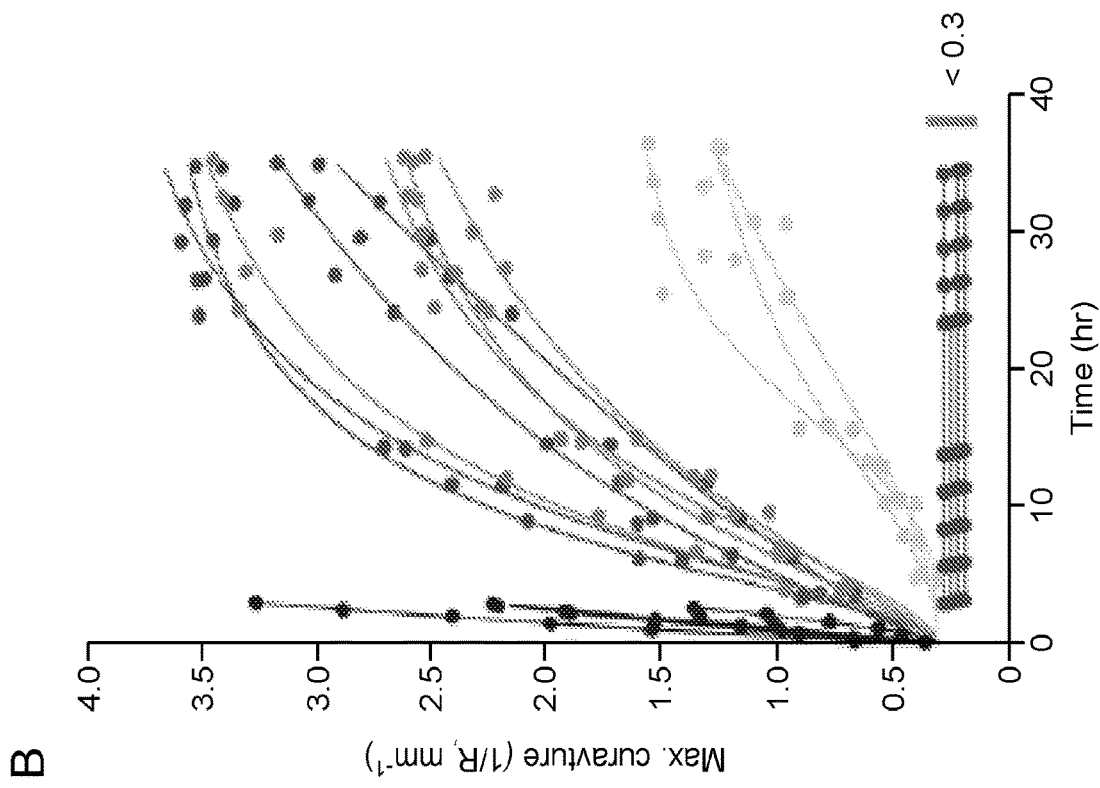
Figure 12:
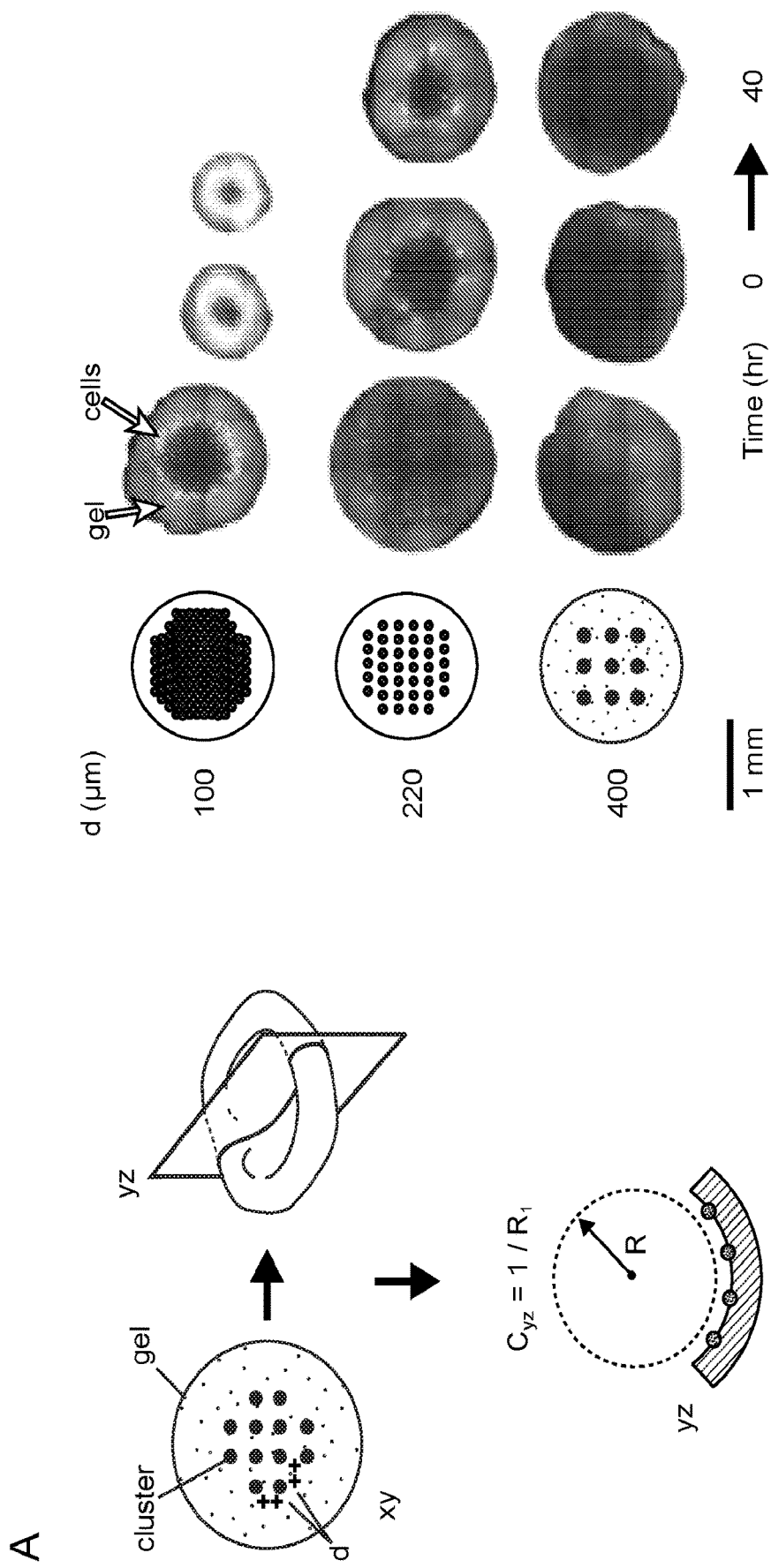
FIG. 12 illustrates isotropic reconstituted tissues follow monotonic curvature trajectories.
Figure 12:
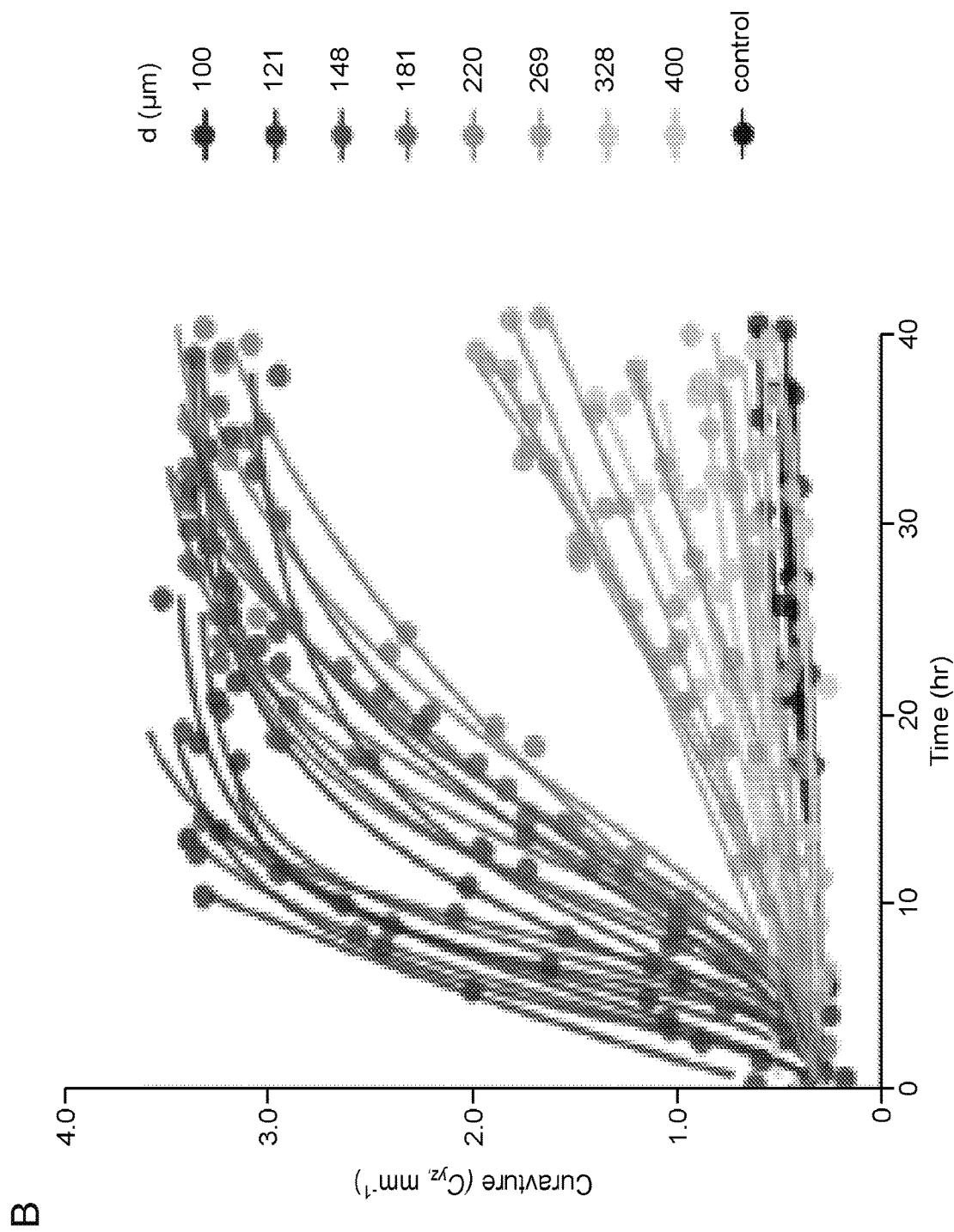

To verify this, we quantitatively mapped cell arrangements in condensing grids to out of—plane curvatures for two folding motifs—isotropic and anisotropic grids of cells (FIG. 5D). We first prepared isotropic grids of cell clusters at the upper surface of free-floating ECM gels using DPAC (with equal spacings $d=d_x=d_y$ between clusters in x and y). These gels formed radially-symmetric invaginations with curvatures that increased over time. Moreover, the initial curvature rates of the invaginating gels were proportional to the rates at which the condensing cell type strained the surrounding ECM, with curvature dynamics spanning characteristic timescales of ~5 to >40 hours (FIGS. 11, 12).

Figure 13:
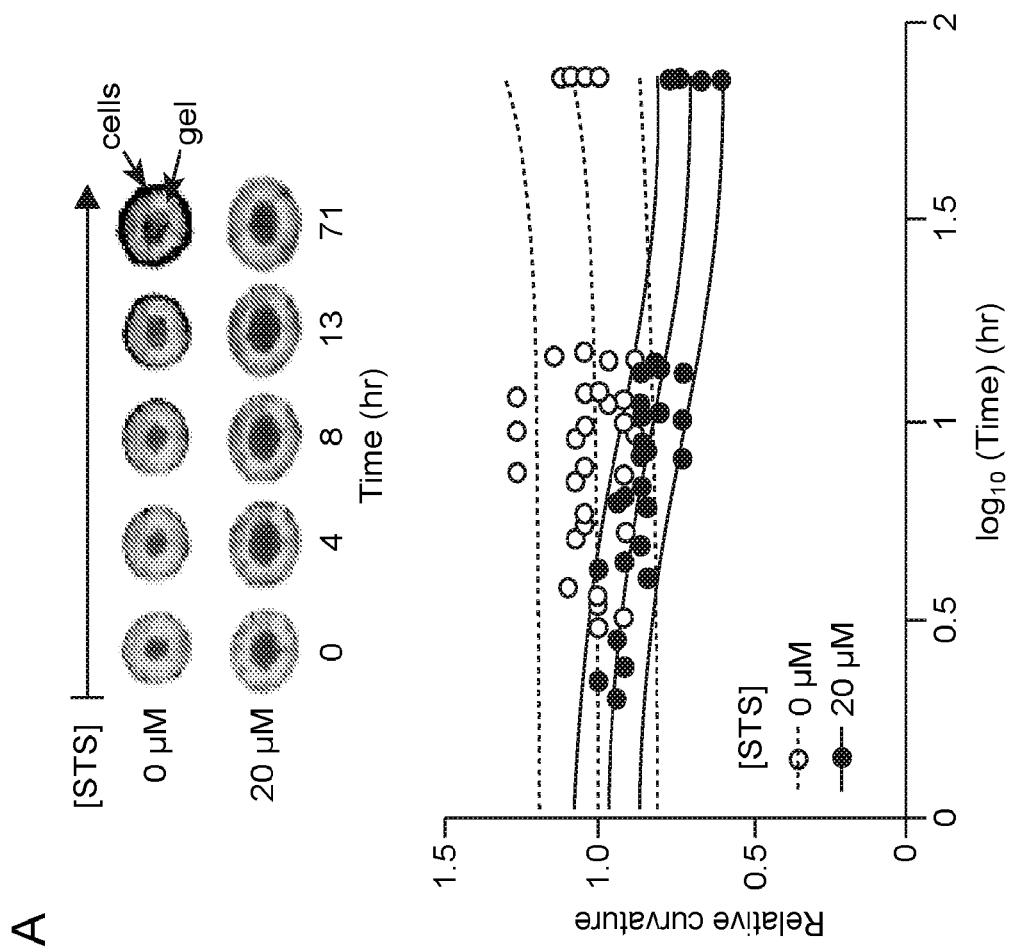
FIG. 13 depicts reconstituted tissues only partially unfold after ablating actuator cells.

We chose relatively slower-folding reconstituted tissues bearing isotropic grids of mesenchymal-like carcinoma cells (MCCs) to enable detailed measurement of the temporal dynamics of folding by whole-tissue confocal microscopy. We found that the gel curvature C at a given time-point increased monotonically for smaller d (with the number of clusters $N_c$ increasing as $N_c \sim 1/d_2$, FIG. 5D). The experimental C vs. $N_c$ data were adequately fit by both a proportional scaling relationship ($R_2=0.8$, for bending induced by constant strain-rate actuators (Holmes et al., 2011; Timoshenko and Woinowsky-Krieger, 1959), and by a 3D implementation of our FEM. We additionally found that the emergence of curvature coincided with extensive and irreversible gel remodeling since pre-folded tissues unfolded by less than 40% upon inducing apoptosis of condensing cells using staurosporine (FIG. 13).

Figure 14:
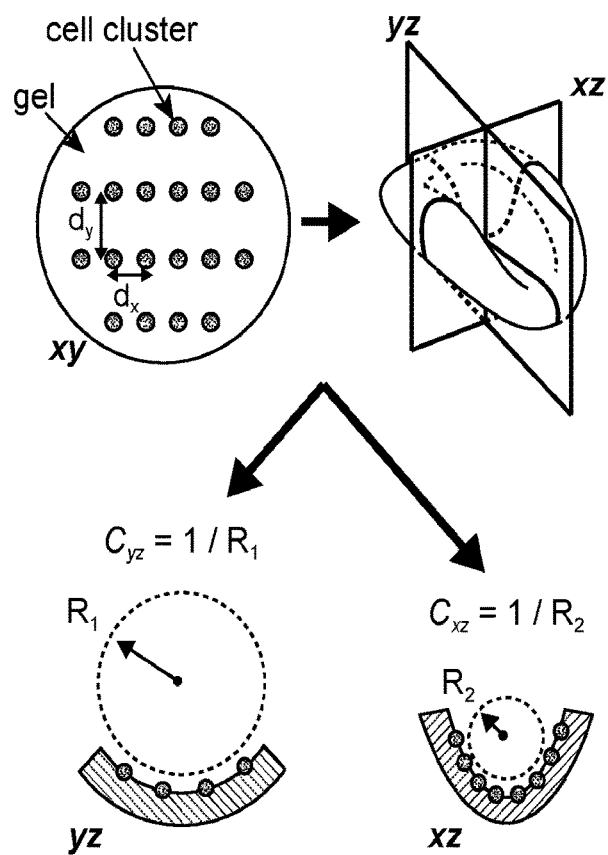
FIG. 14 depicts that fidelity of anisotropic folds is limited by contractile cluster migration.
Figure 14:
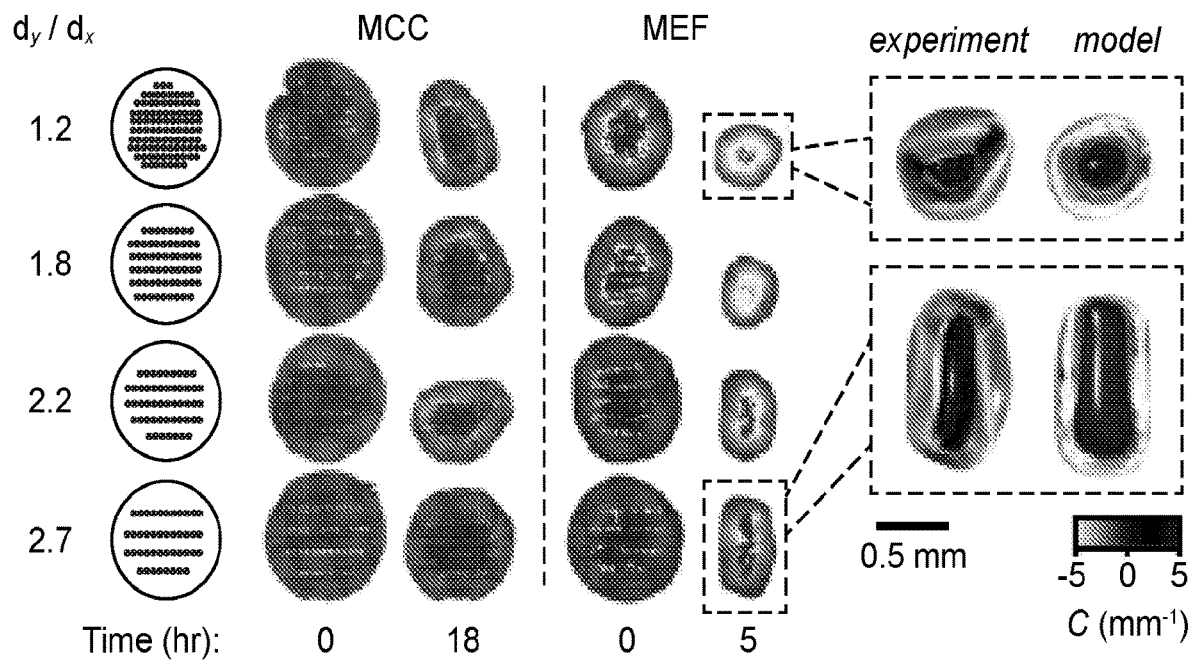
Figure 14:
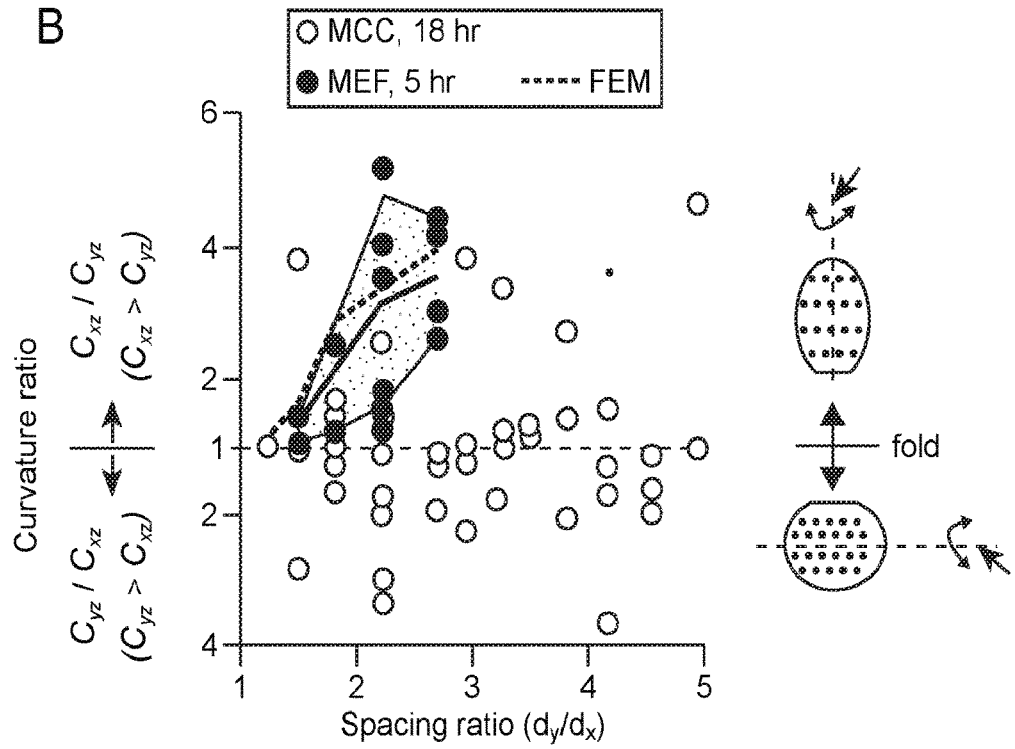
Figure 14:
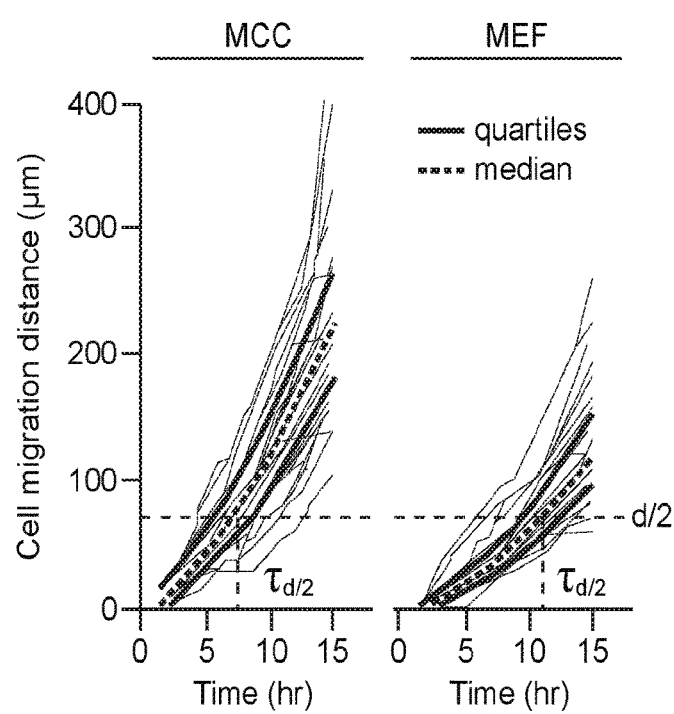
Figure 14:
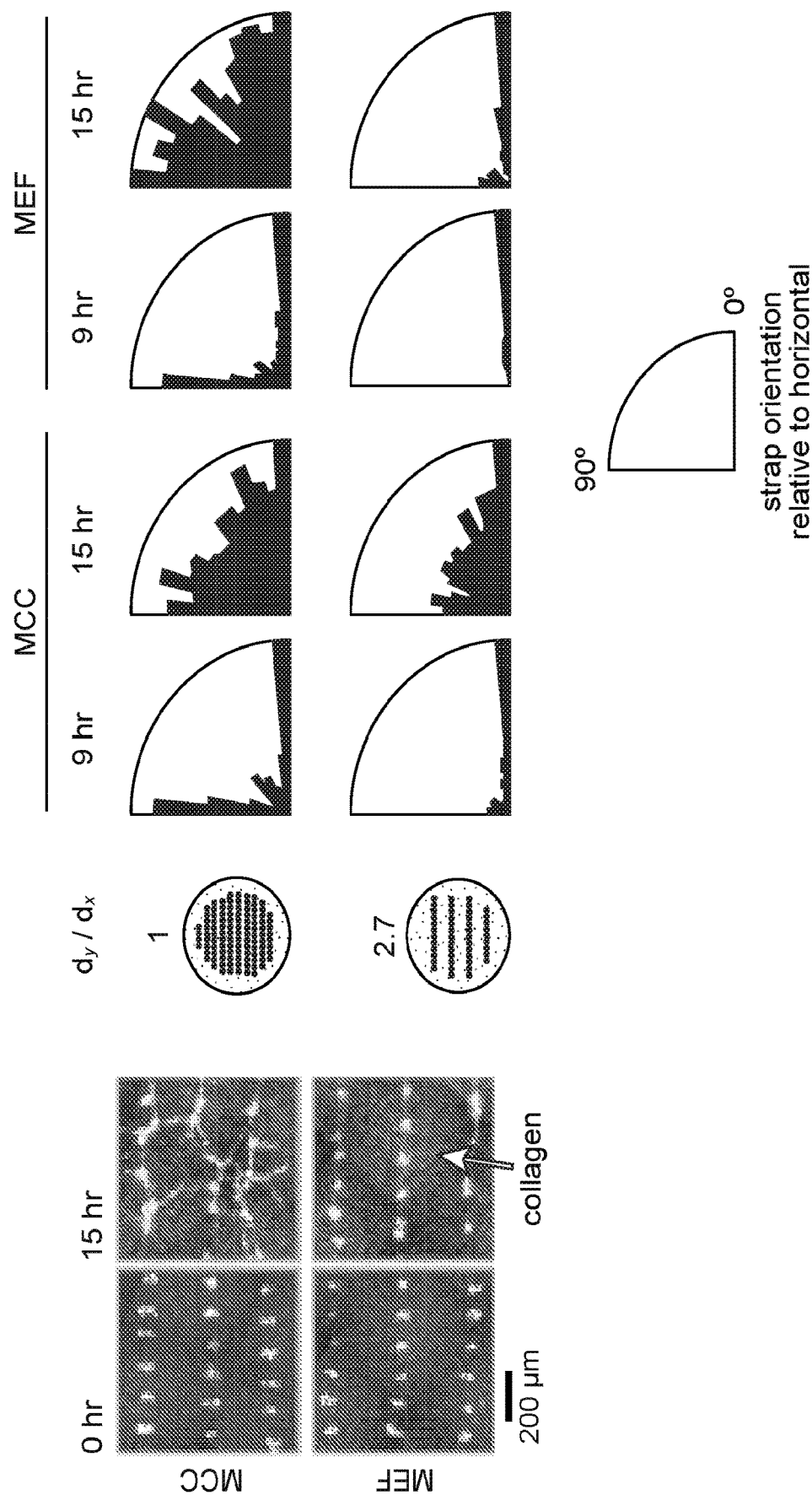
Figure 15:
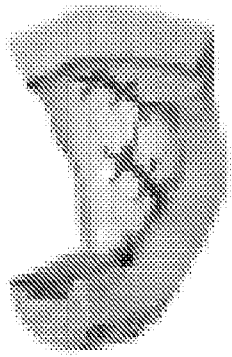
FIG. 15 depicts that mesenchymal condensation is sufficient to sculpt tissue interfaces into diverse 3D forms.
Figure 15:
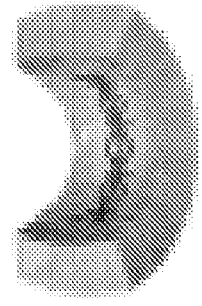
Figure 15:
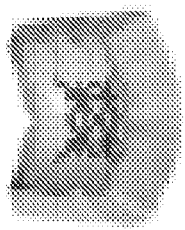
Figure 15:
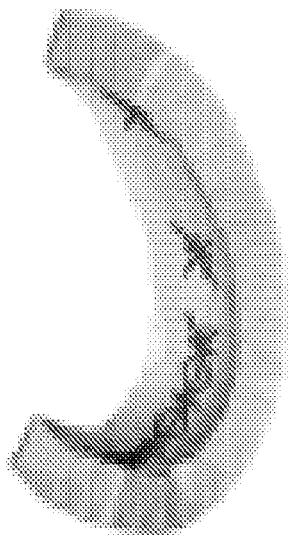
Figure 15:
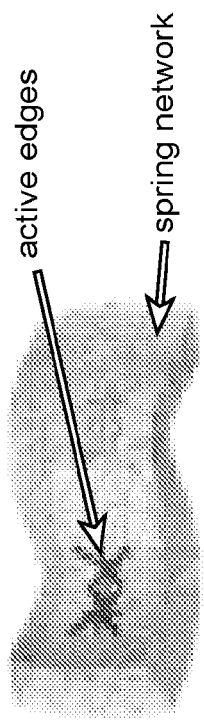
Figure 15:
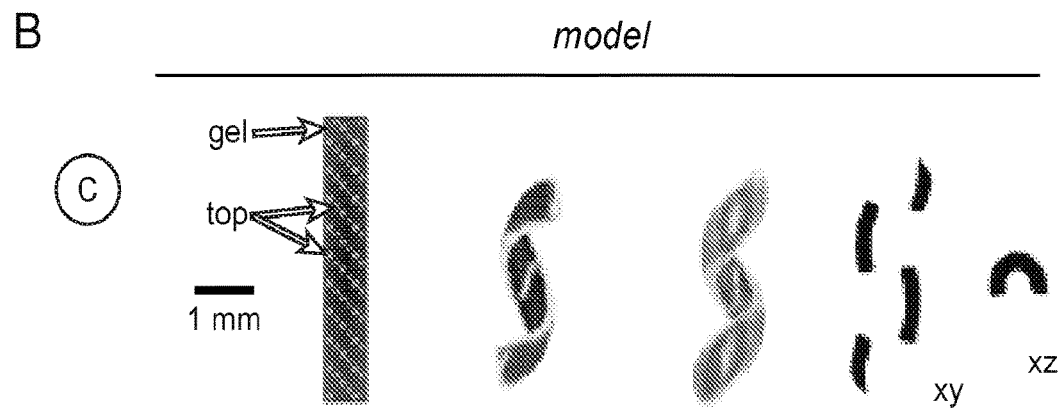
Figure 15:
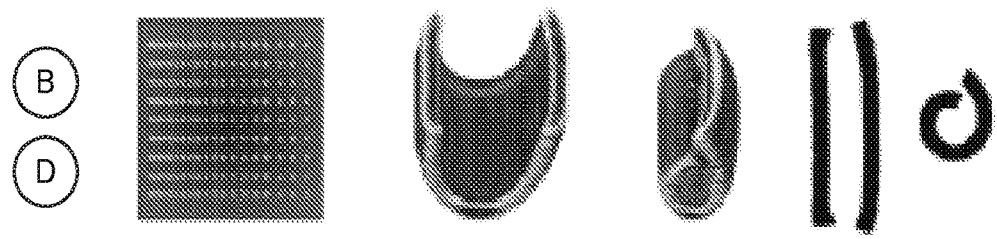
Figure 15:
Figure 15:
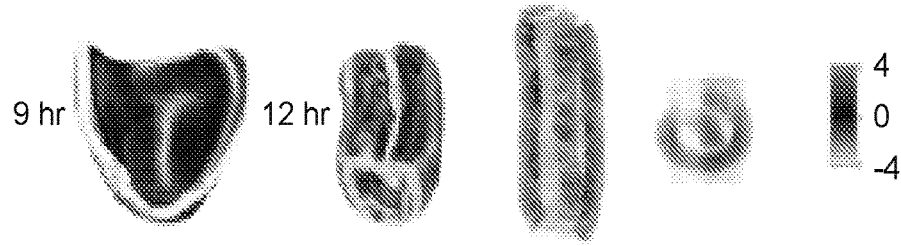
Figure 15:
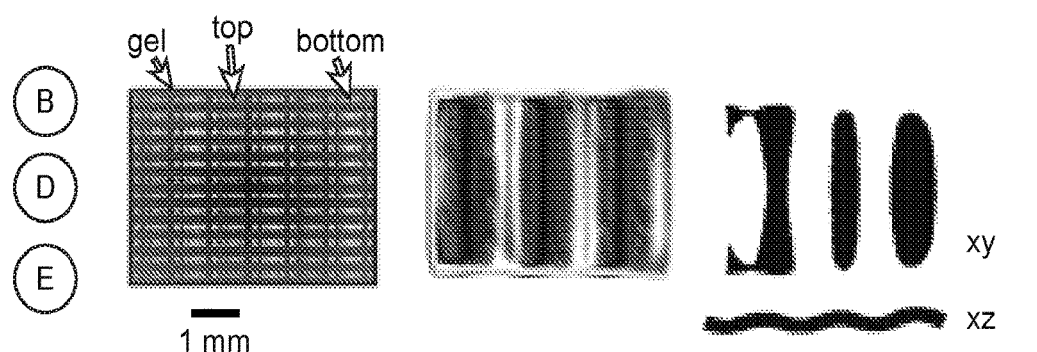
Figure 15:
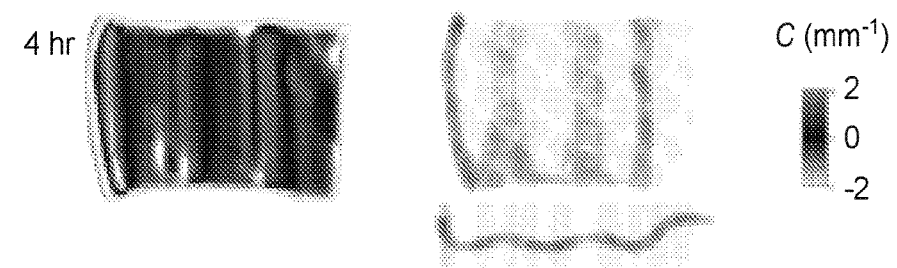
Figure 15:
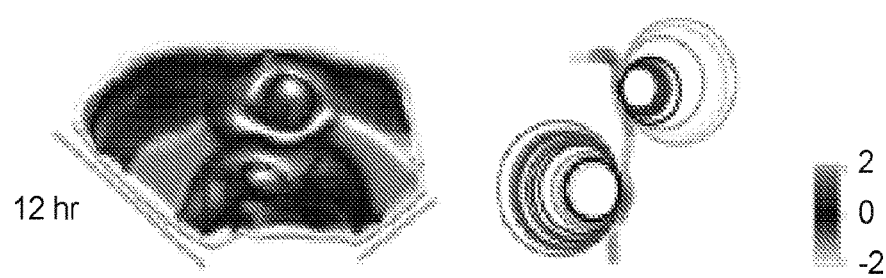
Figure 15:
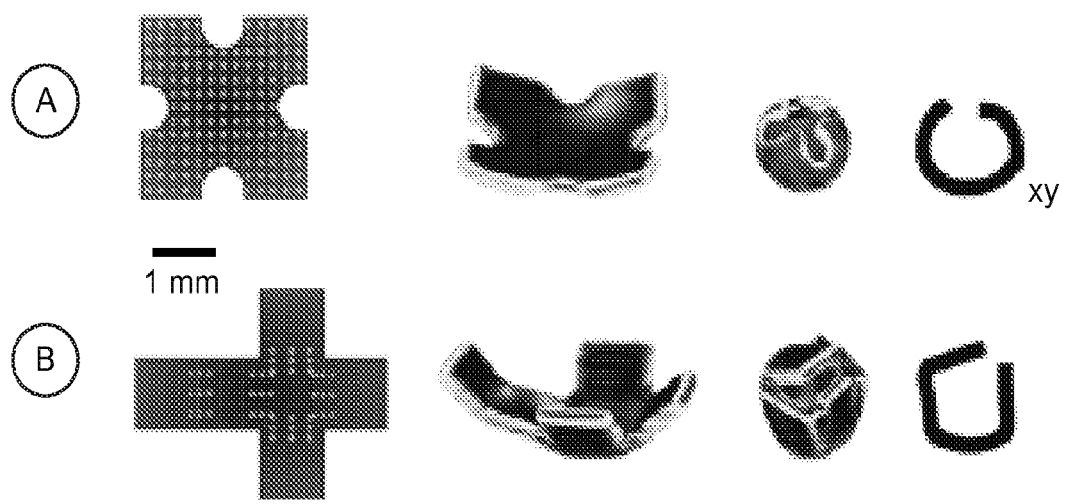
Figure 15:
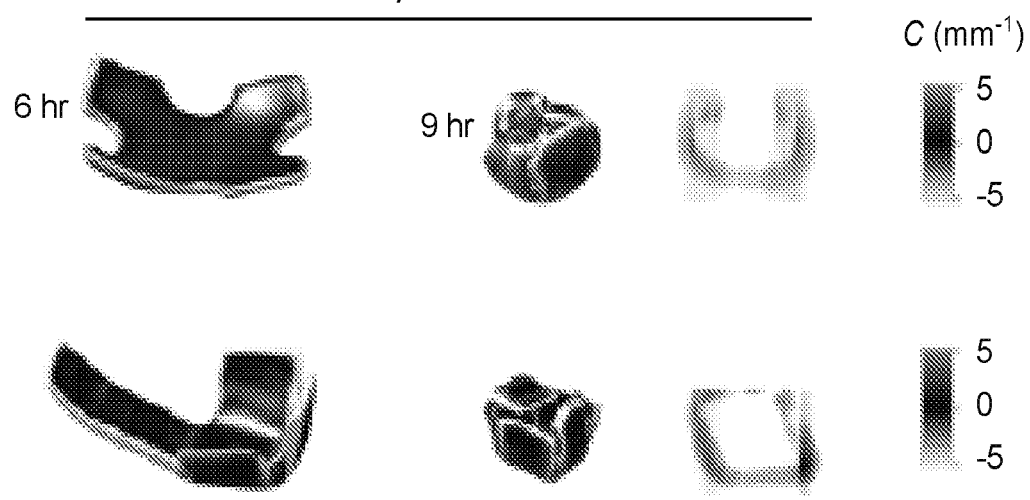

Moving beyond radially symmetric invaginations, we predicted that anisotropic motifs having a greater density of cell clusters along the x axis relative to the y axis would program a fold running along the y axis, since tension-bearing collagen straps form preferentially between nearest neighbor clusters in anisotropic grids during condensation (FIG. 14). Indeed, anisotropic MEF grids consistently folded gels along the expected axis, and curvature anisotropy in x and y was approximately proportional to cluster spacing anisotropy (FIG. 5D). Surprisingly, identical grids actuated by less contractile and more migratory MCCs did not form controlled anisotropic folds along a predictable axis (FIG. 15). Upon further investigation, we found that the ratio of folding rate to cell migration rate for a given condensing cell type was critical in determining the fidelity with which anisotropic folds could be specified.

Figure 16:
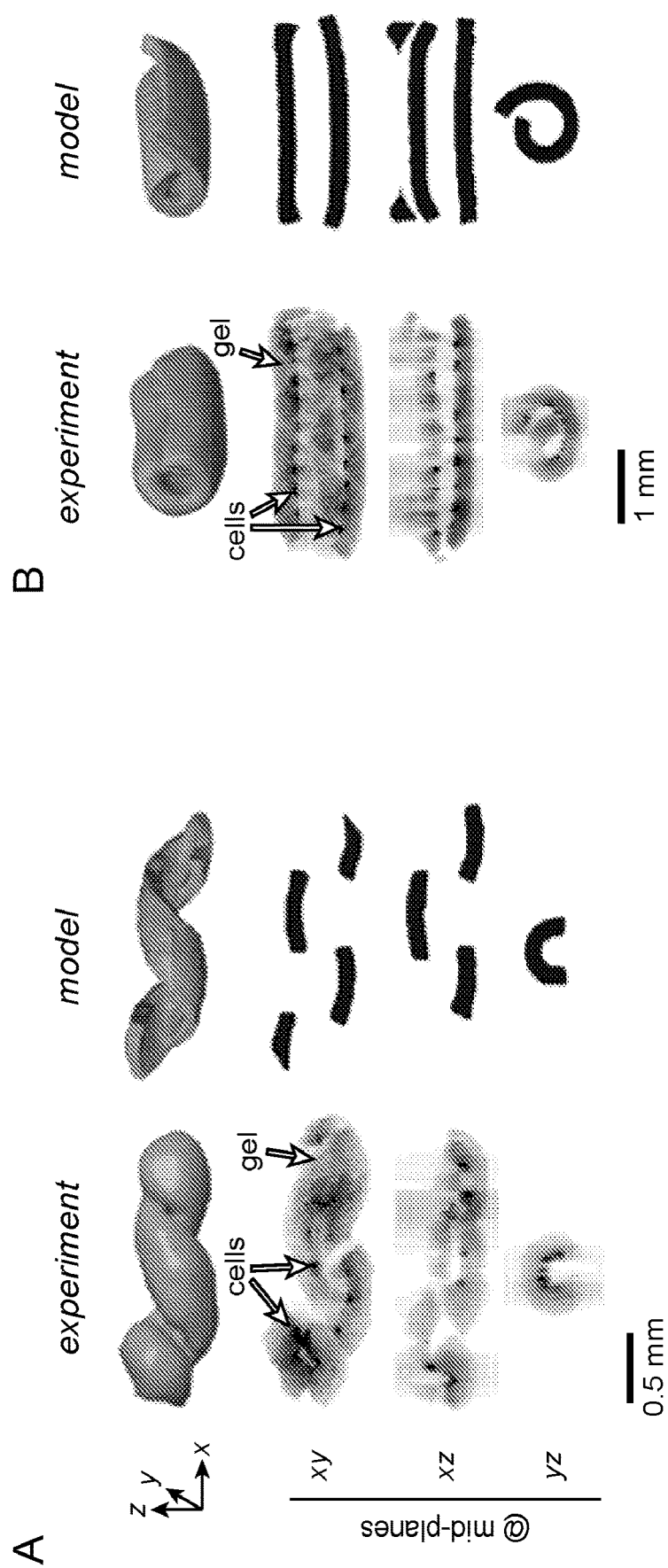
FIG. 16 illustrates section analysis for curl, tube, and corrugation reconstituted tissues.
Figure 16:
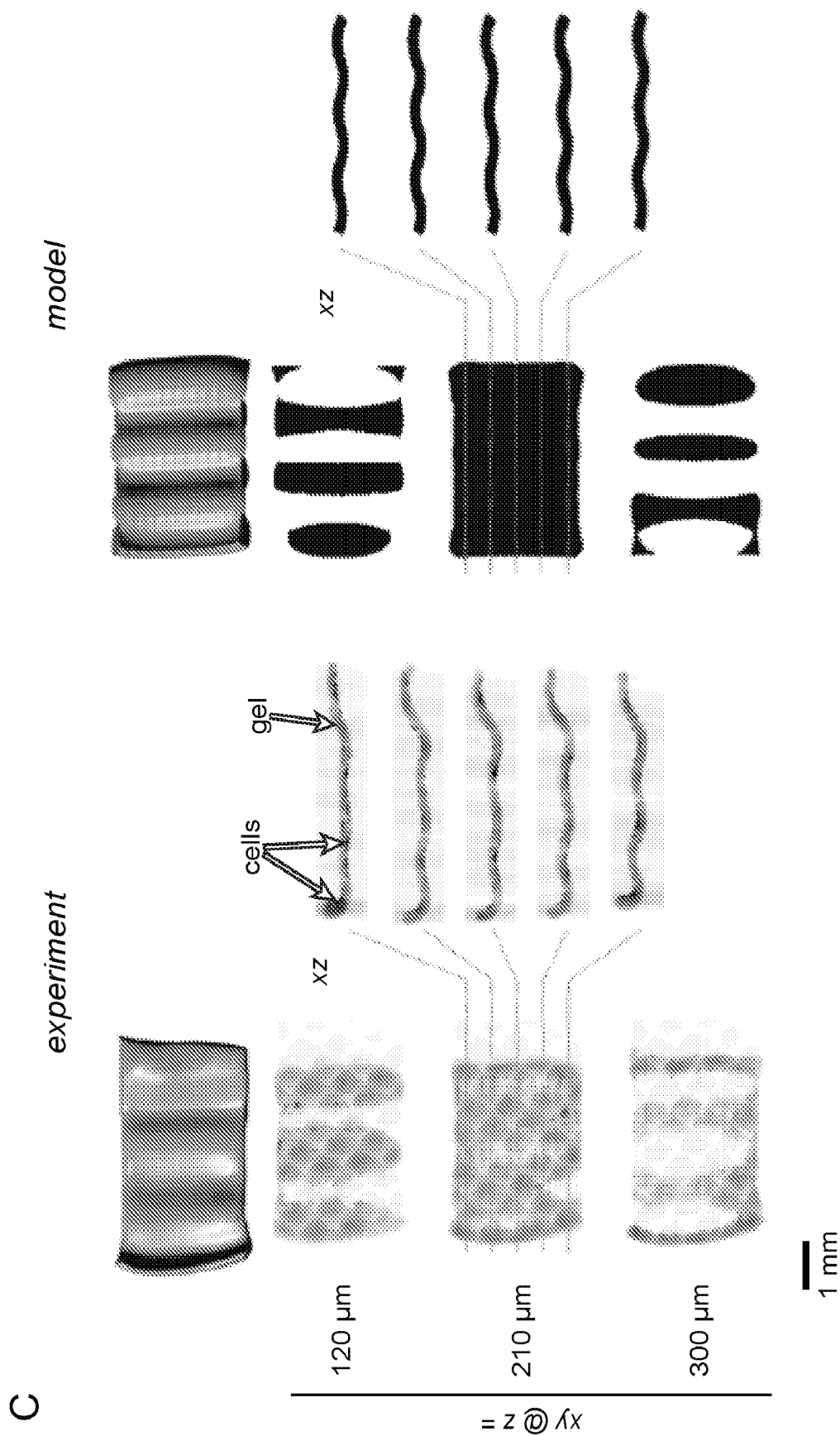
Figure 17:
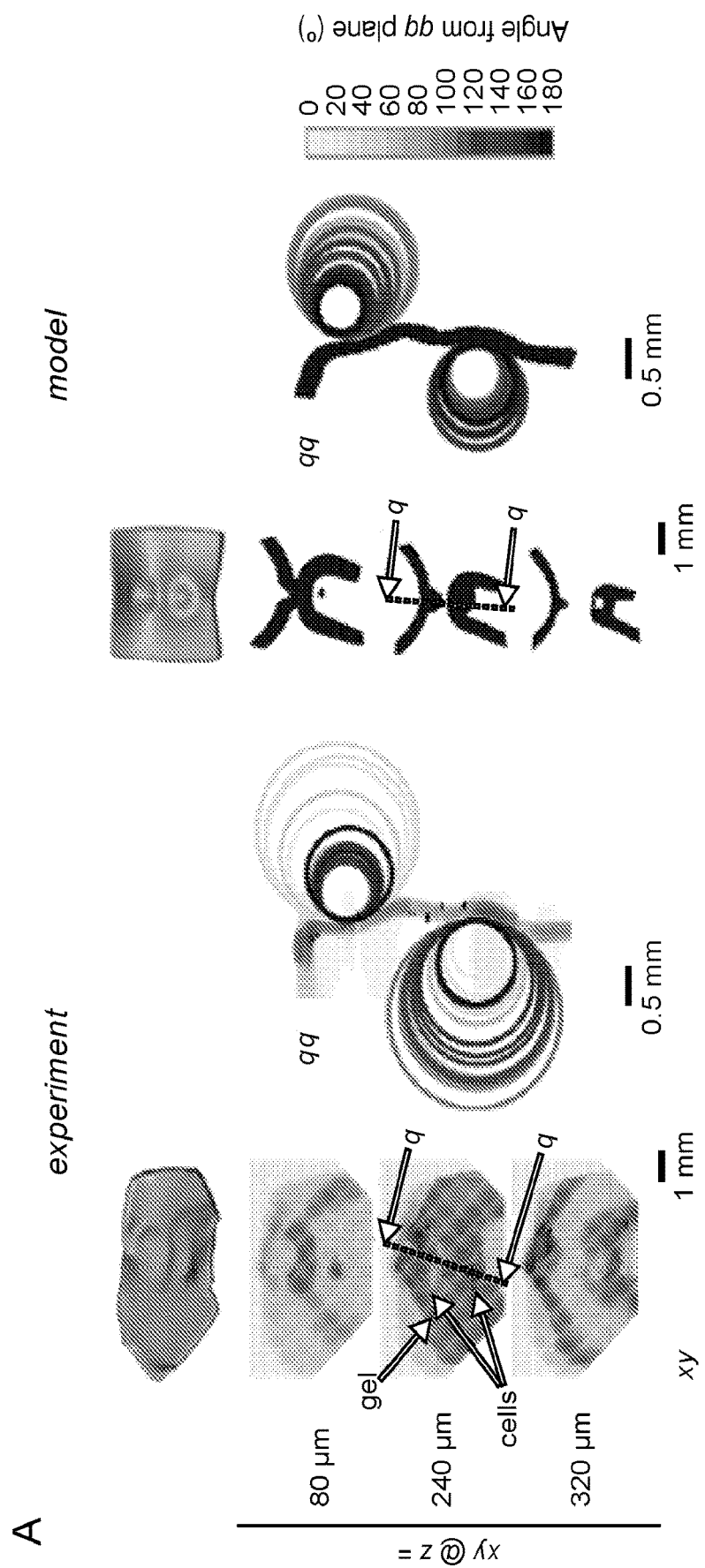
FIG. 17 illustrates Section analysis for double cap, sphere, cube, and Miura reconstituted tissues.
Figure 17:
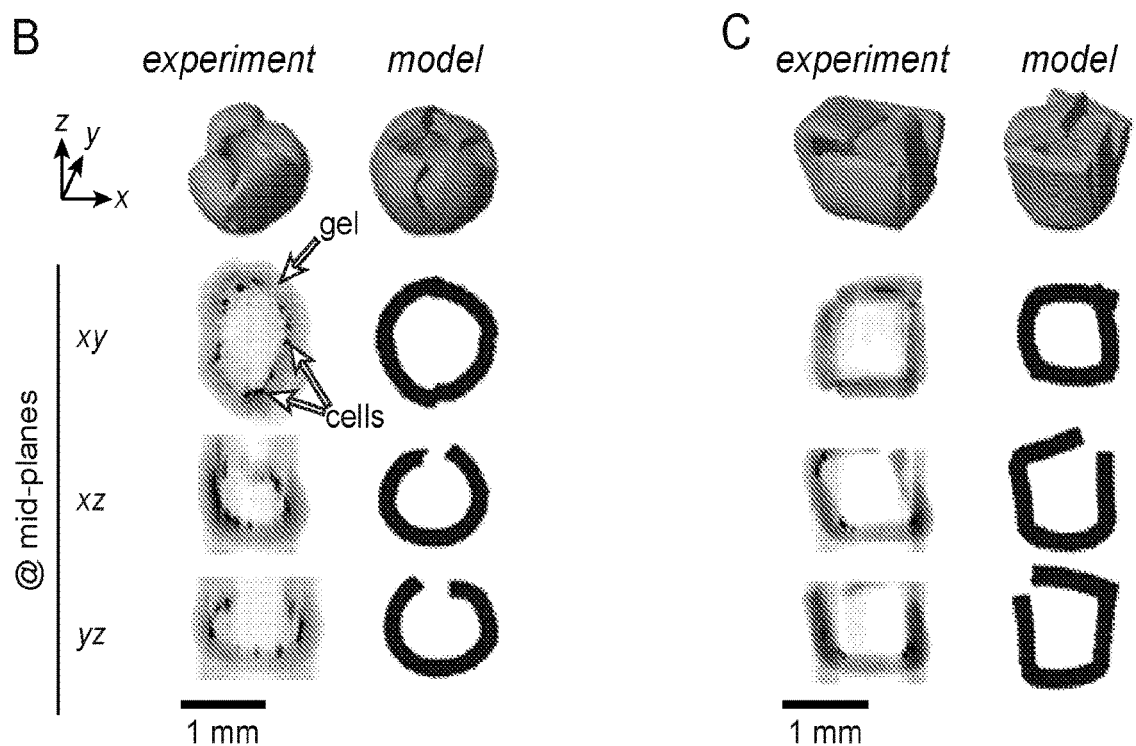
Figure 17:
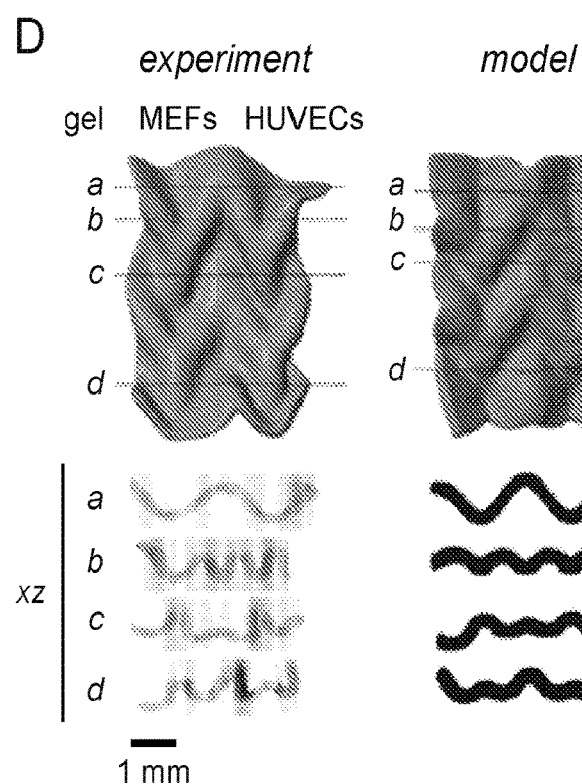

We continued to explore the generality and robustness with which mesenchymal condensates could fold gels into complex geometries by building and combining isotropic, anisotropic, and three additional folding motifs: curl, compound, and opposing (FIG. 15, FIGS. 16 and 17). We first implemented the curl motif in which lines of MEF clusters were placed at a 45° angle to a rectangular ECM substrate, encoding a partially-enclosed helical shape with a pitch of 1 mm and radius of 200 microns (with comparable values of 1.2 mm and 220 microns in a member of the corresponding FEM family, FIGS. 15B and 15C). Combining motifs, we incorporated compound curvature into an anisotropic grid to make a rolled tube shape using lines of log-spaced clusters from 80 to 250 microns in x set apart by 300 microns in y (data not shown). The tube was hollow throughout its length, with an inner diameter of 550 microns +/−9% CV lengthwise (555 microns+/−4% by FEM). We then incorporated an opposing curvature motif into a fourfold-vertex shape where three folds of the same orientation converge with one in the opposite orientation at a single point. We found that such opposing fold patterns were robust to "pop-through" defects if the cluster densities encoding adjacent folds were comparable (FIG. 18).

Combining anisotropic, compound, and opposing curvature folding motifs generated a corrugation of pitch 1.6 mm and amplitude 130 microns (1.6 mm and 115 microns by FEM, FIGS. 15D and 15E). Next, we encoded two adjacent opposing isotropic caps in a single ECM sheet using sets of concentric cell cluster grids on the top and bottom surfaces. Locally, the curvature profiles generated in this way were similar (but of opposite sign) at +1.6+/−34% azimuthally and −2.1 $mm_{-1}$+/−30% after 12 hr in culture (+2.3 $mm_{-1}$+/−15% and −2.1+/−29% by FEM), although residual in-plane stresses in this "non-developable" geometry likely led to the additional buckling of the sheet observed at its periphery (Armon et al., 2011).

The in vivo relationship between local in-plane residual stresses and the trajectory of tissue folding is a complex function of tissue boundary conditions, and feedback on compensatory cellular behaviors including cell division, cell shape changes, and ECM remodeling (Humphrey and Dufresne, 2014; Legoff et al., 2013). We specifically explored modification of tissue boundary conditions by strategically cutting surfaces prior to folding to enable spherical and cubic reconstituted tissues (as in the Kirigami art form) (Sussman et al., 2015; Zhang et al., 2015). We built both tissue architectures using laser microdissection of gel substrates prior to folding (FIGS. 15F and 15G); in the latter case relying on anisotropic curvature at continuous cube edges to actuate folding.

The process of morphogenesis often results in repetitive juxtaposition of architectural motifs, such as the nephrons of the kidney, the alveoli of the lung, and the folds of the dermal-epidermal junction. We reasoned that just as different folding motifs can be combined to make a diverse family of folds; these folds could be tiled as repeating subunits to construct architectures of even greater size and complexity. Inspired by the zig-zag-shaped luminal surface of the embryonic day 13-16 (E13-16) chick gut (Shyer et al., 2013), we designed a tessellation of the four-fold junction in analogy to the Miura origami fold (FIG. 19A). The Miura fold has several unusual geometric features, including a negative Poisson ratio and the capability to be fit generically to complex target surfaces (Dudte et al., 2016). Finite element modeling of our Miura design predicted a folding trajectory with striking similarity to the chick gut (FIG. 19B). Indeed, the constructed Miura fold autonomously emerged from a 6×8 mm flat sheet to a 4×6 mm zig-zag structure at 15 hr with all 31 folds having the correct orientation, and similar periodicity and amplitude as those in the FEM.

A remarkable aspect of tissue folding processes in development is that their curvature trajectories are generally robust, even within microenvironments with complex cellular compositions (Nelson, 2016; Savin et al., 2011). We therefore tested the robustness of mesenchymal condensation-driven folding in reconstituted tissues incorporating other cell types as "passengers". We reasoned that a given folding trajectory predicted by FEM would not be disrupted if the mechanical activity of passenger cells on the ECM was significantly lower than that of condensing mesenchymal cells. We therefore screened 7 cell types for their ability to contract ECM droplets, finding that MEFs and primary human mammary fibroblasts contracted droplets to a much greater extent than other common cell types, including endothelial and epithelial lines (FIG. 19C). These data suggested that the latter cell types, themselves critical components of most tissues, would not interfere with folding trajectories dominated by the properties of the mesenchyme. Likewise, our ability to include additional cell types in juxtaposition with condensing mesenchyme raised the secondary possibility that the behavior of passenger cells would be altered in response to the changing tissue architecture directed by the condensing mesenchyme (Mammoto et al., 2013; Shyer et al., 2015).

To test these hypotheses we patterned multiple cell types in reconstituted tissues directed to fold into the Miura pattern (FIG. 19D-F). 3-pronged HUVEC cords were positioned underneath incipient folds and carried along during the folding process; while Caco2 cells (a colon carcinoma cell line) were carried on top by embedding them uniformly near the tissue surface. We found that the folded shapes of these passenger cell-laden Miura tissues were similar to those predicted by FEM, confirming that the properties of the condensing mesenchymal cells dominate folding trajectories (FIG. 19B,E). We additionally found that HUVEC migration was biased along incipient folds, suggesting that emerging tissue topographies and changing ECM properties feedback on the behavior of passenger cells (FIG. 20). At later timepoints, the HUVEC cords became fully encapsulated within the zigzag folds, and were lumenized across 100-200 micron tracts after 36 hr. Finally, we found that Caco2 cells, which form 3D cysts in matrigel (Ivanov et al., 2008), became concentrated at the base of valley folds on top of the network of fibroblasts. This completely synthetic folded tissue had a gross architecture with striking similarity to the developing small intestine (Walton et al., 2016).

Animal development involves progressive elaboration of tissue structure at multiple length-scales, with each step of morphogenesis predicated upon the architecture formed in preceding steps. Thus, tissues are inherently imprinted with a developmental history in their shape and anisotropy that is critical for sculpting local cell-fate decisions, and for directing subsequent self-organization processes that ultimately determine tissue function. Mesenchymal condensation is one of the core vertebrate developmental programs underlying this imprinting of topography and cellular composition at the interface of the epithelium and mesenchyme (Mammoto et al., 2013). The events that coincide with the emergence of curvature during mesenchymal condensation are complex, involving changes in the mechanics and paracrine signaling between multiple cellular components in each layer (Eames and Schneider, 2005; Varner and Nelson, 2014; Walton et al., 2012). However, the contribution of the mechanics of the mesenchyme in these processes has not been studied in detail, and the onset of curvature is hypothesized to be driven primarily by epithelial cell behaviors such as migration or shape changes (Lecuit et al., 2011). We find that in the context of a loose and fibrous ECM composite, the mechanics and dynamics of condensing mesenchymal cells are sufficient to explain a variety of shape transitions in nearby tissue interfaces. In these cases, the mesenchyme behaves like an active composite material, with cells straining and compacting the ECM, aligning ECM fibers between regions of compaction, and encoding stresses in the material along regions of maximum fiber alignment. These stresses lead to out-of-plane buckling of the material at tissue interfaces along trajectories that can be predicted using finite element modeling. The predictable behavior of this living material allowed us to program the autonomous folding of cell-ECM composites into a variety of 3D architectures bearing striking similarity to structures found in vivo. This process is analogous to the autonomous folding of abiotic materials into complex shapes (Holmes et al., 2011;

Kim et al., 2012; Na et al., 2014; Sydney Gladman et al., 2016; Tallinen et al., 2016). Moreover, the self-organizing and dynamic properties of a mesenchymal cell-ECM composite bear striking similarity to phenomena observed in reconstituted actomyosin networks (Linsmeier et al., 2016), suggesting these active materials may be guided by common physical principles.

Figure 6:
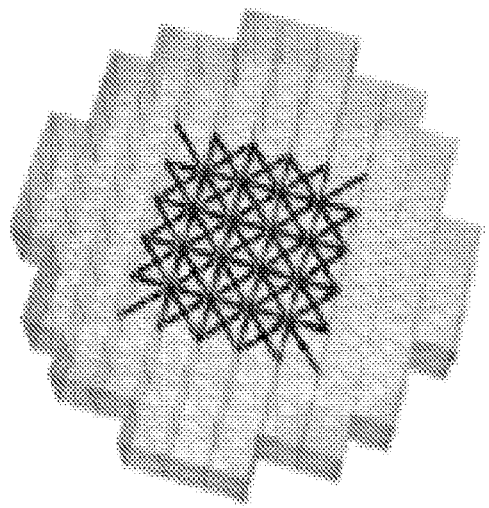
FIG. 6 illustrates that ECM tension at tissue interfaces leads to invagination or evagination dependent on differences in layer mechanics.
Figure 6:
Figure 6:
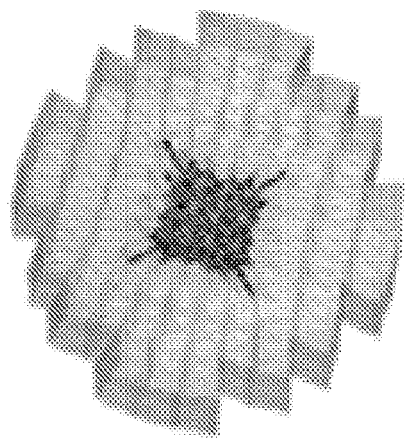
Figure 6:
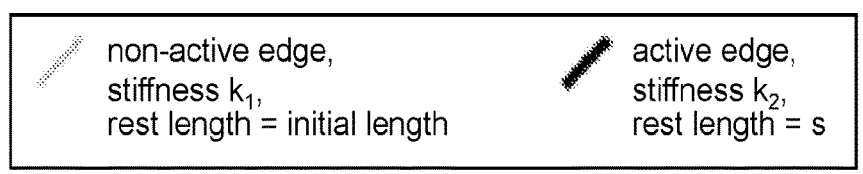
Figure 6:
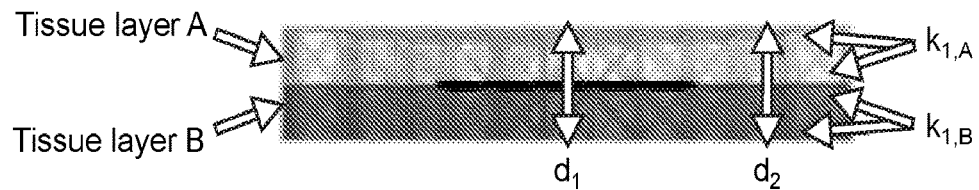
Figure 6:
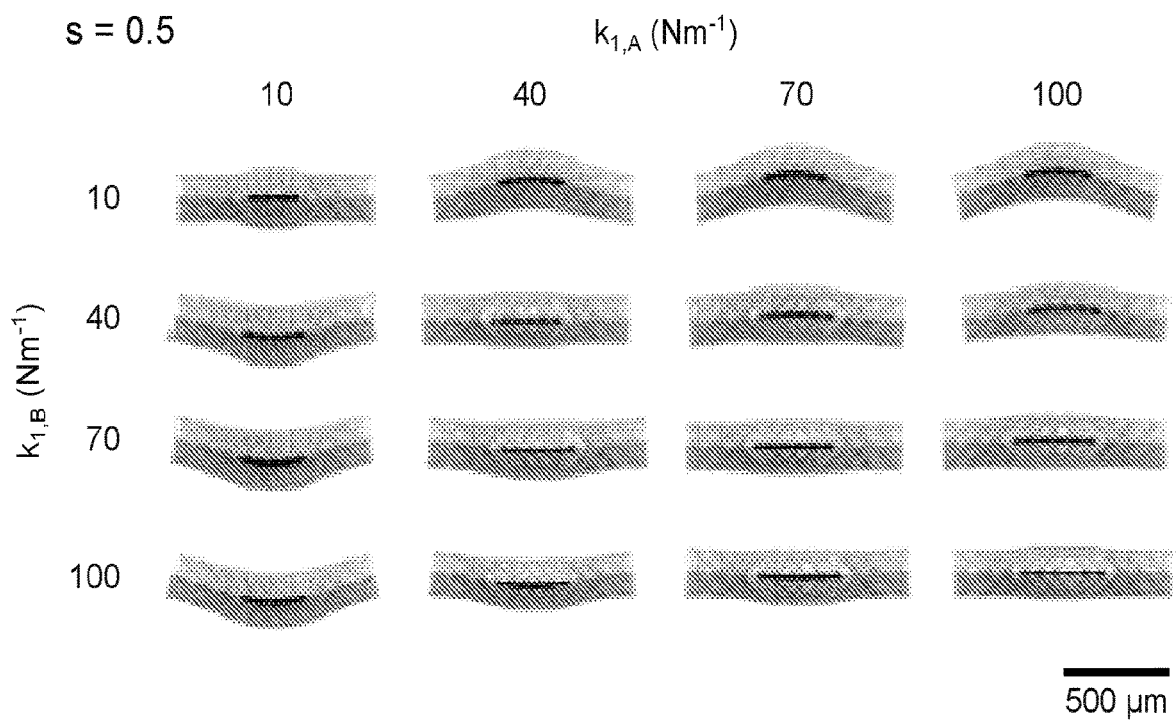
Figure 6:
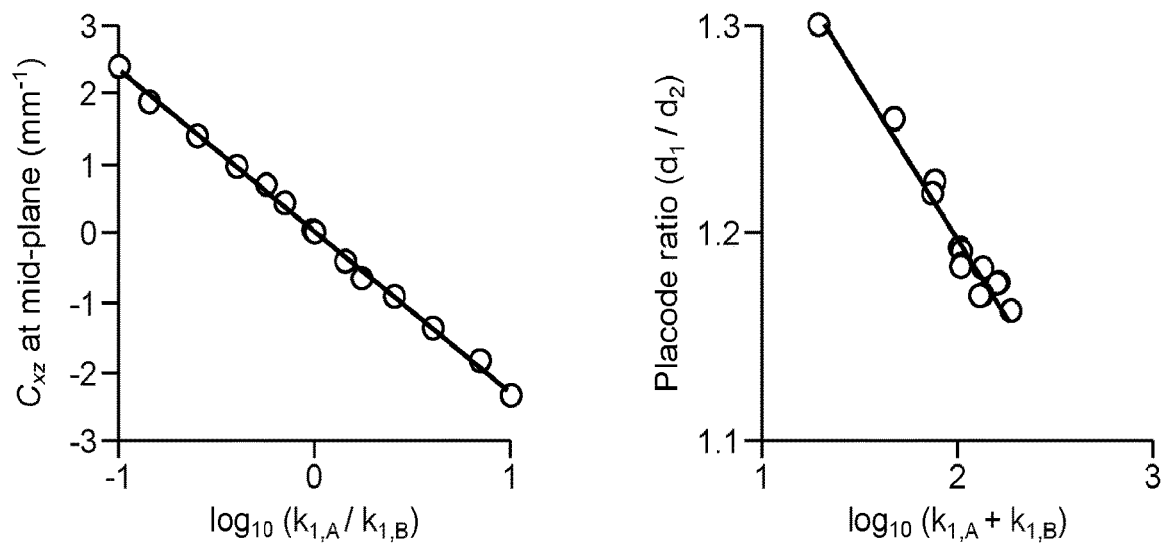

Importantly, our model does not invoke any physical property of overlying tissue layers, such as an epithelium. However, it predicts that these properties would affect the magnitude and polarity of tissue folding. Here, our reconstituted tissues and FEM models treat the overlying material as having negligible bending modulus. Thus, a condensation near the upper surface of reconstituted tissues always forms a region of concave curvature. However, if the overlying material has a higher bending modulus than the mesenchyme, modeling predicts an inversion of the curvature direction, converting an invagination into an evagination (FIG. 6). The model further suggests a coincident lateral compaction of the overlying layer during a condensation event, forming a structure similar to a placode. These studies leave open an intriguing possibility: that paracrine signaling originating in the mesenchyme could serve to set the mechanical properties of an overlying epithelium, thereby determining the direction and magnitude of folding during a condensation event. Such a view of mesenchymal epithelial interaction could explain how different combinations of epithelium and mesenchyme transition to markedly different tissue architectures through an interplay between tissue mechanics and paracrine signaling. Combined with the established roles of the epithelium in tissue buckling, our results suggest that a combination of mechanically active tissue components could collaborate to initiate and reinforce the pattern, polarity, and magnitude of tissue folding (Hirashima, 2014; Lecuit et al., 2011; Nelson, 2016; Odell et al., 1981; Oster and Alberch, 1982; Savin et al., 2011; Shyer et al., 2013; Tallinen et al., 2016; Varner et al., 2015).

Apart from its relevance to developmental biology, our study raises the possibility that dynamic control over both the material and physical properties of cell-ECM composites is readily achievable. In this view, building tissues de novo is a 4D process—where initial tissue structures are assembled in 3D, but evolve in time across multiple length scale according to specific developmental principles, converging ultimately on a new 3D structure with more defined and life-like structural features. This approach could significantly improve the structure, maturation, and vascularization of organoid tissue models at mesoscale (Lancaster and Knoblich, 2014; Takebe et al., 2015). We believe these efforts have important implications for the engineering of in vitro models of disease, for regenerative medicine, and for future applications of living active materials such as in soft robotics.

Figure 4:
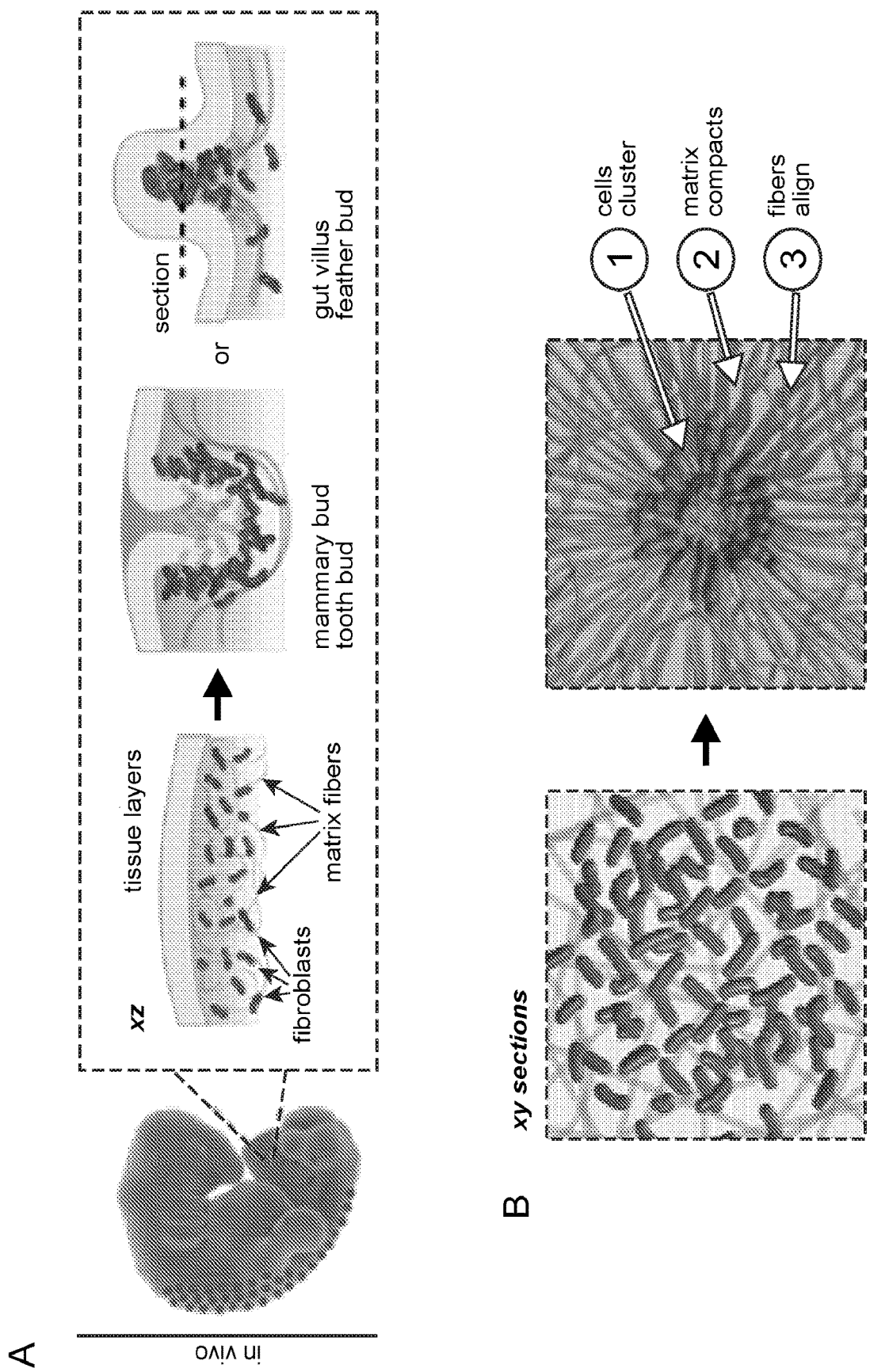
FIG. 4 illustrates reconstitution of tissue folding through mesenchymal condensation mechanics.
Figure 4:
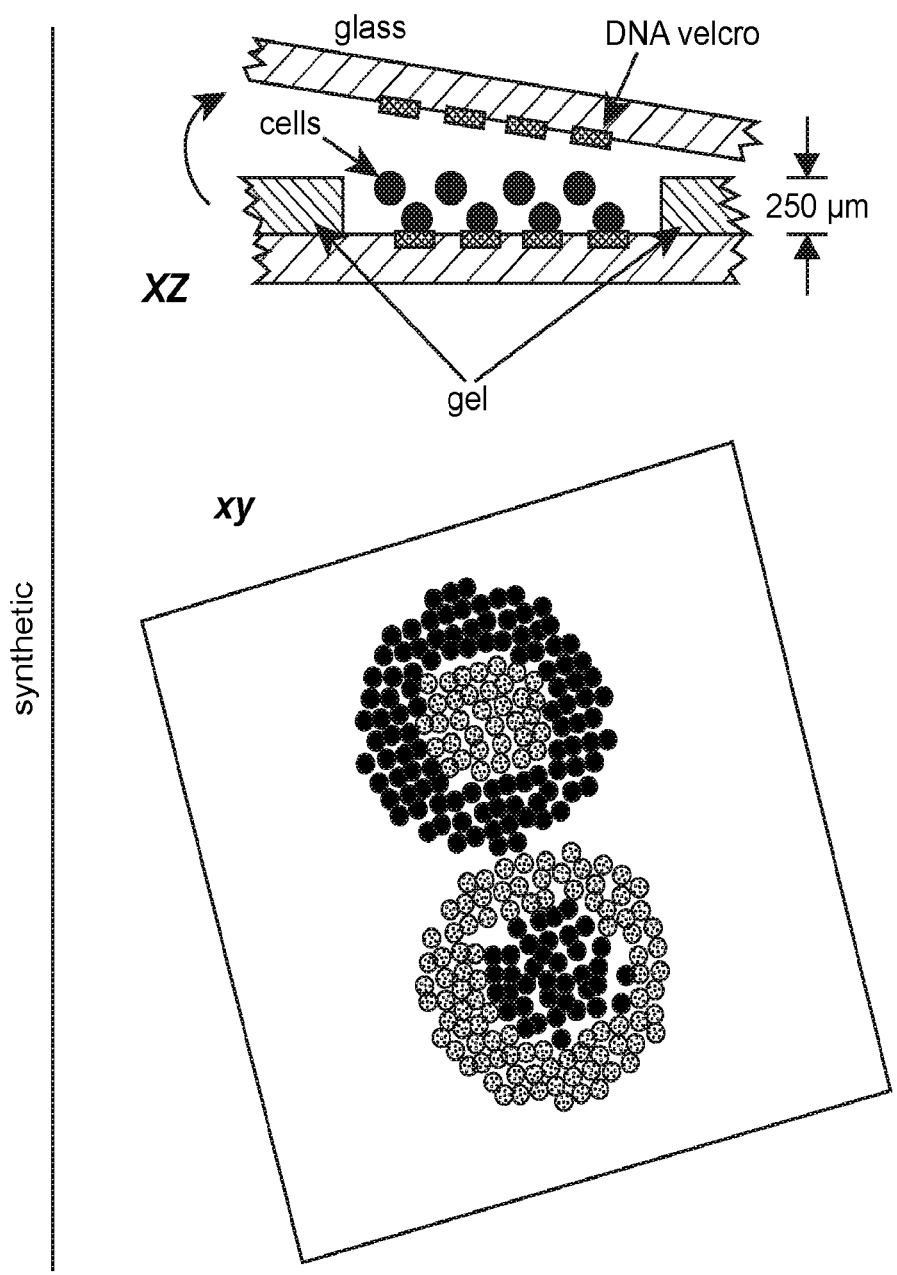
Figure 4:
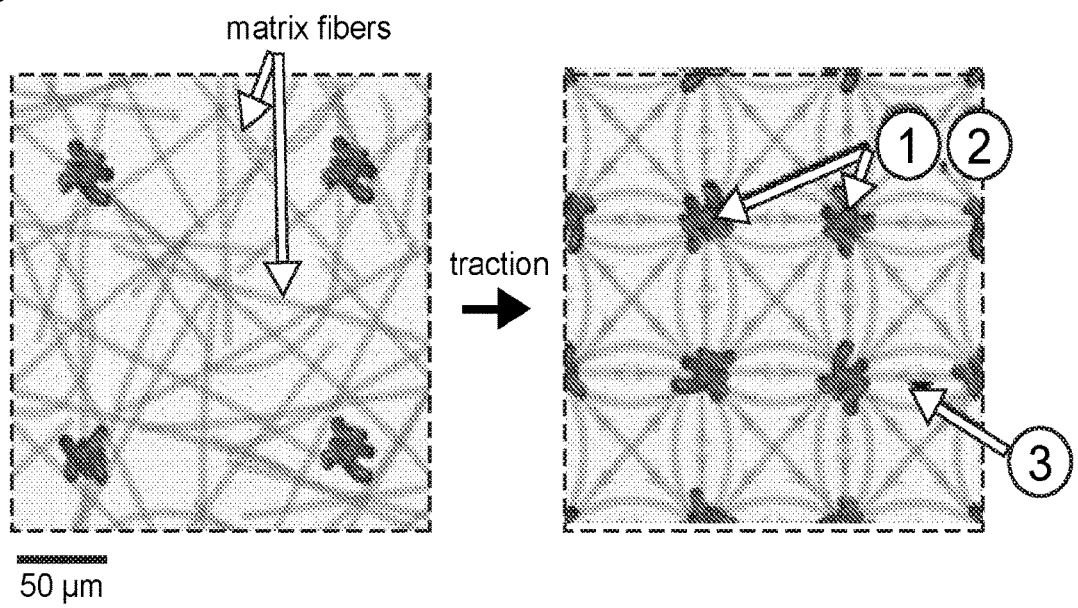
Figure 4:
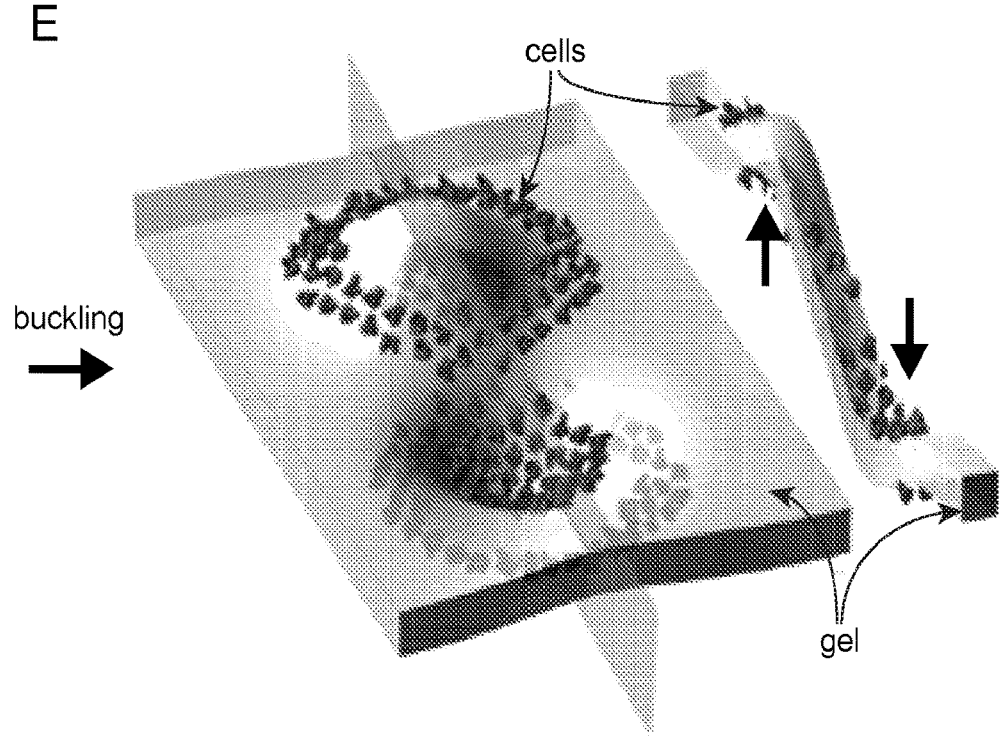

FIG. 4. Reconstitution of Tissue Folding Through Mesenchymal Condensation Mechanics.

(A) Shape transitions at the interface of tissue layers in vertebrate embryos often coincide with condensation of mesenchymal cells at sites of inward or outward curvature. (B) Cells along the interface converge on foci and exhibit three signatures during mesenchymal condensation. (C) Reconstitution of condensation using DNA-programmed assembly of cells to build small clusters of cells near the upper and lower surfaces of ECM gels containing collagen matrix fibers. (D) Strain fields are imposed by the traction of cell clusters on their fibrous extracellular microenvironments, locally aligning collagen fibers and generating in-plane forces that lead to tissue buckling (E).

Figure 5:
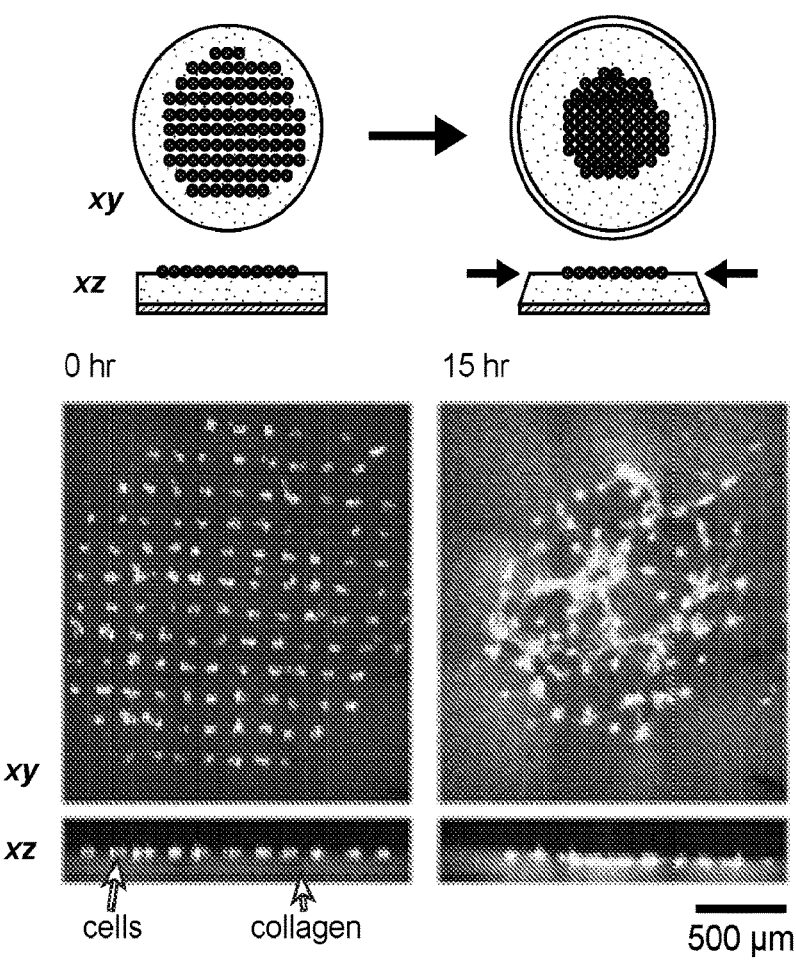
FIG. 5 illustrates that a reconstituted system exhibits signatures of mesenchymal condensation and folds along predictable trajectories.
Figure 5:
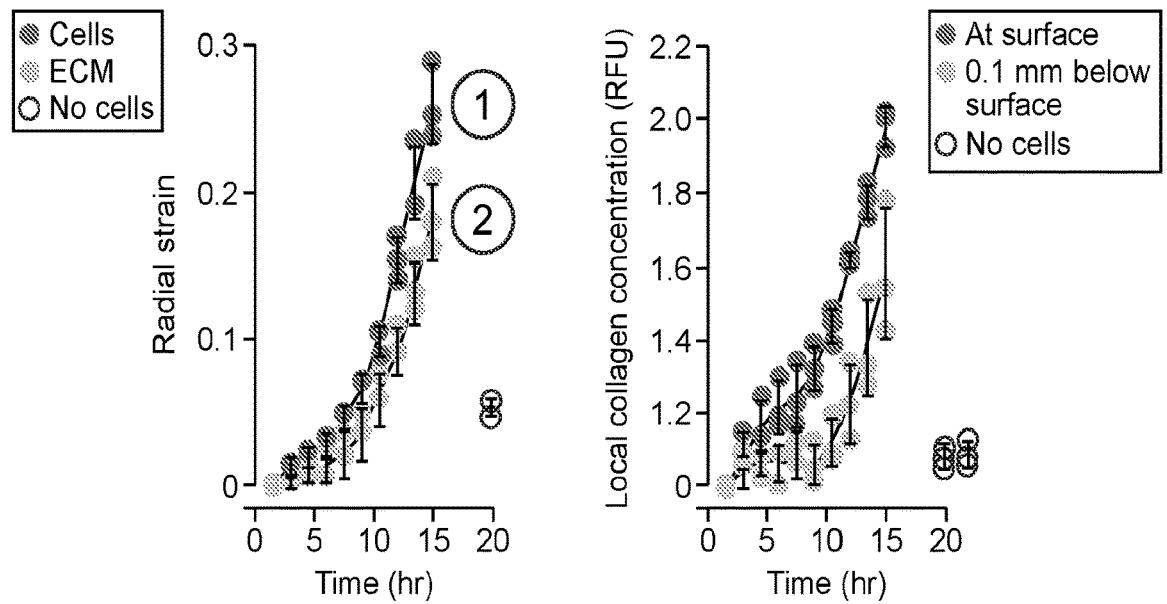
Figure 5:
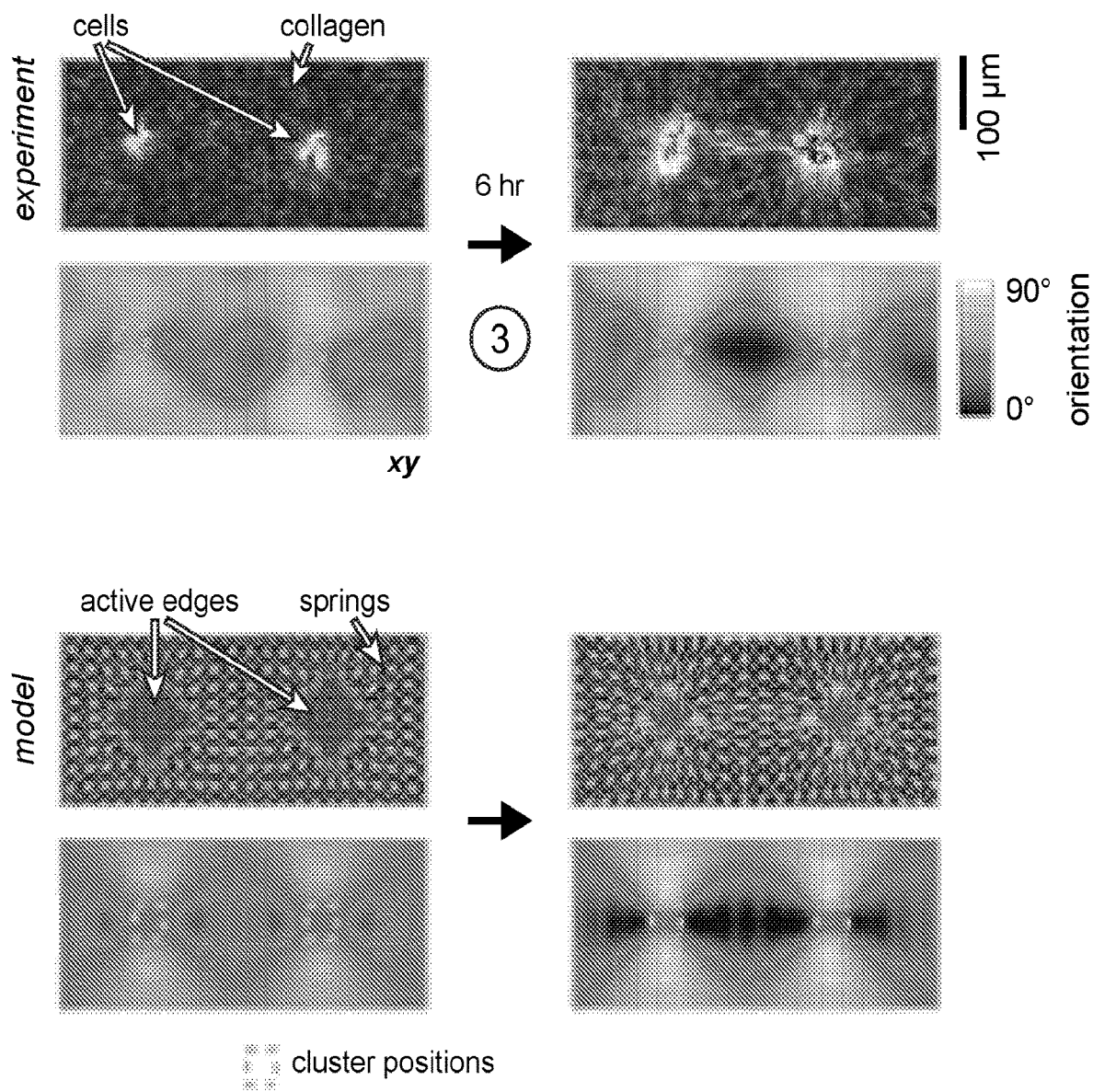
Figure 5:
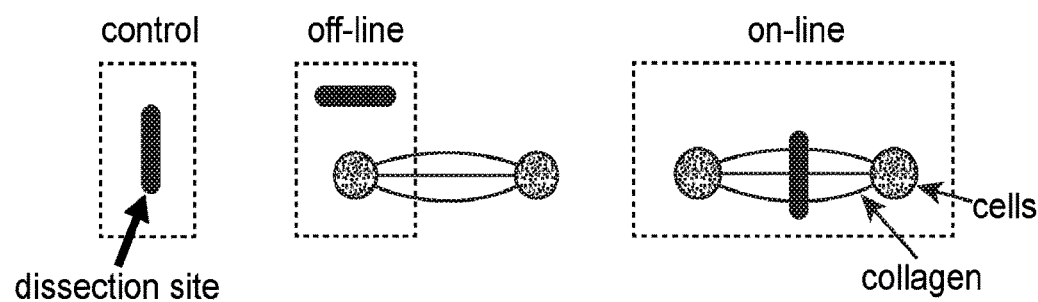
Figure 5:
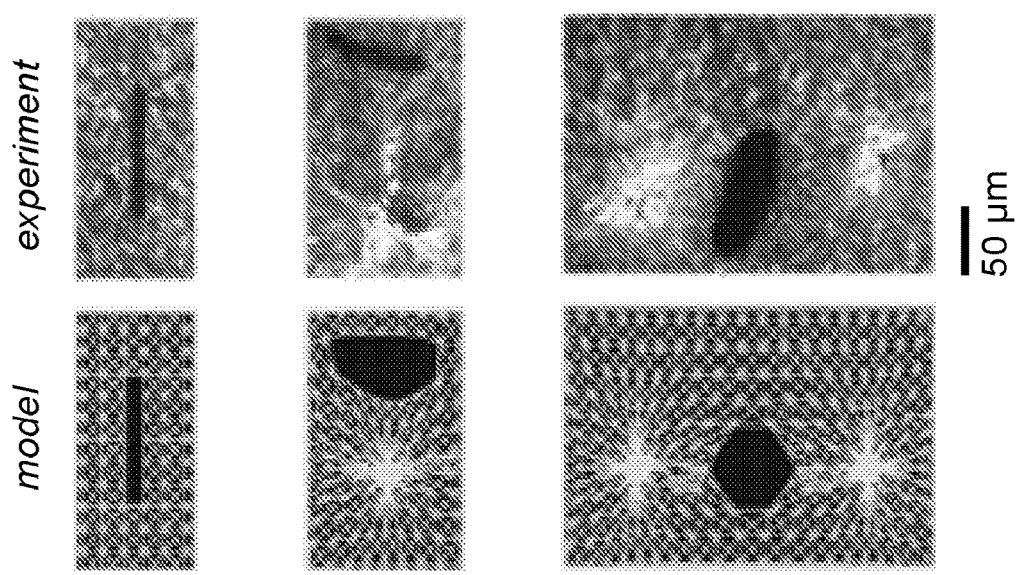
Figure 5:
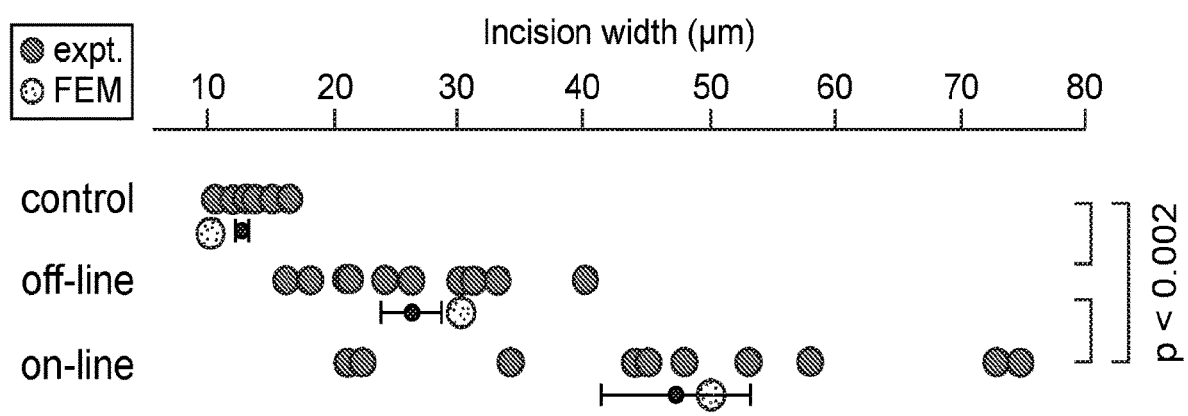
Figure 5:
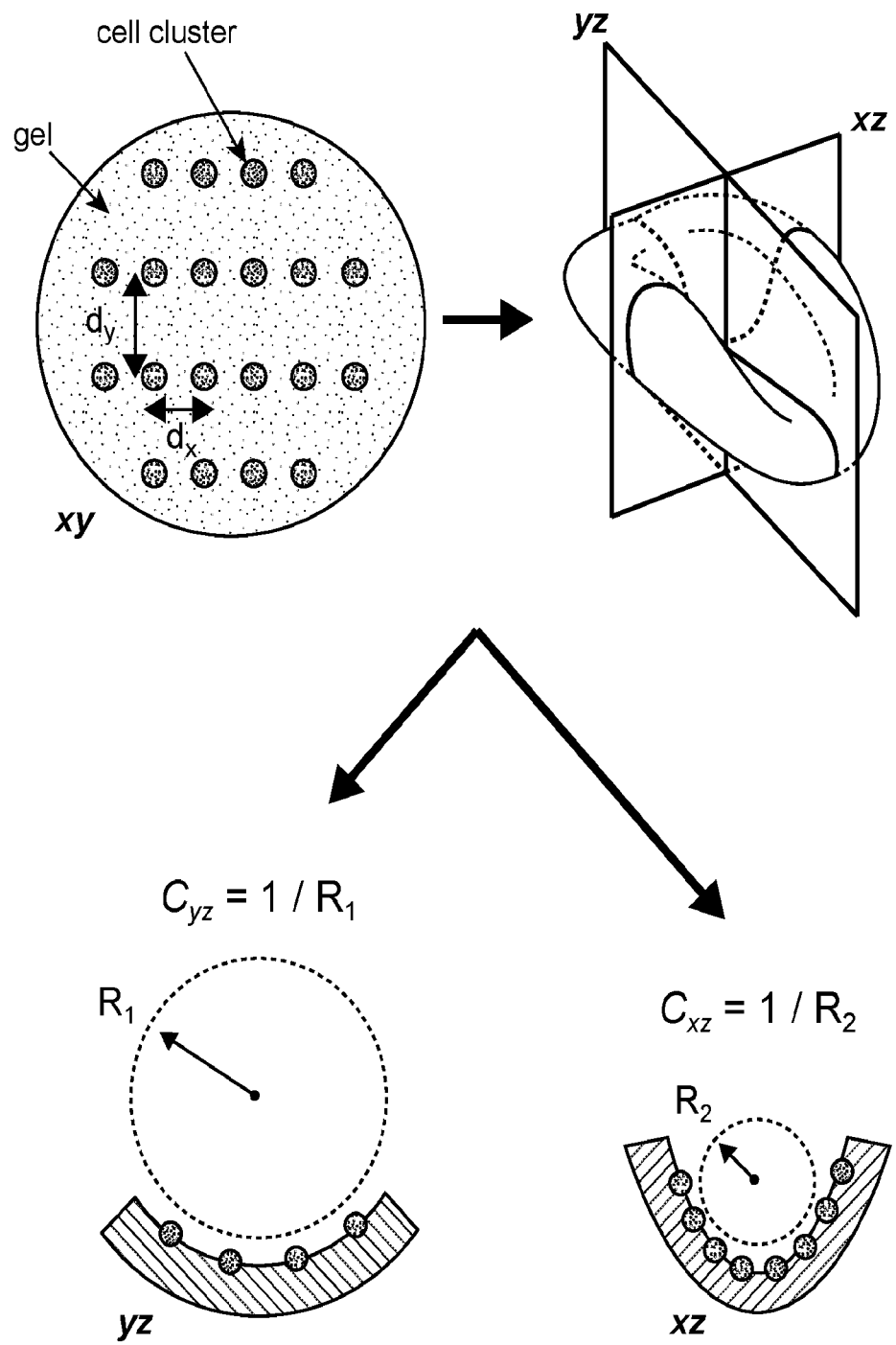
Figure 5:
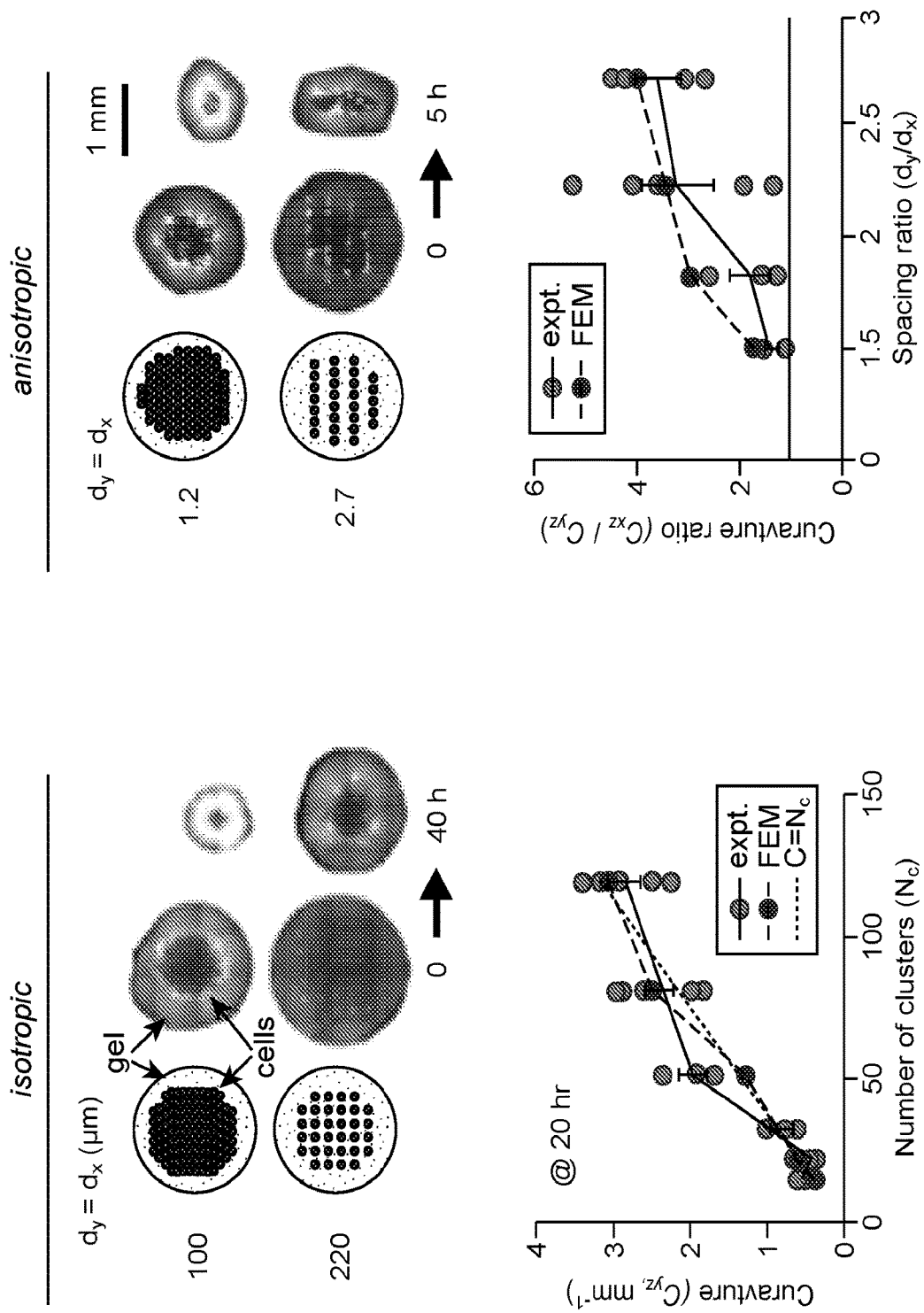

FIG. 5. A Reconstituted System Exhibits Signatures of Mesenchymal Condensation and Folds Along Predictable Trajectories.

(A) Patterned grids of mouse embryonic fibroblasts (MEFs) converge towards a central focus. Independent measurements of radial strain of the cell grid and its underlying ECM show matrix compaction at the tissue-medium interface to be a dominant contributor (mean±SEM, n=3). (B) MEF clusters align collagen fibers across hundreds of microns. Similar alignment of elastic edges in a finite-element model (FEM) occurs between contractile nodes consisting of active edges whose length can be reduced to simulate local gel strains by cell clusters. (C) Gel retraction after laser ablation implies significantly higher tensile forces along the axis between clusters (on-line) relative to the orthogonal axis, with similar behavior in the FEM (off-line, one-way ANOVA with Holm-Sidak's multiple comparisons test, n >9 incisions per group). (D) Calibration curves for isotropic MCC and anisotropic MEF cluster grids that quantitatively encode curvatures of reconstituted tissues in the xz and yz planes (mean±SEM, n >2 per grid geometry). A 3D version of the FEM in (B) broadly captures these curvature relationships.

FIG. 6. ECM Tension at Tissue Interfaces Leads to Invagination or Evagination Dependent on Differences in Layer Mechanics.

(A) Finite element model consisting of an elastic network subject to internal planar strains imposed via active edges at the interface of two layers A and B having different non-active edge stiffnesses $k_{1,A}$ and $k_{1,B}$. (B) Imposing a strain on active edges by reducing their length from s=1 to s=0.5 triggers curvature at the interface whose magnitude and sign depends on the nonactive edge stiffness ratio $k_{1,A}/k_{1,B}$, (C). Further, placode-like thickening at the site of strain is more pronounced as the overall stiffness in the model ($k_{1,A}+k_{1,B}$) decreases.

Figure 7:
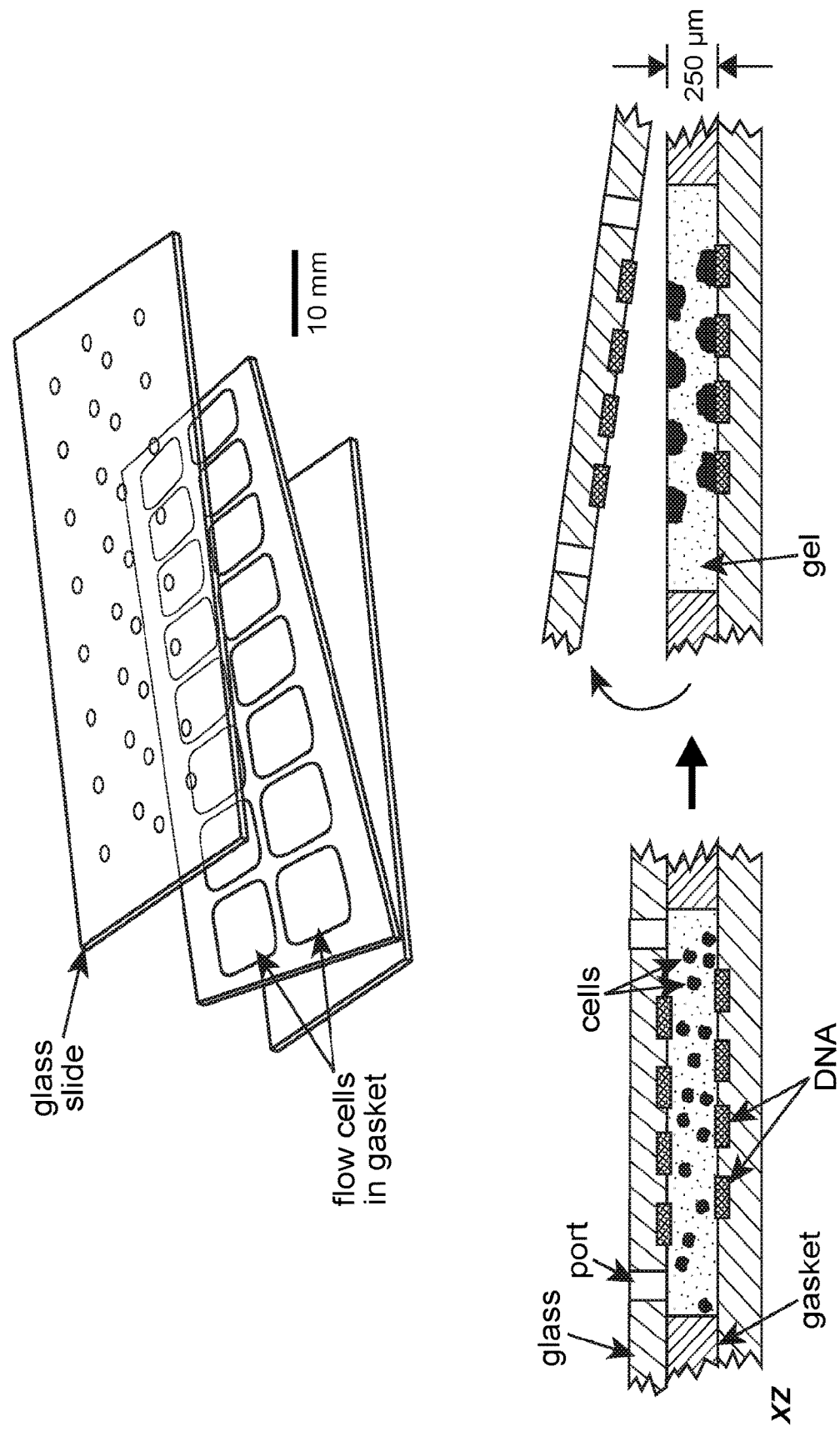
FIG. 7 illustrates reconstituted tissue fabrication by microfluidic integration of DNA Programmed Assembly of Cells (DPAC).
Figure 7:
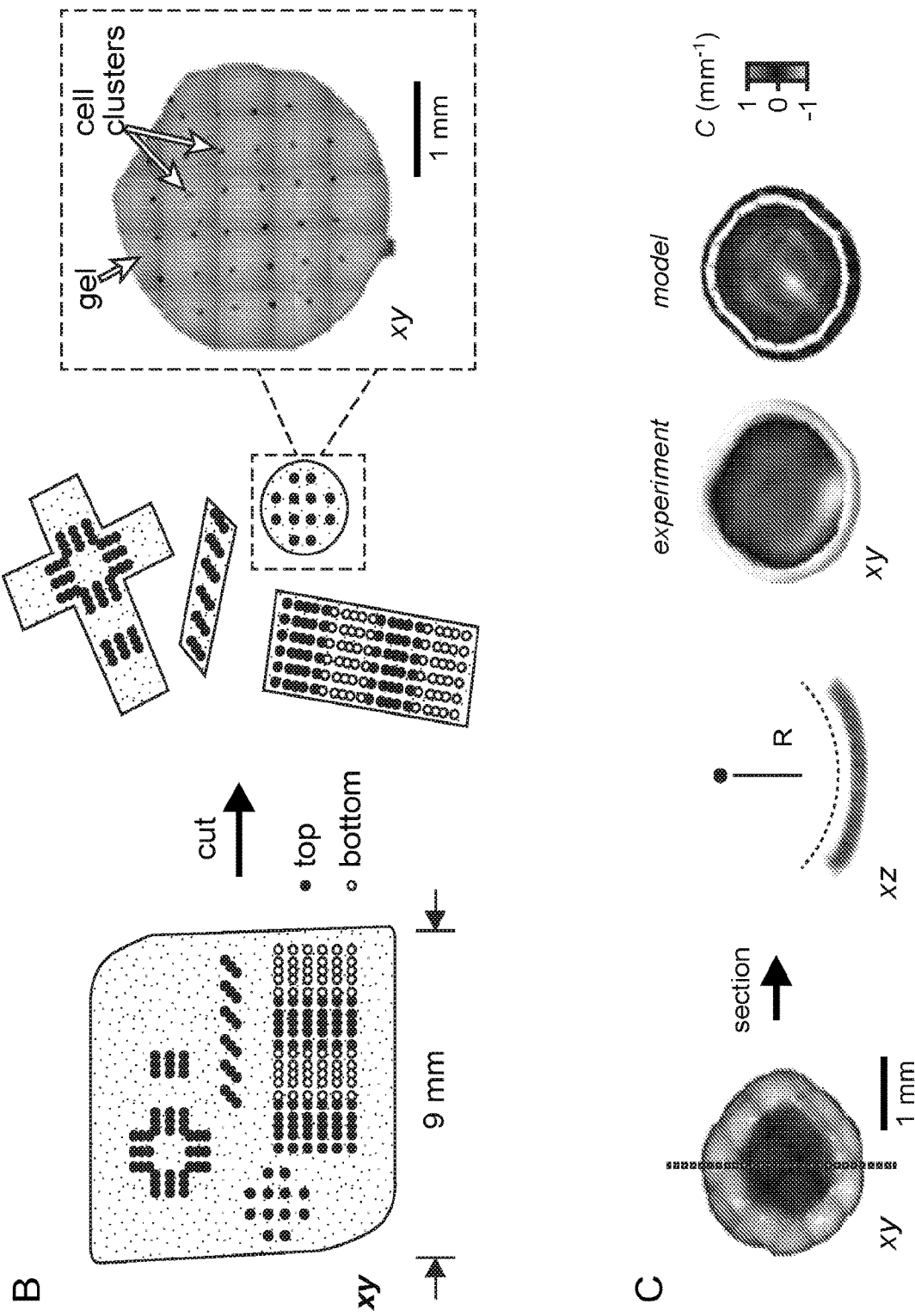

FIG. 7. Reconstituted Tissue Fabrication by Microfluidic Integration of DNAProgrammed Assembly of Cells (DPAC).

(A) Reconstituted tissues are built in glass flow cells fabricated from glass microscope slides spaced apart via a gasket. The top glass slide contains two through-holes per flow cell to enable fluidic access. Contractile cell positions in the gel are encoded by DPAC or by standard cell arraying technologies (FIG. 8). In DPAC, complementary DNA strands on cells and on the glass slides are used to direct cells to specific xy locations at the upper and/or lower surfaces of each flow cell. A liquid gel precursor is then added and set, finally (B) the glass slides are separated and the reconstituted tissues cut by manual dissection or by laser microdissection. Here we used an isotropic grid of mouse embryonic fibroblast clusters to encode a cap shape. (C) Confocal imaging (here, midplane xy and xz sections) enables measurement of object-wide curvature by fitting of circles or measurement of local curvatures by computational reconstruction of mesh objects that can be semi-quantitatively compared to corresponding meshes from FEM.

FIG. 8. Reconstituted Tissue Fabrication by Non-Contact Cell Printing.

(A) ECM gels can be cast and subsequently printed with cells in a semi-dry format using a noncontact arrayer. (B) Mouse embryonic fibroblasts successfully attach in loose clusters. (C) Cell-printed reconstituted tissues carrying isotropic grids exhibit curvature after 6 hr in culture.

FIG. 9.

Cell clusters are isotropic attractors that radially align collagen at rates dependent on cell type. (A) Mouse embryonic fibroblasts (MEFs) embedded at the surface of collagen-rich ECM gels locally align fluorescently-labeled collagen 1 fibers and induce interface curvature over time. (B) Left, average collagen orientation maps induced by MEF or mesenchymal-like carcinoma cell (MCC) clusters. Right, fiber orientation was quantified by sampling average image orientation in regions of interest (ROIs) along the x and y axes and at two radii (r) relative to clusters. (C) Corresponding radial alignments observed in a 2D elastic finite element model. (D) Alignment excess (average ROI orientation −orientation at t=0, mean±SEM, n >4 per condition) was equivalent along x and y axes and higher at 6 hr for isolated MEF clusters than for MCC clusters. (E) Alignment at 6 hr decayed radially away from MEF and MCC clusters (mean±SEM, n=12 per condition). Alignment excess data in (D) and (E) were analyzed by one-way ANOVA with Holm-Sidak's multiple comparisons test. (F) Similar alignment excess magnitudes in x and y are also observed in the FEM upon application of active edge strain. (G) Similar radial spatial decay of alignment excess is observed in the model.

FIG. 10. Cell Cluster Pairs Amplify Collagen Fiber Alignment Between them Over Distances of Hundreds of Microns.

(A) Collagen strap formation between mouse embryonic fibroblast (MEF) clusters. (B) Left, average collagen orientation maps for clusters separated by three distance ranges. Right, fiber orientation was quantified by sampling average orientation in ROIs at 50 μm along x and y axes from the left-hand cluster in each pair. (C) Alignment excess between MEF clusters (along x) was higher than in the orthogonal direction (along y) for all distance ranges at 6 hr, as well as for mesenchymal-like carcinoma cell (MCC) cluster pairs except at the largest distance, in which clusters appear to behave as isolated isotropic attractors (i.e. alignment fields had not coupled together at this time point). Alignment excess plotted as mean±SEM, n >4 per condition, analyzed by one-way ANOVA with Holm-Sidak's multiple comparisons test. (D) Similar increases in alignment excess along the axis between clusters is observed in the finite element model upon application of active edge strain. (E) Strap formation between an isolated pair of MEF clusters coincides with a spatially expanding region of local interfacial curvature.

FIG. 11. Rates of Reconstituted Tissue Curvature are Determined by the Rate at which Actuating Cells Strain the Gel.

(A) Top, cell strain rates are inferred by measuring bead displacement proximal to single cells from mesenchymal-like carcinoma cell (MCC) line clones (MCC1-3) and primary human mammary fibroblasts (mam. fib.) on top of collagen-rich ECM gels. Inset: A single MCC2 cell exerting traction that leads to local bead displacement. Bottom, midplane xy confocal sections show variation in folding state depending on cell type that can be quantified by evaluating reconstituted tissue curvature rates. (B) Curvature rates of d=181 μm isotropic tissues are determined from initial slopes of (radially) maximum curvature trajectories against time. (C) The tissue curvature rate (mean±SEM across, n >2 per cell type) induced by a given actuating cell type is approximately proportional to its strain rate.

FIG. 12. Isotropic Reconstituted Tissues Follow Monotonic Curvature Trajectories.

(A) Left, schematic of curvature measurement procedure for ECM gels patterned with isotropic grids of contractile mesenchymal-like carcinoma cell (MCC) clusters. Right, xy confocal sections showing that reconstituted tissues develop curvature at rates increasing as a function of grid density. (B) Curvature trajectories of individual tissues actuated by MCC cluster grids of the indicated spacing. Curvatures appear to saturate at radii on the order of the gel thickness.

FIG. 13. Reconstituted Tissues Only Partially Unfold after Ablating Actuator Cells.

(A) Killing mesenchymal-like carcinoma cells with 20 μM staurosporine (a non-specific kinase inhibitor) leads to modest reductions in pre-folded isotropic tissue curvatures as observed via xy confocal sections and plotted as maximum curvature relative to the average maximum curvature in each reconstituted tissue group immediately prior to addition of staurosporine (n=4 reconstituted tissues per condition, plotted as mean±95% confidence interval envelopes). (B) The efficacy of staurosporine was assayed in a separate experiment on cells cultured on standard tissue culture plastic, in which 20 μM staurosporine was sufficient to cause nearly complete cell death (cell viability plotted as mean±SEM, n=6).

FIG. 14. Fidelity of Anisotropic Folds is Limited by Contractile Cluster Migration.

(A) Left, schematic depicting curvature measurements for reconstituted tissues patterned with anisotropic grids of mesenchymal-like carcinoma cells (MCC) or mouse embryonic fibroblast (MEF) clusters. Right, xy confocal sections and reconstructed meshes showing that anisotropic MEF grids induce anisotropic folds along the intended axis, while anisotropic MCC grids do not. (B) Curvature anisotropy increased with cluster spacing anisotropy for MEF reconstituted tissues but not for MCC tissues. (C) Quantitation of cell migration in anisotropic grids in the same experiment as (D). We quantify the median time Td/2 for cells to reach a distance of half the cluster spacing d/2 from their initial positions. (D) Radial bar charts normalized by maximum bin value for collagen strap orientation relative to horizontal for isotropic and anisotropic MCC and MEF grids. Note significant off-axis strap orientation for MCC grids at 15 hr but not for MEF grids.

FIG. 15. Mesenchymal Condensation is Sufficient to Sculpt Tissue Interfaces into Diverse 3D Forms.

(A) Five folding motifs built using 3D finite-element models. (B) Contractile node positions encoding model helical and tubular tissues, shown as meshes colored by local mean curvature, C, and as mid-tissue sections. (C) Reconstructions of confocal micrographs as curvature-mapped meshes of corresponding tissues at two imaging time-points. (D), (E) A developable corrugated tissue and a non-developable opposing cap tissue. Opposing curvature is encoded by positioning mouse embryonic fibroblasts on both the top (orange) and bottom (white) surfaces of reconstituted tissues. Mid-tissue sections fitted locally to each cap at 10° increments in azimuth around the y axis show comparable curvature profiles between neighboring caps and between model and experiment tissues. (F), (G) Folded spherical and cubic reconstituted tissues enabled by strategic cutting using laser microdissection.

FIG. 16. Section Analysis for Curl, Tube, and Corrugation Reconstituted Tissues.

(A) Experiment and model meshes, and orthogonal views for the curl tissue in FIGS. 15B and 15C. (B) Meshes and views for the tube in FIGS. 15B and 15C. (C) xy planes and several xz sections for the corrugation tissue in FIGS. 15D and 15E.

FIG. 17. Section Analysis for Double Cap, Sphere, Cube, and Miura Reconstituted Tissues.

(A) Experiment and model meshes, xy sections, and yz sections through the cap centers for the double cap tissue in FIGS. 15D and 15E. Circles fitted to the caps as a function of angle in the xy plane show curvature uniformity. (B) Meshes and orthogonal views for the sphere in FIGS. 15F and 15G. (C) Meshes and orthogonal views for the cube in FIGS. 15F and 15G. (D) Experiment and model meshes and xz sections along the length of the Miura tessellation at 15 hr in FIG. 19B.

FIG. 18. Opposing Folds in Reconstituted Tissues are Robust to Pop-Through Defects.

(A) A simple opposing fold is the four-fold vertex. We quantified the curvatures in each fold for reconstituted tissues with different numbers of mouse embryonic fibroblast clusters patterned in the opposing fold (fold 2). (B) For low numbers of clusters along the opposing fold, it pops outwards into the incorrect orientation, whereas it emerges in the correct orientation for cluster numbers at a ratio of higher than around 0.75× the average number of clusters in the neighboring folds (ratios plotted with linear least squares fits and a 95% confidence interval envelope for experiment data). (C) Mesh reconstructions of reconstituted tissues in the pop-through and correct fold configurations.

Figure 19:
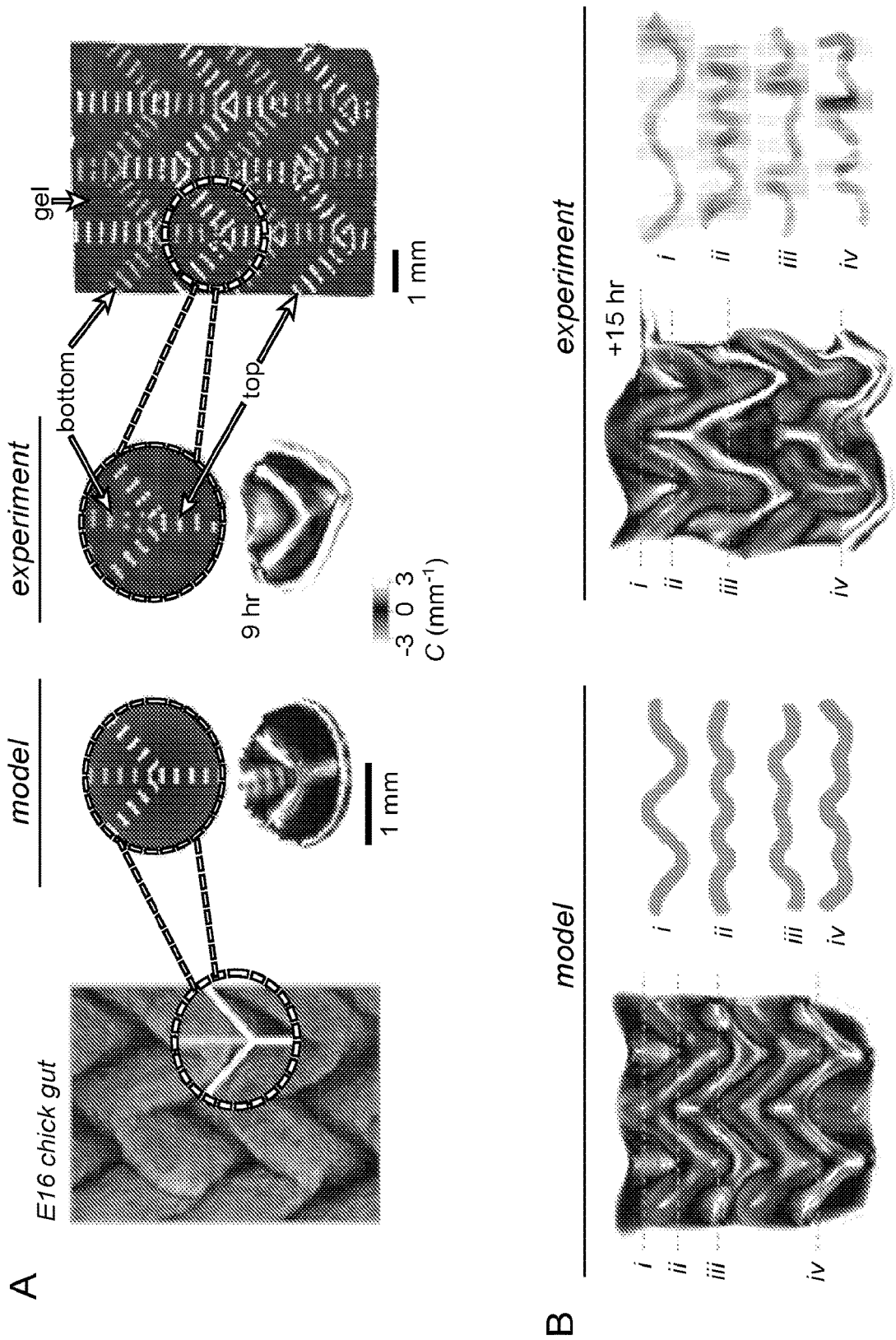
FIG. 19 illustrates mesenchymal condensation-driven tissue folding is robust to simultaneous self assembly of multiple cell types near complex folds.
Figure 19:
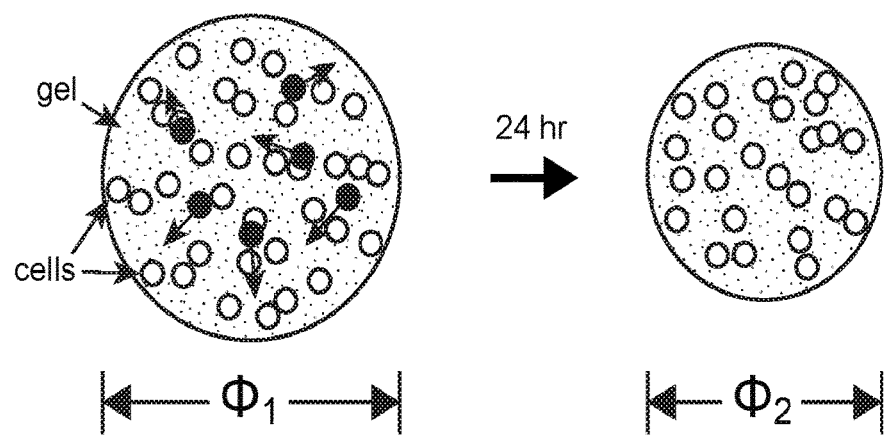
Figure 19:
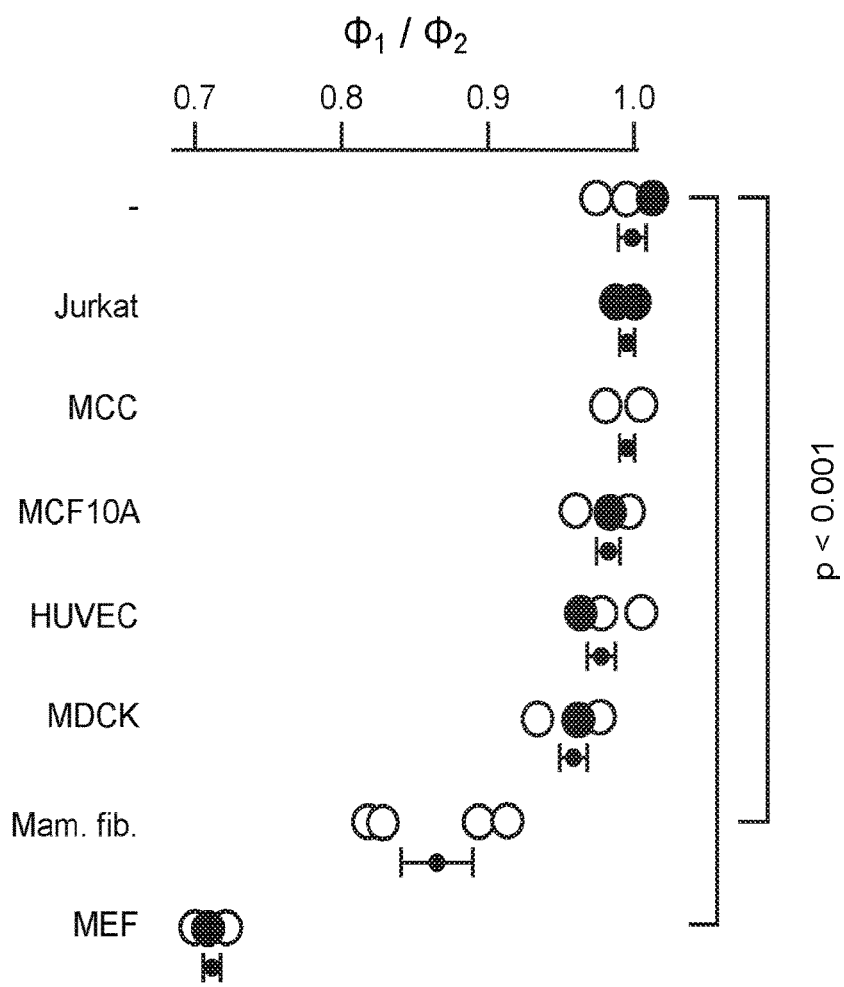
Figure 19:
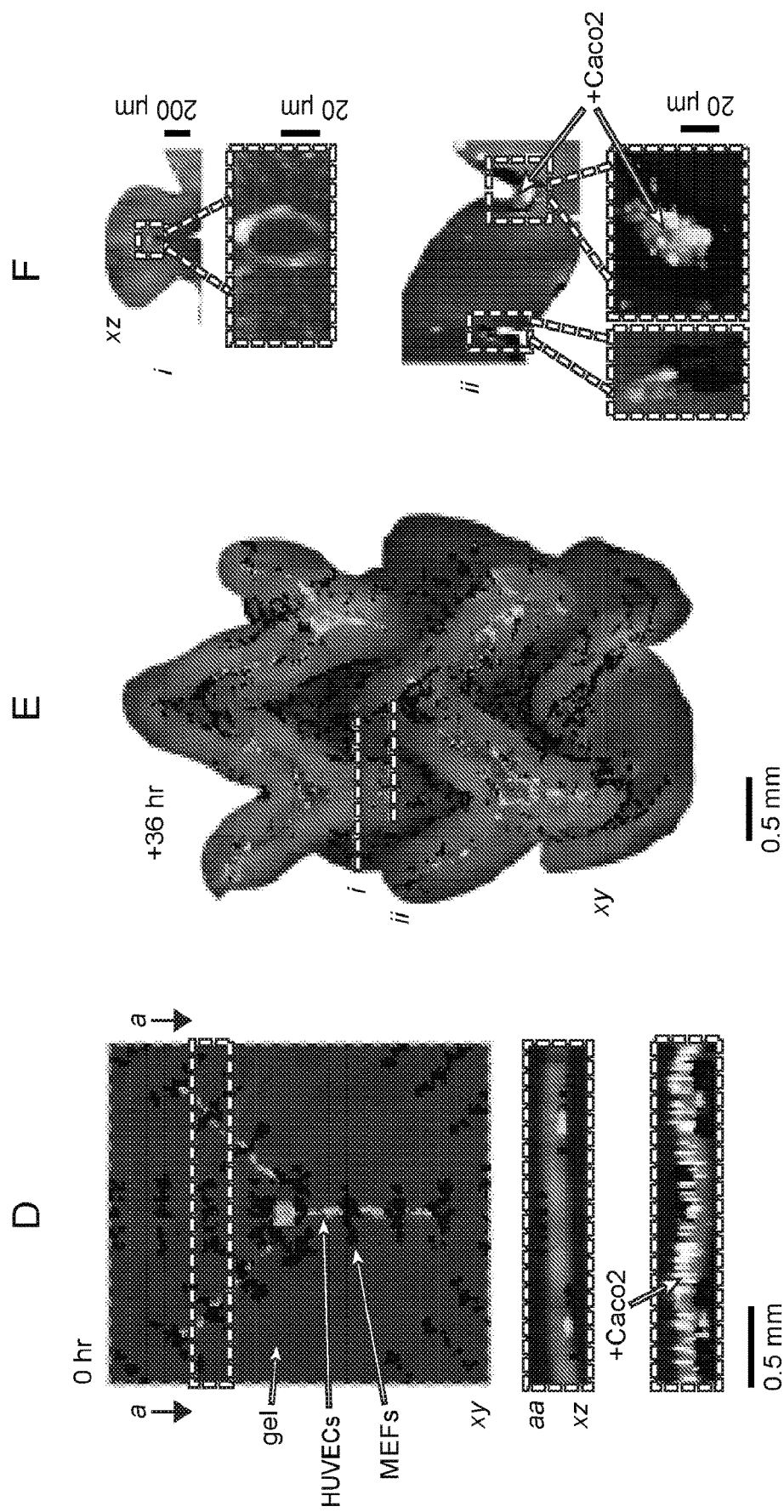
Figure 20:
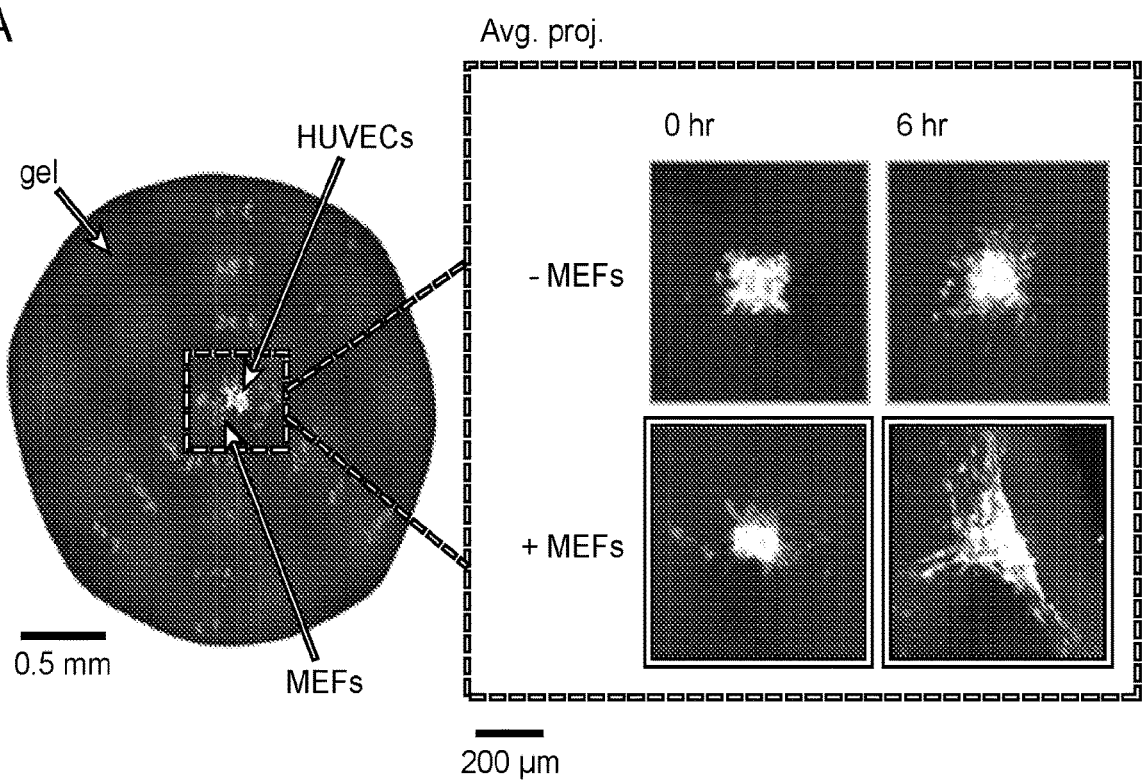
FIG. 20 illustrates that passenger HUVECs exhibit biased motility along nascent folds.
Figure 20:
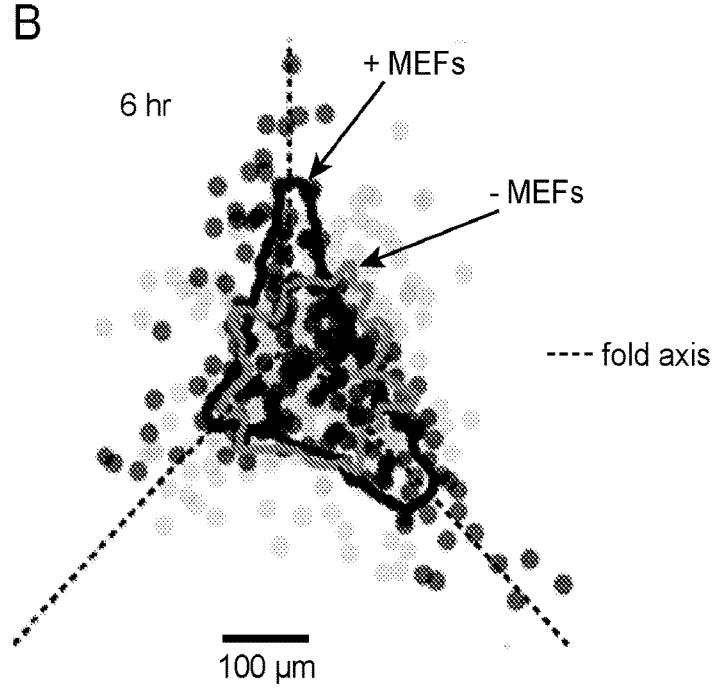

FIG. 19. Mesenchymal Condensation-Driven Tissue Folding is Robust to Simultaneous Self Assembly of Multiple Cell Types Near Complex Folds.

(A) The embryonic day 16 (E16) chick gut lumen exhibits a zig-zag Miura-like fold that can be reconstructed by tiling of a fourfold-vertex pattern encoded by condensing mouse embryonic fibroblast clusters. (B) Model and experiment folds show multiple xz profiles with matching fold periodicity and amplitude. (C) Contraction of collagen-containing ECM droplets occurs to a much greater extent for mesenchymal and other fibroblast cell types (mean±SEM, n=4, one-way ANOVA with Holm-Sidak's multiple comparisons test). (D) Human umbilical vein endothelial cells (HUVECs) patterned as 3-pronged cords along adjacent folds of four-fold vertex patterns in a Miura tissue, (E). (F) Representative cross-sections showing lumenized HUVEC cords enveloped by Miura folds and Caco2 cells deposited as a partially continuous layer embedded within the upper surface of the tissue. Caco2 cell clusters form atop contractile fibroblasts within concave folds.

FIG. 20. Passenger HUVECs Exhibit Biased Motility Along Nascent Folds.

(A) Patches of human umbilical vein endothelial cells (HUVECs) were patterned at the convergence point of the three folds of equivalent polarity in n=9 four-fold vertex reconstituted tissues actuated by mouse embryonic fibroblasts (MEFs). The spatial distribution of HUVECs was determined after 6 hr and compared to that for control tissues in which no MEFs were present to actuate folding. Folds had maximum curvatures of <1 $mm_{-1}$ at 6 hr, such that parallax errors in the measurement of cell positions could be ignored. (B) Locally averaged radial cell distance plots show a HUVEC migration bias along nascent folds.

Example 2: Mesenchymal Cell Condensation at In Vivo Sites of Curvature is Associated with Collagen 1 Compaction and Alignment Our studies broadly show that mesenchymal cell condensation in vivo at sites of biological curvature (at the gut villi and chicken skin buds) is associated with similar collagen 1 compaction and alignment that we generate in our reconstituted tissue models.

Figure 21:
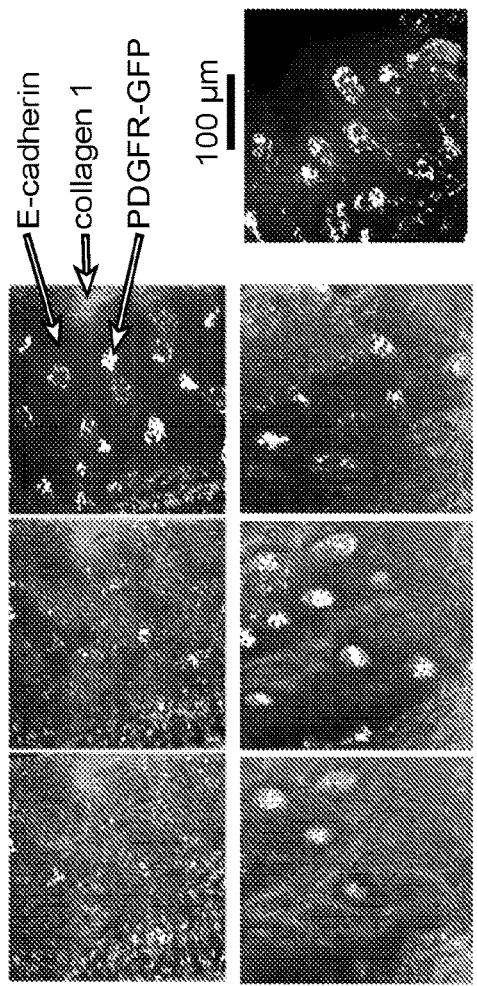
FIG. 21 illustrates that mesenchymal cell condensation in vivo at sites of biological curvature (at the gut villi and chicken skin buds) is associated with similar collagen 1 compaction and alignment as generated in the reconstituted tissue models provided herein.
Figure 21:
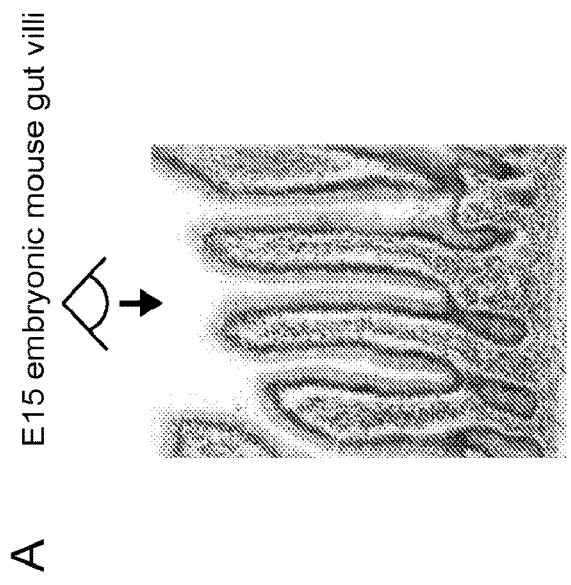
Figure 21:
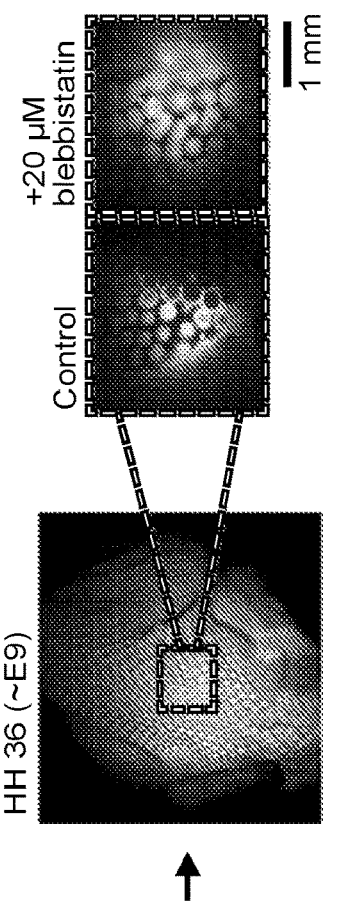
Figure 21:
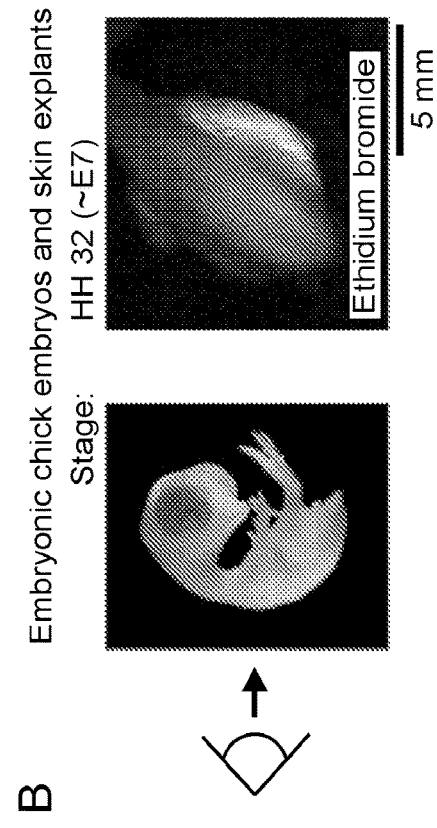

FIG. 21. (A). Gut villi in embryonic mice form in concert with condensation of PDGFR-positive mesenchymal fibroblasts at sites of villus curvature. These clusters are associated with local alignment and compaction of collagen 1 fibrils against the E-cadherin-positive epithelium. In results not shown, we found that cell clustering and collagen 1 remodeling does not occur in explanted guts treated with the myosin II inhibitor blebbistatin, which blocks cell mechanical contractility in the system. B) Feather buds in embryonic chickens form from a flat epithelium, and can be visualized with non-specific ethidium bromide staining Chick skin explants at Hamburger-Hamilton (HH) stage 32 form feather buds in culture, but feather bud spacing and height are disrupted in the presence of blebbistatin.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of making a planar biological tissue configured for folding into a three-dimensional shape, the method comprising:
    patterning contractile cells on a surface of a first and second substrate, comprising:
        disposing a pattern of nucleic acids on a first surface of the first substrate and a first surface of the second substrate, wherein the first surface of the first substrate is spaced apart from the first surface of the second substrate via a gap between the first and second substrates and wherein the surfaces are in a facing configuration to each other; and
        contacting the patterned nucleic acids under hybridization conditions with a suspension of the contractile cells, wherein the contractile cells comprise cell surface-attached nucleic acids complementary to the patterned nucleic acids, and wherein the cell surface-attached nucleic acids hybridize to the patterned nucleic acids to generate patterned contractile cells on the first surface of the first substrate and the first surface of the second substrate;

contacting the patterned contractile cells on the surfaces of the substrates with a polymer matrix comprising fibers thereby embedding the patterned contractile cells into the polymer matrix;

removing the polymer matrix from between the first and second substrates thereby generating a planar biological tissue comprising the patterned contractile cells on a top surface and a bottom surface of the planar biological tissue, wherein the patterned contractile cells are retained in the polymer matrix upon removal thereby generating a planar biological tissue configured for folding into a three-dimensional shape;

contacting the planar biological tissue with a culture medium; and incubating the planar biological tissue in suspension in the culture medium for a period of time sufficient for action of the contractile cells on the fibers for folding the tissue into a three-dimensional shape.

2. The method of claim 1, wherein the planar biological tissue comprises a region containing polymer matrix and pattern of cells and a region containing polymer matrix that is devoid of cells and wherein incubating the planar biological tissue in suspension for folding the tissue into a three-dimensional shape comprises separating the region containing polymer matrix and pattern of cells from the region containing polymer matrix that is devoid of cells and incubating the region containing polymer matrix and pattern of cells.

3. The method of claim 1, wherein the pattern of nucleic acids is two-dimensional.

4. The method of claim 1, wherein the method further comprises solubilizing the polymer matrix in the three-dimensional shape to yield a three-dimensional shape comprising fibers and contractile cells.

5. The method of claim 1, wherein the pattern of nucleic acids comprises a single population of nucleic acids having the same nucleotide sequence.

6. The method of claim 1, wherein the pattern of nucleic acids comprises two or more population of nucleic acids, wherein each population of nucleic acids comprises a unique nucleotide sequence, wherein the nucleic acids of each population are uniquely addressable on the first surface of the first and/or second substrate.

7. The method of claim 6, wherein the suspension of contractile cells comprises two or more unique populations of contractile cells, wherein each population of contractile cells comprises surface-attached nucleic acids complementary to one of the populations of nucleic acids in the pattern.

8. The method of claim 1, wherein the contractile cells are selected from the group consisting of: fibroblasts, epithelial cells, endothelial cells, skeletal muscle cells, smooth cells, cardiac cells, progenitors thereof, and combinations thereof.

9. The method of claim 1, wherein the cell surface-attached nucleic acids comprise a lipid moiety attached to a nucleic acid, which surface-attached nucleic acids are attached to the contractile cells by insertion of the lipid moiety into the plasma membrane of the contractile cells.

10. The method of claim 1, wherein removing the polymer matrix from the surface of the substrate comprises exposing the polymer matrix to a nuclease.

11. The method of claim 1, wherein the polymer matrix comprises hydrogels, alginate, poly-caprolactone (PCL), gelatin, agarose, or cellulose polymer.

12. The method of claim 1, wherein the fibers comprise collagen.

13. The method of claim 1, wherein the contacting the planar biological tissue with a culture medium comprises a step of constraining a portion of the planar biological tissue.

14. The method of claim 13, wherein constraining a portion of the planar biological tissue comprises attaching the portion of the planar biological tissue to a solid support that constrains the portion in an adhered state thereby preventing the portion from folding upon action of the contractile cells on the fibers, and wherein constraining a portion of the planar biological tissue comprises applying a compressive force to the portion.

15. The method of claim 1, wherein the contacting the planar biological tissue with a culture medium comprises the step of expanding a portion of the planar biological tissue thereby separating the contractile cells in the portion and/or diluting the amount of fibers present in the portion such that the expanded portion is prevented from folding.

* * * * *

UNITED STATES PATENT AND TRADEMARK OFFICE
CERTIFICATE OF CORRECTION

PATENT NO. : 10,920,190 B2
APPLICATION NO. : 16/098704
DATED : February 16, 2021
INVENTOR(S) : Zev Jordan Gartner et al.

Page 1 of 1

It is certified that error appears in the above-identified patent and that said Letters Patent is hereby corrected as shown below:

In the Specification

Please add a GOVERNMENT RIGHTS statement in Column 1, starting at Line 4, before the INTRODUCTION, as follows:
--STATEMENT REGARDING FEDERALLY SPONSORED RESEARCH
This invention was made with government support under grant no. W81XWH-13-1-0221 awarded by The United States Army Medical Research and Materiel Command. The government has certain rights in the invention.--.

In Column 19, Line 43, "1-BM" should read --FEM--.

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*